(12) United States Patent
Oliveira

(10) Patent No.: US 7,072,771 B2
(45) Date of Patent: Jul. 4, 2006

(54) SELECTIVE PARP-1 TARGETING FOR DESIGNING CHEMO/RADIO SENSITIZING AGENTS

(75) Inventor: Marcos Oliveira, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 179 days.

(21) Appl. No.: 10/163,587

(22) Filed: Jun. 7, 2002

(65) Prior Publication Data

US 2003/0096263 A1 May 22, 2003

Related U.S. Application Data

(60) Provisional application No. 60/296,110, filed on Jun. 7, 2001.

(51) Int. Cl.
G06F 19/00 (2006.01)
C12Q 1/25 (2006.01)
(52) U.S. Cl. .............................. 702/27; 435/4
(58) Field of Classification Search ................ 530/300; 435/7.1

See application file for complete search history.

(56) References Cited

U.S. PATENT DOCUMENTS

| | | | |
|---|---|---|---|
| 5,032,617 A | 7/1991 | Lee et al. | 514/617 |
| 5,041,653 A | 8/1991 | Lee et al. | 564/74 |
| 5,215,738 A | 6/1993 | Lee et al. | 424/10 |
| 5,587,384 A | 12/1996 | Zhang et al. | 514/309 |
| 5,952,169 A | 9/1999 | Bürkle et al. | 435/6 |
| 6,074,876 A | 6/2000 | De Block | 435/468 |
| 6,100,283 A | 8/2000 | Griffin et al. | 514/394 |
| 6,121,278 A | 9/2000 | Jackson et al. | 514/292 |
| 6,201,020 B1 | 3/2001 | Zhang et al. | 514/544 |

OTHER PUBLICATIONS

Jan Drenth, Principles of Protein X-ray Crystallography, 1995, Springer-Verlag, p. 16.*
News Focus, Science, Nov. 1, 2002, vol. 298, pp. 948-950.*
Amé J-C et al., "PARP-2, A novel mammalian DNA damage-dependent poly(ADP-ribose) polymerase." *J Biol Chem*. 274(25): 17860-8 (1999).
Auer B et al., "Human nuclear NAD+ ADP-ribosyltransferase(polymerizing): organization of the gene." *DNA* 8(8): p. 575-80 (1989).
Bork P et al., A superfamily of conserved domains in DNA damage-responsive cell cycle checkpoint proteins. *Faseb J*. 11(1): 68-76 (1997).
Bousquet JA et al., "Circular dichroic investigation of the native and non-native conformational states of the growth factor receptor-binding protein 2 N-terminal src homology domain 3: effect of binding to a proline-rich peptide from guanine nucleotide exchange factor." *Biochemistry* 39, 7722-35 (2000).

Brannetti B et al., "SH3-SPOT: an algorithm to predict preferred ligands to different members of the SH3 gene family." *J Mol Biol* 298(2): 313-28 (2000).
Cherney, BW et al., "cDNA sequence, protein structure, and chromosonal location of the human gene for poly(ADP-ribose) polymerase." *Proc Natl Acad Sci U S A* 84(23): 8370-4 (1987).
Chong S et al., "Single column purification of free recombinant proteins using a self-clevable affinity tag derived from a protein splicing element." *Gene* 192(2):271-81 (Jun. 1997).
Dalgarno DC, Botfield MC & Rickles RJ, "SH3 domains and drug design: lignads, structure, and biological function." *Biopolymers* 43: 383-400 (1997).
de Murcia G & de Murcia JM, "Poly(ADP-ribose) polymerase: a molecular nick-sensor." *Trends Biochem Sci* 19(4): p. 172-6 (1994).
de Murcia JM, et al., "Requirement of poly(ADP-ribose) polymerase in recovery from DNA damage in mice and cells." *Proc Natl Acad Sci U S A* 94(14): 7303-7 (1997).
Decker P et al., "An improved non isotopic test to screen a large series of new inhibitor molecules of poly(ADP-ribose) polymerase activity for therapeutic applications." *Clin Cancer Res*5, 1169-72 (1999).
DeDecker BS et al., "Allosteric drugs: thinking outside the active-site box." *Chem Biol* 7(5): R103-7 (2000).
Deng CX & Brodie SG, "Roles fo BRCA1 and its interacting proteins." *Bioessays* 22(8): 728-37 (2000).
Garbay C et al., "Inhibitors of Ras signal transduction as antimuor agents." *Biochem. Pharmacol*. 60(8): 1165-9 (Oct. 15, 2000).
Gradwohl G et al., "The second zinc-finger domain of poly(ADP-ribose) polymerase determines specificity for single-stranded breaks in DNA." *Proc Natl Acad Sci USA* 87,2990-4 (1990).
Ha HC, et al., "Poly(ADP-ribose) polymers-1 is required for efficient HIV-1 integration." *Proc Natl Acad Sci U S A*. 98(6): 3364-8 (Mar. 13, 2001).

(Continued)

Primary Examiner—John S. Brusca
(74) Attorney, Agent, or Firm—McDermott Will & Emery LLP

(57) ABSTRACT

Poly(ADP-ribose) polymerase-1 (PARP-1) is a central signaling enzyme in a cell nucleus. PARP-1 is a target for the development of radio and chemo sensitizing agents in cancer treatment as well as providing protection from stroke. An SH3 domain and an SH3 ligand domain have now been discovered on the PARP-1 protein. These domains are involved in PARP-1 activation. This discovery makes possible the use of bioinformatics tools for the design of new drugs and strategies for drug target selection, specifically targeting the PARP-1 enzyme.

5 Claims, 6 Drawing Sheets

OTHER PUBLICATIONS

Hansson H et al., "Solution structure of the SH3 domain from Bruton's tyrosine kinase." *Biochemistry* 37(9): 2912-24 (Mar. 3, 1998).

Hansson H et al., "Intermolecular interactions between the SH3 domain and the proline-rich TH region of Bruton's tyrosine kinase." *FEBS Lett.* 489(1): 67-70 (Jan. 26, 2001).

Jacobson MK & Jacobson EL, "Discovering new ADP-ribose polymer cycles: protecting the genome and more." *Trends Biochem Sci.* 24(11): 415-7 (Nov. 1999).

Jagtap P et al., "Novel phenanthridinone inhibitros of poly (adenosine 5'-diphosphate-ribose) synthetase: potent cytoprotective and antishock agents." *Crit. Care Med.* 30(5):1071-82 (May 2002).

Johansson M, "A human poly(ADP-ribose) polymerase gene family (ADPRTL): cDNA cloning of two novel poly(ADP-ribose) polymerase homologues." *Genomics*, 57(3): 442-5 (1999).

Juarez-Salinas H et al., "Simultaneous determination of linear and branched residues in poly(ADP-ribose)." *Anal Biochem* 131(2): 410-8 (1983).

Kardinal C et al., "Rational development of cell-penetrating high affinity SH3 domain binding peptides that selectively disrupt the signal transduction of Crk family adapters." *Ann. NY Acad. Sci*.886: 289-92 (1999).

Kawamura T et al., "An alternative form of poly(ADP-ribose) polymerase in Drosophila melanogaster and its ectopic expression in rat-1 cells." *Biochem Biophys Res Commun* 251(1): 35-40 (1998).

Kickhoefer VA et al., "The 193-kD vault protein, VPARP, is a novel poly(ADP-ribose) polymerase." *J Cell Biol* 146(5): 917-28 (1999).

Kim JW et al., "Inhibition of homodimerization of poly(ADP-ribose) polymerase by its C-terminal cleavage products produced during apoptosis." *J Biol Chem* 275(11): 8121-5 (2000).

Kuriyan J & Cowburn D, "Modular peptide recognition domains in eukaryotic signaling." *Annu Rev Biophys Biomol Struct* 26: 259-88 (1997).

Kurosaki T et al., Primary structrue of human poly(ADP-ribose) synthetase as deduced from cDNA sequence. *J Biol Chem* 262(33): 15990-7 (1987).

Los M et al., "Activation and caspase-mediated inhibition of PARP: A molecular switch between fibroblast necrosis and apoptosis in death receptor signaling." *Molecular Biology of the Cell 1* 3:978-988 (Mar. 2002).

Mabley JG et al., "Inhibition of poly (ADP-ribose) synthetase by gene disruption or inhibition with 5-iodo-6-amino-1,2-benzopyrone protects mice from multiple-low-dose-streptozotocin-induced diabetes." *Br. J. Pharmacol.* 133(6): 909-19 (Jul. 2001).

Macias MJ, Wiesner S & Sudol M, "WW and SH3 domains, two different scaffolds to recognize proline-rich ligands." *FEBS Lett* 513(1): 30-7 (2002).

Marintchev A et al., "Solution structure of the single-strand break repair protein XRCCI N-terminal domain." *Nat Struct Biol* 6(9): 884-93 (1999).

Mendoza-Alvarez H & Alvarez-Gonzalez R, "Poly(ADP-ribose) polymerase is a catalytic dimer and the automodification reaction is intermolecular." *J Biol Chem* 268(30): 22575-80 (1993).

Mosser EA et al., "Physical and functional interactions between the transactivation domain of the hematopoietic transcription factor NF-E2 and WWdomains." *Biochemistry* 37: 13686-95 (1998).

Nguyen JT et al., "Improving SH3 domain ligand selectivity using a non-natural scaffold." *Chem Biol.* 7(7): 463-73 (2000).

Nicholson DW et al., "Identification and Inhibition of the ICE/CED-3 protease necessary for mammalian apoptosis." *Nature* 376(6535): 37-43 (1995).

Perkins E et al., "Novel inhibitors of poly(adp-ribose) polymerase/parp 1 and parp2 identified using a cell-based screen in yeast." *Cancer Res* 61(10): 4175-83 (May 15, 2001).

Pieper A et al., "Poly(ADP-ribosyl)ation basally activated by DNA strand breaks reflects glutamate-nitric oxide neurotransmission." *Proc Natl Acad Sci U S A* 97(4): 1845-50 (Feb. 15, 2000).

Politou AS et al., "The SH3 domain of nebulin binds selectively to type II peptides: theoretical prediction and experimental validation." *J Mol Biol* 316(2): 305-15 (2002).

Rolli V et al., "Random mutagenesis of the poly(ADP-ribose) polymerase catalytic domain reveals amino acids involoved in polymer branching." *Biochemistry* 36: 12147-54 (1997).

Rosen EM et al., "The molecular and cellular basis of radiosensitivity: implications for understanding how normal tissues and tumors respond to therapeutic radiation." *Cancer Invest* 17(1): 56-72 (1999).

Ruf A et al., "Structure of the catalytic fragment of poly(AD-ribose) polymerase from chicken." *Proc Natl Acad Sci U S A* 93(15): 7481-5 (Jul. 1996).

Ruf A, de Murcia G & Schulz G, "Inhibitor and NAD+ binding to poly(ADP-ribose) polymerase as derived from crystal structures and homology modeling." *Biochemsistry* 37(11): 3893-900 (1998).

Schlicker A et al., "4-Amino-1,8-naphthalimide: a novel inhibitor of poly(ADP-ribose) polymerase and radiation sensitizer." *Int J Radiat Biol* 75(1): 91-100 (1999).

Schreiber V et al., "A dominant-negative mutant of human poly(ADP-ribose) polymerase affects cell recovery, apoptosis, and sister chromatid exchange following DNA damage." *Proc Natl Acad Sci U S A* 92: 4753-4757 (May 1995).

Schreiber V et al., "PARP-2 is required for efficient base excision DNA repair in association with PARP-1 and XRCCI." *J Biol Chem*, 277(25): 23028-36 (Jun. 21, 2002).

Shall S & de Murcia G, "Poly(ADP-ribose) polymerase-1: what have we learned from the deficient mouse model?" *Mutat Res* 460(1): 1-15 (2000).

Shieh WM et al., "Poly(ADP-ribose) polymerase null mouse cells synthesize ADP-ribose polymers." *J Biol Chem* 273(46): 30069-72 (1998).

Simbulan-Rosenthal CM et al., "Misregulation of gene expression in primary fibroblasts lacking poly(ADP-ribose) polymerase." *Proc Natl Acad Sci U S A* 97(21): 11274-11279 (Oct. 10, 2000).

Smith S, "The world according to PARP." *Trends Biochem. Sci. 26*: 174-179 (Mar. 2001).

Smith S et al., "Tankyrase, a poly(ADP-ribose) polymerase at human telomeres. *Science* 282(5393): 1484-7 (1998)".

Smulson ME et al., "Roles of poly(ADP-ribosyl)ation and PARP in apoptosis, DNA repair, genomic stability and functions of p53 and E2F-1." *Adv Enzyme Regul* 40: 183-215 (2000).

Stulz CM, White JV, & Smith TF, *Protein Sci.* 2(3): 305-14 (1993).

Szabó C. & Dawson VL, "Role of poly(ADP-ribose) synthetase in inflammation and ischaemia-reperfusion." *Trends Pharmacol Sci* 19(7): 287-98 (1998).

Tentori L, Portarena I & Graziani G, "Potential Clinical applications of poly(ADP-ribose) polymerase (PARP) inhibitors." *Pharmacol Res* 45(2): 73-85 (2002).

Trucco C et al., "A dual approach in the study of poly (ADP-ribose) polymerase: in vitro random mutagenesis and generation of deficient mice." *Mol Cell Biochem* 193(1-2): 53-60 (1999).

Uchida K et al., "of cDNA encoding Drosophila poly(ADP-ribose) polymerase: leucine zipper in the auto-modification domain." *Proc Natl Acad Sci U S A* 90(8): 3481-5 (1993).

Uchida K et al., "Nucleotide sequence of a full-length cDNA for human fibroblast poly(ADP-ribose) polymerase." *Biochem Biophys Res Commun* 148(2): 617-22 (1987).

van Aalten DM et al., "A comparison of structrual and dynamic properties of different simulation methods applied to SH3." *Biophys. J.* 70: 684-692 (Feb. 1996).

Vispë S et al., "A cellular defense pathway regulating transcription through poly(ADP-ribosyl)ation in response to DNA damage." *Proc. Natl. Acad. Sci U S A* 97(18): 9886-9891 (Aug. 29, 2000).

White AW et al., "Resistance-modifying agents. 9.(1) synthesis and biological properties of benzimidazole inhibitors of the DNA repair enzyme Poly(ADP-ribose) polymerase." *J Med Chem* 43: 4084-97 (2000).

Williams, JC, Wierenga RK & Saraste M, "Insights into Src kinase functions: structural comparisons." *Trends Biochem Sci* 23(5): 179-84 (1998).

Wood RD et al., "Human repair genes." *Science* 291: 1284-1289 (Feb. 16, 2001).

* cited by examiner

FIG. 6

SEQUENCE LISTING

<160> NUMBER OF SEQ ID NOS: 48

<210> SEQ ID NO 1
<211> LENGTH: 65
<212> TYPE: PRT
<213> ORGANISM: Homo sapiens

<400> SEQUENCE: 1

Asp Arg Val Ala Asp Gly Met Val Phe Gly Ala Leu Leu Pro Cys Glu
1               5                   10                  15

Glu Cys Ser Gly Gln Leu Val Phe Lys Ser Asp Ala Tyr Tyr Cys Thr
            20                  25                  30

Gly Asp Val Thr Ala Trp Thr Lys Cys Met Val Lys Thr Gln Thr Pro
        35                  40                  45

Asn Arg Lys Glu Trp Val Thr Pro Lys Glu Phe Arg Glu Ile Ser Tyr
    50                  55                  60

Leu
65

<210> SEQ ID NO 2
<211> LENGTH: 4
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid except Pro

<400> SEQUENCE: 2

Pro Xaa Xaa Pro
1

```
<210> SEQ ID NO 3
<211> LENGTH: 3859
<212> TYPE: DNA
<213> ORGANISM: Homo sapiens
<220> FEATURE:
<221> NAME/KEY: CDS
<222> LOCATION: (160)..(3204)

<400> SEQUENCE: 3
aatctatcag ggaacggcgg tgccggtgc ggcgtgttcg gtgcgctctg gccgctcagg      60
ccgtgcggct gggtgagcgc acgcgaggcg gcgaggcggc aagcgtgttt ctaggtcgtg     120
gcgtcgggct tccggagctt tggcggcagc taggggagg atg gcg gag tct tcg       174
                                            Met Ala Glu Ser Ser
                                              1               5 gat aag ctc tat cga gtc gag tac gcc aag agc ggg cgc gcc tct tgc      222
Asp Lys Leu Tyr Arg Val Glu Tyr Ala Lys Ser Gly Arg Ala Ser Cys
                 10                  15                  20 aag aaa tgc agc gag agc atc ccc aag gac tcg ctc cgg atg gcc atc      270
Lys Lys Cys Ser Glu Ser Ile Pro Lys Asp Ser Leu Arg Met Ala Ile
             25                  30                  35 atg gtg cag tcg ccc atg ttt gat gga aaa gtc cca cac tgg tac cac      318
Met Val Gln Ser Pro Met Phe Asp Gly Lys Val Pro His Trp Tyr His
         40                  45                  50 ttc tcc tgc ttc tgg aag gtg ggc cac tcc atc cgg cac cct gac gtt      366
Phe Ser Cys Phe Trp Lys Val Gly His Ser Ile Arg His Pro Asp Val
 55                  60                  65 gag gtg gat ggg ttc tct gag ctt cgg tgg gat gac cag cag aaa gtc      414
Glu Val Asp Gly Phe Ser Glu Leu Arg Trp Asp Asp Gln Gln Lys Val
 70                  75                  80                  85 aag aag aca gcg gaa gct gga gga gtg aca ggc aaa ggc cag gat gga      462
Lys Lys Thr Ala Glu Ala Gly Gly Val Thr Gly Lys Gly Gln Asp Gly
                 90                  95                 100 att ggt agc aag gca gag aag act ctg ggt gac ttt gca gca gag tat      510
Ile Gly Ser Lys Ala Glu Lys Thr Leu Gly Asp Phe Ala Ala Glu Tyr
            105                 110                 115 gcc aag tcc aac aga agt acg tgc aag ggg tgt atg gag aag ata gaa      558
Ala Lys Ser Asn Arg Ser Thr Cys Lys Gly Cys Met Glu Lys Ile Glu
        120                 125                 130 aag ggc cag gtg cgc ctg tcc aag aag atg gtg gac ccg gag aag cca      606
Lys Gly Gln Val Arg Leu Ser Lys Lys Met Val Asp Pro Glu Lys Pro
    135                 140                 145 cag cta ggc atg att gac cgc tgg tac cat cca ggc tgc ttt gtc aag      654
Gln Leu Gly Met Ile Asp Arg Trp Tyr His Pro Gly Cys Phe Val Lys
150                 155                 160                 165 aac agg gag gag ctg ggt ttc cgg ccc gag tac agt gcg agt cag ctc      702
Asn Arg Glu Glu Leu Gly Phe Arg Pro Glu Tyr Ser Ala Ser Gln Leu
                170                 175                 180 aag ggc ttc agc ctc ctt gct aca gag gat aaa gaa gcc ctg aag aag      750
Lys Gly Phe Ser Leu Leu Ala Thr Glu Asp Lys Glu Ala Leu Lys Lys
            185                 190                 195 cag ctc cca gga gtc aag agt gaa gga aag aga aaa ggc gat gag gtg      798
Gln Leu Pro Gly Val Lys Ser Glu Gly Lys Arg Lys Gly Asp Glu Val
        200                 205                 210 gat gga gtg gat gaa gtg gcg aag aag aaa tct aaa aaa gaa aaa gac      846
Asp Gly Val Asp Glu Val Ala Lys Lys Lys Ser Lys Lys Glu Lys Asp
    215                 220                 225 aag gat agt aag ctt gaa aaa gcc cta aag gct cag aac gac ctg atc      894
Lys Asp Ser Lys Leu Glu Lys Ala Leu Lys Ala Gln Asn Asp Leu Ile
230                 235                 240                 245
```

```
                                                -continued tgg aac atc aag gac gag cta aag aaa gtg tgt tca act aat gac ctg        942
Trp Asn Ile Lys Asp Glu Leu Lys Lys Val Cys Ser Thr Asn Asp Leu
            250                 255                 260 aag gag cta ctc atc ttc aac aag cag caa gtg cct tct ggg gag tcg        990
Lys Glu Leu Leu Ile Phe Asn Lys Gln Gln Val Pro Ser Gly Glu Ser
                265                 270                 275 gcg atc ttg gac cga gta gct gat ggc atg gtg ttc ggt gcc ctc ctt       1038
Ala Ile Leu Asp Arg Val Ala Asp Gly Met Val Phe Gly Ala Leu Leu
                    280                 285                 290 ccc tgc gag gaa tgc tcg ggt cag ctg gtc ttc aag agc gat gcc tat       1086
Pro Cys Glu Glu Cys Ser Gly Gln Leu Val Phe Lys Ser Asp Ala Tyr
295                 300                 305 tac tgc act ggg gac gtc act gcc tgg acc aag tgt atg gtc aag aca       1134
Tyr Cys Thr Gly Asp Val Thr Ala Trp Thr Lys Cys Met Val Lys Thr
310                 315                 320                 325 cag aca ccc aac cgg aag gag tgg gta acc cca aag gaa ttc cga gaa       1182
Gln Thr Pro Asn Arg Lys Glu Trp Val Thr Pro Lys Glu Phe Arg Glu
                330                 335                 340 atc tct tac ctc aag aaa ttg aag gtt aaa aag cag gac cgt ata ttc       1230
Ile Ser Tyr Leu Lys Lys Leu Lys Val Lys Lys Gln Asp Arg Ile Phe
                345                 350                 355 ccc cca gaa acc agc gcc tcc gtg gcg gcc acg cct ccg ccc tcc aca       1278
Pro Pro Glu Thr Ser Ala Ser Val Ala Ala Thr Pro Pro Pro Ser Thr
            360                 365                 370 gcc tcg gct cct gct gct gtg aac tcc tct gct tca gca gat aag cca       1326
Ala Ser Ala Pro Ala Ala Val Asn Ser Ser Ala Ser Ala Asp Lys Pro
    375                 380                 385 tta tcc aac atg aag atc ctg act ctc ggg aag ctg tcc cgg aac aag       1374
Leu Ser Asn Met Lys Ile Leu Thr Leu Gly Lys Leu Ser Arg Asn Lys
390                 395                 400                 405 gat gaa gtg aag gcc atg att gag aaa ctc ggg ggg aag ttg acg ggg       1422
Asp Glu Val Lys Ala Met Ile Glu Lys Leu Gly Gly Lys Leu Thr Gly
                410                 415                 420 acg gcc aac aag gct tcc ctg tgc atc agc acc aaa aag gag gtg gaa       1470
Thr Ala Asn Lys Ala Ser Leu Cys Ile Ser Thr Lys Lys Glu Val Glu
                425                 430                 435 aag atg aat aag aag atg gag gaa gta aag gaa gcc aac atc cga gtt       1518
Lys Met Asn Lys Lys Met Glu Glu Val Lys Glu Ala Asn Ile Arg Val
            440                 445                 450 gtg tct gag gac ttc ctc cag gac gtc tcc gcc tcc acc aag agc ctt       1566
Val Ser Glu Asp Phe Leu Gln Asp Val Ser Ala Ser Thr Lys Ser Leu
    455                 460                 465 cag gag ttg ttc tta gcg cac atc ttg tcc cct tgg ggg gca gag gtg       1614
Gln Glu Leu Phe Leu Ala His Ile Leu Ser Pro Trp Gly Ala Glu Val
470                 475                 480                 485 aag gca gag cct gtt gaa gtt gtg gcc cca aga ggg aag tca ggg gct       1662
Lys Ala Glu Pro Val Glu Val Val Ala Pro Arg Gly Lys Ser Gly Ala
                490                 495                 500 gcg ctc tcc aaa aaa agc aag ggc cag gtc aag gag gaa ggt atc aac       1710
Ala Leu Ser Lys Lys Ser Lys Gly Gln Val Lys Glu Glu Gly Ile Asn
                505                 510                 515 aaa tct gaa aag aga atg aaa tta act ctt aaa gga gga gca gct gtg       1758
Lys Ser Glu Lys Arg Met Lys Leu Thr Leu Lys Gly Gly Ala Ala Val
            520                 525                 530 gat cct gat tct gga ctg gaa cac tct gcg cat gtc ctg gag aaa ggt       1806
Asp Pro Asp Ser Gly Leu Glu His Ser Ala His Val Leu Glu Lys Gly
    535                 540                 545 ggg aag gtc ttc agt gcc acc ctt ggc ctg gtg gac atc gtt aaa gga       1854
Gly Lys Val Phe Ser Ala Thr Leu Gly Leu Val Asp Ile Val Lys Gly
550                 555                 560                 565
```

```
acc aac tcc tac tac aag ctg cag ctt ctg gag gac gac aag gaa aac      1902
Thr Asn Ser Tyr Tyr Lys Leu Gln Leu Leu Glu Asp Asp Lys Glu Asn
            570                 575                 580 agg tat tgg ata ttc agg tcc tgg ggc cgt gtg ggt acg gtg atc ggt      1950
Arg Tyr Trp Ile Phe Arg Ser Trp Gly Arg Val Gly Thr Val Ile Gly
            585                 590                 595 agc aac aaa ctg gaa cag atg ccg tcc aag gag gat gcc att gag cag      1998
Ser Asn Lys Leu Glu Gln Met Pro Ser Lys Glu Asp Ala Ile Glu Gln
        600                 605                 610 ttc atg aaa tta tat gaa gaa aaa acc ggg aac gct tgg cac tcc aaa      2046
Phe Met Lys Leu Tyr Glu Glu Lys Thr Gly Asn Ala Trp His Ser Lys
        615                 620                 625 aat ttc acg aag tat ccc aaa aag ttt tac ccc ctg gag att gac tat      2094
Asn Phe Thr Lys Tyr Pro Lys Lys Phe Tyr Pro Leu Glu Ile Asp Tyr
630                 635                 640                 645 ggc cag gat gaa gag gca gtg aag aag ctc aca gta aat cct ggc acc      2142
Gly Gln Asp Glu Glu Ala Val Lys Lys Leu Thr Val Asn Pro Gly Thr
                650                 655                 660 aag tcc aag ctc ccc aag cca gtt cag gac ctc atc aag atg atc ttt      2190
Lys Ser Lys Leu Pro Lys Pro Val Gln Asp Leu Ile Lys Met Ile Phe
            665                 670                 675 gat gtg gaa agt atg aag aaa gcc atg gtg gag tat gag atc gac ctt      2238
Asp Val Glu Ser Met Lys Lys Ala Met Val Glu Tyr Glu Ile Asp Leu
            680                 685                 690 cag aag atg ccc ttg ggg aag ctg agc aaa agg cag atc cag gcc gca      2286
Gln Lys Met Pro Leu Gly Lys Leu Ser Lys Arg Gln Ile Gln Ala Ala
        695                 700                 705 tac tcc atc ctc agt gag gtc cag cag gcg gtg tct cag ggc agc agc      2334
Tyr Ser Ile Leu Ser Glu Val Gln Gln Ala Val Ser Gln Gly Ser Ser
710                 715                 720                 725 gac tct cag atc ctg gat ctc tca aat cgc ttt tac acc ctg atc ccc      2382
Asp Ser Gln Ile Leu Asp Leu Ser Asn Arg Phe Tyr Thr Leu Ile Pro
                730                 735                 740 cac gac ttt ggg atg aag aag cct ccg ctc ctg aac aat gca gac agt      2430
His Asp Phe Gly Met Lys Lys Pro Pro Leu Leu Asn Asn Ala Asp Ser
            745                 750                 755 gtg cag gcc aag gtg gaa atg ctt gac aac ctg ctg gac atc gag gtg      2478
Val Gln Ala Lys Val Glu Met Leu Asp Asn Leu Leu Asp Ile Glu Val
            760                 765                 770 gcc tac agt ctg ctc agg gga ggg tct gat gat agc agc aag gat ccc      2526
Ala Tyr Ser Leu Leu Arg Gly Gly Ser Asp Asp Ser Ser Lys Asp Pro
        775                 780                 785 atc gat gtc aac tat gag aag ctc aaa act gac att aag gtg gtt gac      2574
Ile Asp Val Asn Tyr Glu Lys Leu Lys Thr Asp Ile Lys Val Val Asp
790                 795                 800                 805 aga gat tct gaa gaa gcc gag atc atc agg aag tat gtt aag aac act      2622
Arg Asp Ser Glu Glu Ala Glu Ile Ile Arg Lys Tyr Val Lys Asn Thr
                810                 815                 820 cat gca acc aca cac agt gcg tat gac ttg gaa gtc atc gat atc ttt      2670
His Ala Thr Thr His Ser Ala Tyr Asp Leu Glu Val Ile Asp Ile Phe
            825                 830                 835 aag ata gag cgt gaa ggc gaa tgc cag cgt tac aag ccc ttt aag cag      2718
Lys Ile Glu Arg Glu Gly Glu Cys Gln Arg Tyr Lys Pro Phe Lys Gln
            840                 845                 850 ctt cat aac cga aga ttg ctg tgg cac ggg tcc agg acc acc aac ttt      2766
Leu His Asn Arg Arg Leu Leu Trp His Gly Ser Arg Thr Thr Asn Phe
        855                 860                 865 gct ggg atc ctg tcc cag ggt ctt cgg ata gcc ccg cct gaa gcg ccc      2814
Ala Gly Ile Leu Ser Gln Gly Leu Arg Ile Ala Pro Pro Glu Ala Pro
```

```
                870              875              880              885
gtg aca ggc tac atg ttt ggt aaa ggg atc tat ttc gct gac atg gtc       2862
Val Thr Gly Tyr Met Phe Gly Lys Gly Ile Tyr Phe Ala Asp Met Val
                890              895              900 tcc aag agt gcc aac tac tac cat acg tct cag gga gac cca ata ggc       2910
Ser Lys Ser Ala Asn Tyr Tyr His Thr Ser Gln Gly Asp Pro Ile Gly
            905              910              915 tta atc ctg ttg gga gaa gtt gcc ctt gga aac atg tat gaa ctg aag       2958
Leu Ile Leu Leu Gly Glu Val Ala Leu Gly Asn Met Tyr Glu Leu Lys
        920              925              930 cac gct tca cat atc agc agg tta ccc aag ggc aag cac agt gtc aaa       3006
His Ala Ser His Ile Ser Arg Leu Pro Lys Gly Lys His Ser Val Lys
    935              940              945 ggt ttg ggc aaa act acc cct gat cct tca gct aac att agt ctg gat       3054
Gly Leu Gly Lys Thr Thr Pro Asp Pro Ser Ala Asn Ile Ser Leu Asp
950              955              960              965 ggt gta gac gtt cct ctt ggg acc ggg att tca tct ggt gtg ata gac       3102
Gly Val Asp Val Pro Leu Gly Thr Gly Ile Ser Ser Gly Val Ile Asp
                970              975              980 acc tct cta cta tat aac gag tac att gtc tat gat att gct cag gta       3150
Thr Ser Leu Leu Tyr Asn Glu Tyr Ile Val Tyr Asp Ile Ala Gln Val
            985              990              995 aat ctg aag tat ctg ctg aaa ctg aaa ttc aat ttt aag  acc tcc          3195
Asn Leu Lys Tyr Leu Leu Lys Leu Lys Phe Asn Phe Lys  Thr Ser
        1000             1005             1010 ctg tgg taa ttgggagagg tagccgagtc acacccggtg gctgtggtat               3244
Leu Trp gaattcaccc gaagcgcttc tgcaccaact cacctggccg ctaagttgct gatgggtagt     3304
acctgtacta aaccacctca gaaaggattt tacagaaacg tgttaaaggt tttctctaac     3364
ttctcaagtc ccttgttttg tgttgtgtct gtggggaggg gttgttttgg ggttgttttt     3424
gttttttctt gccaggtaga taaaactgac atagagaaaa ggctggagag agattctgtt     3484
gcatagacta gtcctatgga aaaaccaaa gcttcgttag aatgtctgcc ttactggttt      3544
ccccagggaa ggaaaaatac acttccaccc ttttttctaa gtgttcgtct ttagtttga      3604 ttttggaaag atgttaagca tttattttta gttaaaataa aaactaattt catactattt     3664
agattttctt tttatcttg cacttattgt ccccttttta gttttttttg tttgcctctt      3724
gtggtgaggg gtgtgggaag accaaaggaa ggaacgctaa caatttctca tacttagaaa     3784 caaaagagc tttccttctc caggaatact gaacatggga gctcttgaaa tatgtagtat      3844
taaaagttgc atttg                                                      3859
```

<210> SEQ ID NO 4
<211> LENGTH: 1014
<212> TYPE: PRT
<213> ORGANISM: Homo sapiens

<400> SEQUENCE: 4

```
Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60
```

```
Arg His Pro Asp Val Glu Val Asp Gly Phe Ser Glu Leu Arg Trp Asp
 65                  70                  75                  80

Asp Gln Gln Lys Val Lys Lys Thr Ala Glu Ala Gly Val Thr Gly
             85                  90                  95

Lys Gly Gln Asp Gly Ile Gly Ser Lys Ala Glu Lys Thr Leu Gly Asp
                100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Val Arg Leu Ser Lys Lys Met Val
130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
```

```
                    485                 490                 495
Gly Lys Ser Gly Ala Ala Leu Ser Lys Lys Ser Lys Gly Gln Val Lys
                500                 505                 510
Glu Glu Gly Ile Asn Lys Ser Glu Lys Arg Met Lys Leu Thr Leu Lys
                515                 520                 525
Gly Gly Ala Ala Val Asp Pro Asp Ser Gly Leu Glu His Ser Ala His
                530                 535                 540
Val Leu Glu Lys Gly Gly Lys Val Phe Ser Ala Thr Leu Gly Leu Val
545                 550                 555                 560
Asp Ile Val Lys Gly Thr Asn Ser Tyr Tyr Lys Leu Gln Leu Leu Glu
                565                 570                 575
Asp Asp Lys Glu Asn Arg Tyr Trp Ile Phe Arg Ser Trp Gly Arg Val
                580                 585                 590
Gly Thr Val Ile Gly Ser Asn Lys Leu Glu Gln Met Pro Ser Lys Glu
                595                 600                 605
Asp Ala Ile Glu Gln Phe Met Lys Leu Tyr Glu Lys Thr Gly Asn
                610                 615                 620
Ala Trp His Ser Lys Asn Phe Thr Lys Tyr Pro Lys Lys Phe Tyr Pro
625                 630                 635                 640
Leu Glu Ile Asp Tyr Gly Gln Asp Glu Glu Ala Val Lys Lys Leu Thr
                645                 650                 655
Val Asn Pro Gly Thr Lys Ser Lys Leu Pro Lys Pro Val Gln Asp Leu
                660                 665                 670
Ile Lys Met Ile Phe Asp Val Glu Ser Met Lys Lys Ala Met Val Glu
                675                 680                 685
Tyr Glu Ile Asp Leu Gln Lys Met Pro Leu Gly Lys Leu Ser Lys Arg
                690                 695                 700
Gln Ile Gln Ala Ala Tyr Ser Ile Leu Ser Glu Val Gln Gln Ala Val
705                 710                 715                 720
Ser Gln Gly Ser Ser Asp Ser Gln Ile Leu Asp Leu Ser Asn Arg Phe
                725                 730                 735
Tyr Thr Leu Ile Pro His Asp Phe Gly Met Lys Lys Pro Pro Leu Leu
                740                 745                 750
Asn Asn Ala Asp Ser Val Gln Ala Lys Val Glu Met Leu Asp Asn Leu
                755                 760                 765
Leu Asp Ile Glu Val Ala Tyr Ser Leu Leu Arg Gly Gly Ser Asp Asp
                770                 775                 780
Ser Ser Lys Asp Pro Ile Asp Val Asn Tyr Glu Lys Leu Lys Thr Asp
785                 790                 795                 800
Ile Lys Val Val Asp Arg Asp Ser Glu Glu Ala Glu Ile Ile Arg Lys
                805                 810                 815
Tyr Val Lys Asn Thr His Ala Thr Thr His Ser Ala Tyr Asp Leu Glu
                820                 825                 830
Val Ile Asp Ile Phe Lys Ile Glu Arg Glu Gly Glu Cys Gln Arg Tyr
                835                 840                 845
Lys Pro Phe Lys Gln Leu His Asn Arg Arg Leu Leu Trp His Gly Ser
                850                 855                 860
Arg Thr Thr Asn Phe Ala Gly Ile Leu Ser Gln Gly Leu Arg Ile Ala
865                 870                 875                 880
Pro Pro Glu Ala Pro Val Thr Gly Tyr Met Phe Gly Lys Gly Ile Tyr
                885                 890                 895
Phe Ala Asp Met Val Ser Lys Ser Ala Asn Tyr Tyr His Thr Ser Gln
                900                 905                 910
```

```
Gly Asp Pro Ile Gly Leu Ile Leu Leu Gly Glu Val Ala Leu Gly Asn
        915                 920                 925

Met Tyr Glu Leu Lys His Ala Ser His Ile Ser Arg Leu Pro Lys Gly
        930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Ile Asp Thr Ser Leu Leu Tyr Asn Glu Tyr Ile Val Tyr
            980                 985                 990

Asp Ile Ala Gln Val Asn Leu Lys  Tyr Leu Leu Lys Leu  Lys Phe Asn
        995                 1000                 1005

Phe Lys  Thr Ser Leu Trp
    1010
```

<210> SEQ ID NO 5
<211> LENGTH: 3845
<212> TYPE: DNA
<213> ORGANISM: Mus musculus
<220> FEATURE:
<221> NAME/KEY: CDS
<222> LOCATION: (72)..(3101)

<400> SEQUENCE: 5

```
cacgttagcg gagcgcacca gcggcggcgt cgggctgccg ctgcagcacg agaaggagga      60
tggcggaggc c tcg gag agg ctt tat cga gtg gag tac gcg aag agc ggg     110
             Ser Glu Arg Leu Tyr Arg Val Glu Tyr Ala Lys Ser Gly
              1               5                  10 cgc gcc tct tgc aag aaa tgc agc gag agt att ccc aag gac tcc ctc      158
Arg Ala Ser Cys Lys Lys Cys Ser Glu Ser Ile Pro Lys Asp Ser Leu
         15                  20                  25 cgc atg gcc atc atg gtg cag tca ccc atg ttc gat ggg aaa gtc cca      206
Arg Met Ala Ile Met Val Gln Ser Pro Met Phe Asp Gly Lys Val Pro
 30                  35                  40                  45 cac tgg tac cac ttc tcc tgc ttc tgg aag gtg ggc cac tcc atc cgg      254
His Trp Tyr His Phe Ser Cys Phe Trp Lys Val Gly His Ser Ile Arg
                 50                  55                  60 cag cct gat gtt gag gtg gat ggc ttc tct gag ctg cgc tgg gat gat      302
Gln Pro Asp Val Glu Val Asp Gly Phe Ser Glu Leu Arg Trp Asp Asp
             65                  70                  75 cag cag aag gtc aag aag acg gcc gag gct gga ggc gtg gca ggc aaa      350
Gln Gln Lys Val Lys Lys Thr Ala Glu Ala Gly Gly Val Ala Gly Lys
         80                  85                  90 ggc cag gat gga agt ggc ggc aag gcg gag aag aca ttg ggt gac ttt      398
Gly Gln Asp Gly Ser Gly Gly Lys Ala Glu Lys Thr Leu Gly Asp Phe
     95                 100                 105 tta gcg gag tac gcc aag tcc aac agg agc atg tgc aag ggc tgc ctg      446
Leu Ala Glu Tyr Ala Lys Ser Asn Arg Ser Met Cys Lys Gly Cys Leu
110                 115                 120                 125 gag aag ata gag aag ggc cag atg cgc ctg tcc aag aag atg gtg gat      494
Glu Lys Ile Glu Lys Gly Gln Met Arg Leu Ser Lys Lys Met Val Asp
                130                 135                 140 cca gag aag cca cag ctg ggt atg att gac cgc tgg tac cat cca act      542
Pro Glu Lys Pro Gln Leu Gly Met Ile Asp Arg Trp Tyr His Pro Thr
            145                 150                 155 tgc ttt gtc aag aag cgg gac gag ctg ggc ttc cgg cct gag tac agt      590
Cys Phe Val Lys Lys Arg Asp Glu Leu Gly Phe Arg Pro Glu Tyr Ser
        160                 165                 170
```

```
gcc agt cag ctc aag ggc ttt agc ctc ctc tct gca gaa gac aaa gaa      638
Ala Ser Gln Leu Lys Gly Phe Ser Leu Leu Ser Ala Glu Asp Lys Glu
    175                 180                 185 gct ctg aag aag cag ctc ccg gcc atc aag aat gaa gga aag aga aaa      686
Ala Leu Lys Lys Gln Leu Pro Ala Ile Lys Asn Glu Gly Lys Arg Lys
190                 195                 200                 205 ggt gac gag gtg gat gga aca gat gaa gtg gcc aaa aag aaa tct aag      734
Gly Asp Glu Val Asp Gly Thr Asp Glu Val Ala Lys Lys Lys Ser Lys
                210                 215                 220 aaa ggg aag gac aag gat agt agt aag ctg gag aag gcc ctc aag gct      782
Lys Gly Lys Asp Lys Asp Ser Ser Lys Leu Glu Lys Ala Leu Lys Ala
                225                 230                 235 cag aat gag ctg atc tgg aat atc aaa gac gag ctg aag aaa gcg tgt      830
Gln Asn Glu Leu Ile Trp Asn Ile Lys Asp Glu Leu Lys Lys Ala Cys
    240                 245                 250 tcc acc aac gac ctg aag gag ctg ctc atc ttc aac cag cag cag gtg      878
Ser Thr Asn Asp Leu Lys Glu Leu Leu Ile Phe Asn Gln Gln Gln Val
    255                 260                 265 ccg tca gga gag tca gcg atc ttg gac aga gtt gct gac ggc atg gcg      926
Pro Ser Gly Glu Ser Ala Ile Leu Asp Arg Val Ala Asp Gly Met Ala
270                 275                 280                 285 ttt ggg gcc ctt ctg ccc tgc aag gag tgt tca ggc cag ctg gtc ttt      974
Phe Gly Ala Leu Leu Pro Cys Lys Glu Cys Ser Gly Gln Leu Val Phe
                290                 295                 300 aag agc gac gct tat tac tgt act ggg gat gtc act gcc tgg acc aag     1022
Lys Ser Asp Ala Tyr Tyr Cys Thr Gly Asp Val Thr Ala Trp Thr Lys
                305                 310                 315 tgc atg gtc aag aca cag aat cct agc cga aag gaa tgg gta act cca     1070
Cys Met Val Lys Thr Gln Asn Pro Ser Arg Lys Glu Trp Val Thr Pro
            320                 325                 330 aag gaa ttc cga gaa ata tcc tac ctc aag aag tta aag gtc aaa aaa     1118
Lys Glu Phe Arg Glu Ile Ser Tyr Leu Lys Lys Leu Lys Val Lys Lys
335                 340                 345 cag gac cga ata ttc cct cca gaa agc agc gcc cca gca cca ctg gca     1166
Gln Asp Arg Ile Phe Pro Pro Glu Ser Ser Ala Pro Ala Pro Leu Ala
350                 355                 360                 365 ctg ccc ctc tct gtc acc tca gca ccc aca gct gtg aac tcc tct gct     1214
Leu Pro Leu Ser Val Thr Ser Ala Pro Thr Ala Val Asn Ser Ser Ala
                370                 375                 380 cca gca gac aag ccc ctg tct aac atg aag atc ctg act ctt ggg aag     1262
Pro Ala Asp Lys Pro Leu Ser Asn Met Lys Ile Leu Thr Leu Gly Lys
            385                 390                 395 ctc tcc cag aac aag gac gaa gca aaa gct gtg att gag aaa ctc gga     1310
Leu Ser Gln Asn Lys Asp Glu Ala Lys Ala Val Ile Glu Lys Leu Gly
            400                 405                 410 ggc aag ttg aca gga tct gcc aac aag gcc tcc ttg tgt atc agc act     1358
Gly Lys Leu Thr Gly Ser Ala Asn Lys Ala Ser Leu Cys Ile Ser Thr
    415                 420                 425 aaa aag gag gtg gag aag atg agt aag aag atg gag gaa gtg aaa gcg     1406
Lys Lys Glu Val Glu Lys Met Ser Lys Lys Met Glu Glu Val Lys Ala
430                 435                 440                 445 gcc aac gtt cga gtt gtg tgt gag gac ttc ctc cag gac gtg tct gcc     1454
Ala Asn Val Arg Val Val Cys Glu Asp Phe Leu Gln Asp Val Ser Ala
                450                 455                 460 tcc act aaa agc ctc caa gag ctg ctc tcg gcc cac agc ttg tcc tcg     1502
Ser Thr Lys Ser Leu Gln Glu Leu Leu Ser Ala His Ser Leu Ser Ser
            465                 470                 475 tgg ggg gct gag gtg aag gca gag cct ggt gaa gtg gtg gcc ccc aag     1550
Trp Gly Ala Glu Val Lys Ala Glu Pro Gly Glu Val Val Ala Pro Lys
480                 485                 490
```

-continued

```
ggg aag tca gct gca ccc tcc aag aag agc aag ggt gct gtc aag gag    1598
Gly Lys Ser Ala Ala Pro Ser Lys Lys Ser Lys Gly Ala Val Lys Glu
            495                 500                 505 gaa ggt gtc aac aaa tct gaa aag agg atg aaa tta act ctg aag gga    1646
Glu Gly Val Asn Lys Ser Glu Lys Arg Met Lys Leu Thr Leu Lys Gly
510                 515                 520                 525 gga gca gcc gtt gat cct gac tct ggt ctg gaa cac tct gca cac gtc    1694
Gly Ala Ala Val Asp Pro Asp Ser Gly Leu Glu His Ser Ala His Val
                530                 535                 540 ctg gag aaa ggt ggg aag gtg ttc agc gcc aca ctt ggc ctg gtg gac    1742
Leu Glu Lys Gly Gly Lys Val Phe Ser Ala Thr Leu Gly Leu Val Asp
            545                 550                 555 att gtg aaa ggg acg aac tcc tat tac aaa ctg cag ctt ctg gag gac    1790
Ile Val Lys Gly Thr Asn Ser Tyr Tyr Lys Leu Gln Leu Leu Glu Asp
560                 565                 570 gac aag gag agc agg tac tgg atc ttc cgg tcc tgg ggc cgg gtg ggc    1838
Asp Lys Glu Ser Arg Tyr Trp Ile Phe Arg Ser Trp Gly Arg Val Gly
            575                 580                 585 aca gtt atc ggc agt aac aaa ctt gag cag atg ccc tcc aaa gag gac    1886
Thr Val Ile Gly Ser Asn Lys Leu Glu Gln Met Pro Ser Lys Glu Asp
590                 595                 600                 605 gct gtt gag cac ttc atg aag ctg tat gaa gag aag act ggg aat gcc    1934
Ala Val Glu His Phe Met Lys Leu Tyr Glu Glu Lys Thr Gly Asn Ala
                610                 615                 620 tgg cac tcg aaa aac ttc aca aag tat ccc aag aag ttc tac cct ctg    1982
Trp His Ser Lys Asn Phe Thr Lys Tyr Pro Lys Lys Phe Tyr Pro Leu
            625                 630                 635 gag att gac tat ggc cag gac gaa gag gca gta aag aag ctg acg gtg    2030
Glu Ile Asp Tyr Gly Gln Asp Glu Glu Ala Val Lys Lys Leu Thr Val
640                 645                 650 aag cct ggc acc aag tcg aag ctg ccg aag cca gtg cag gag ctc gtg    2078
Lys Pro Gly Thr Lys Ser Lys Leu Pro Lys Pro Val Gln Glu Leu Val
            655                 660                 665 ggg atg atc ttc gac gtg gag agc atg aaa aag gcc ttg gtg gag tac    2126
Gly Met Ile Phe Asp Val Glu Ser Met Lys Lys Ala Leu Val Glu Tyr
670                 675                 680                 685 gag att gac ctc cag aag atg ccc ttg ggg aag ctg agc aga agg cag    2174
Glu Ile Asp Leu Gln Lys Met Pro Leu Gly Lys Leu Ser Arg Arg Gln
                690                 695                 700 atc cag gcc gcc tac tct atc ctc agc gag gtc cag cag gca gtg tct    2222
Ile Gln Ala Ala Tyr Ser Ile Leu Ser Glu Val Gln Gln Ala Val Ser
            705                 710                 715 caa ggc agc agt gaa tcc cag atc cta gat ctc tcc aat cgc ttc tac    2270
Gln Gly Ser Ser Glu Ser Gln Ile Leu Asp Leu Ser Asn Arg Phe Tyr
720                 725                 730 act ctg atc ccc cat gac ttt gga atg aag aag ccc cca ctc ctg aac    2318
Thr Leu Ile Pro His Asp Phe Gly Met Lys Lys Pro Pro Leu Leu Asn
            735                 740                 745 aac gca gac agc gtg cag gcc aag gtg gag atg cta gac aac ctc ctg    2366
Asn Ala Asp Ser Val Gln Ala Lys Val Glu Met Leu Asp Asn Leu Leu
750                 755                 760                 765 gac atc gag gtg gcc tat agt ctt ctc agg ggt ggc tct gac gac agc    2414
Asp Ile Glu Val Ala Tyr Ser Leu Leu Arg Gly Gly Ser Asp Asp Ser
                770                 775                 780 agc aag gat ccc atc gac gtc aac tac gag aaa ctc aaa act gac att    2462
Ser Lys Asp Pro Ile Asp Val Asn Tyr Glu Lys Leu Lys Thr Asp Ile
            785                 790                 795 aag gtg gtt gac aga gat tct gaa gag gcc gag gtc atc agg aag tac    2510
Lys Val Val Asp Arg Asp Ser Glu Glu Ala Glu Val Ile Arg Lys Tyr
```

```
                800                 805                 810
gtg aag aac act cat gct acc acg cac aac gcc tat gac ctg gaa gtg      2558
Val Lys Asn Thr His Ala Thr Thr His Asn Ala Tyr Asp Leu Glu Val
        815                 820                 825 atc gat atc ttc aag ata gag cgc gag ggg gag agc cag cgc tac aag      2606
Ile Asp Ile Phe Lys Ile Glu Arg Glu Gly Glu Ser Gln Arg Tyr Lys
830                 835                 840                 845 ccc ttc agg cag ctt cac aac cgg agg ctg ctg tgg cac ggc tcc agg      2654
Pro Phe Arg Gln Leu His Asn Arg Arg Leu Leu Trp His Gly Ser Arg
                850                 855                 860 acc acc aac ttt gct ggc atc ctg tcg cag ggt ctg cgg ata gcc cca      2702
Thr Thr Asn Phe Ala Gly Ile Leu Ser Gln Gly Leu Arg Ile Ala Pro
            865                 870                 875 cct gaa gcg cct gtg aca ggc tac atg ttt ggg aaa ggg atc tac ttt      2750
Pro Glu Ala Pro Val Thr Gly Tyr Met Phe Gly Lys Gly Ile Tyr Phe
        880                 885                 890 gcc gac atg gtg tcc aaa agt gca aac tac tgc cac aca tct cag gga      2798
Ala Asp Met Val Ser Lys Ser Ala Asn Tyr Cys His Thr Ser Gln Gly
    895                 900                 905 gac ccg att ggc tta ata ctg ctg gga gag gtt gcc ctt gga aac atg      2846
Asp Pro Ile Gly Leu Ile Leu Leu Gly Glu Val Ala Leu Gly Asn Met
910                 915                 920                 925 tat gaa ctc aag cat gct tca cat atc agc aag tta ccc aag ggc aag      2894
Tyr Glu Leu Lys His Ala Ser His Ile Ser Lys Leu Pro Lys Gly Lys
                930                 935                 940 cac agt gtc aaa ggt ttg gga aaa acc acc cct gac cct tcg gcc agc      2942
His Ser Val Lys Gly Leu Gly Lys Thr Thr Pro Asp Pro Ser Ala Ser
            945                 950                 955 atc acc ctg gag ggt gta gag gtt cca ctg gga aca ggg atc cca tct      2990
Ile Thr Leu Glu Gly Val Glu Val Pro Leu Gly Thr Gly Ile Pro Ser
        960                 965                 970 ggt gtc aac gac acc tgc ctg ctg tat aat gag tac att gtc tac gac      3038
Gly Val Asn Asp Thr Cys Leu Leu Tyr Asn Glu Tyr Ile Val Tyr Asp
    975                 980                 985 att gct cag gtg aat ctc aaa tac ctg ctg aaa ctc aag ttc aat ttt      3086
Ile Ala Gln Val Asn Leu Lys Tyr Leu Leu Lys Leu Lys Phe Asn Phe
990                 995                 1000                1005 aag aca tcc ctg tgg  taaagtgcga ggggtgggct gtgcccagca cccagggcct    3141
Lys Thr Ser Leu Trp
                1010 agggggcaat tctccctagt gcctctgcac cagacaccac aaaacctcag ccatgctgcc    3201 gccgaagggt ggccccctca ccgaatctcc ttaggaaggg ttttatacag acaggttaaa    3261 gggctctggt ttcaagtccc ttgtccatgc tgcactgggg caggccggtt gtttgtggtt    3321 tgtcctacca gccacagctc catagacagc agctggcagt agagcaaaag ttggggagag    3381 gattttgttg tttgcctaga ctagtcctga gggaagaaac accacgtcac agtcacgatg    3441 tctgccttac tggcttcccc agggaaggaa aaatgtgctt cctcccttt ttcaagggtt     3501 catctttgct ttaattttgg caaaatgtta agcatttatt ttgagctaaa aataaaagtt    3561 aatttcatac tatatagatt ttctttttta tcttgtatgt ccccctctta gtctgctgag    3621 cttttgtttt gcttggtttt cagtgataga catgggatag ccaaaagaag ggactacctg    3681 aaaccctaa ctggggcgac tgagcctgta gtgtggtcag ttcaaagttg catttgggat     3741 tctatgtctt ccaaattgaa ccgtctgtaa tcagtacagc cacccaaagg gctatagttc    3801 tcaattaaaa tgcaaatgga tatctaaaaa aaaaaaaaa aaaa                      3845
```

<210> SEQ ID NO 6
<211> LENGTH: 1010
<212> TYPE: PRT
<213> ORGANISM: Mus musculus

<400> SEQUENCE: 6

```
Ser Glu Arg Leu Tyr Arg Val Glu Tyr Ala Lys Ser Gly Arg Ala Ser
1               5                   10                  15

Cys Lys Lys Cys Ser Glu Ser Ile Pro Lys Asp Ser Leu Arg Met Ala
            20                  25                  30

Ile Met Val Gln Ser Pro Met Phe Asp Gly Lys Val Pro His Trp Tyr
        35                  40                  45

His Phe Ser Cys Phe Trp Lys Val Gly His Ser Ile Arg Gln Pro Asp
    50                  55                  60

Val Glu Val Asp Gly Phe Ser Glu Leu Arg Trp Asp Asp Gln Gln Lys
65                  70                  75                  80

Val Lys Lys Thr Ala Glu Ala Gly Val Ala Gly Lys Gly Gln Asp
            85                  90                  95

Gly Ser Gly Gly Lys Ala Glu Lys Thr Leu Gly Asp Phe Leu Ala Glu
            100                 105                 110

Tyr Ala Lys Ser Asn Arg Ser Met Cys Lys Gly Cys Leu Glu Lys Ile
            115                 120                 125

Glu Lys Gly Gln Met Arg Leu Ser Lys Lys Met Val Asp Pro Glu Lys
    130                 135                 140

Pro Gln Leu Gly Met Ile Asp Arg Trp Tyr His Pro Thr Cys Phe Val
145                 150                 155                 160

Lys Lys Arg Asp Glu Leu Gly Phe Arg Pro Glu Tyr Ser Ala Ser Gln
                165                 170                 175

Leu Lys Gly Phe Ser Leu Leu Ser Ala Glu Asp Lys Glu Ala Leu Lys
            180                 185                 190

Lys Gln Leu Pro Ala Ile Lys Asn Glu Gly Lys Arg Lys Gly Asp Glu
        195                 200                 205

Val Asp Gly Thr Asp Glu Val Ala Lys Lys Ser Lys Lys Gly Lys
    210                 215                 220

Asp Lys Asp Ser Ser Lys Leu Glu Lys Ala Leu Lys Ala Gln Asn Glu
225                 230                 235                 240

Leu Ile Trp Asn Ile Lys Asp Glu Leu Lys Lys Ala Cys Ser Thr Asn
                245                 250                 255

Asp Leu Lys Glu Leu Leu Ile Phe Asn Gln Gln Gln Val Pro Ser Gly
            260                 265                 270

Glu Ser Ala Ile Leu Asp Arg Val Ala Asp Gly Met Ala Phe Gly Ala
        275                 280                 285

Leu Leu Pro Cys Lys Glu Cys Ser Gly Gln Leu Val Phe Lys Ser Asp
    290                 295                 300

Ala Tyr Tyr Cys Thr Gly Asp Val Thr Ala Trp Thr Lys Cys Met Val
305                 310                 315                 320

Lys Thr Gln Asn Pro Ser Arg Lys Glu Trp Val Thr Pro Lys Glu Phe
                325                 330                 335

Arg Glu Ile Ser Tyr Leu Lys Lys Leu Lys Val Lys Lys Gln Asp Arg
            340                 345                 350

Ile Phe Pro Pro Glu Ser Ser Ala Pro Ala Pro Leu Ala Leu Pro Leu
        355                 360                 365

Ser Val Thr Ser Ala Pro Thr Ala Val Asn Ser Ser Ala Pro Ala Asp
    370                 375                 380
```

-continued

```
Lys Pro Leu Ser Asn Met Lys Ile Leu Thr Leu Gly Lys Leu Ser Gln
385                 390                 395                 400

Asn Lys Asp Glu Ala Lys Ala Val Ile Glu Lys Leu Gly Gly Lys Leu
            405                 410                 415

Thr Gly Ser Ala Asn Lys Ala Ser Leu Cys Ile Ser Thr Lys Lys Glu
        420                 425                 430

Val Glu Lys Met Ser Lys Lys Met Glu Glu Val Lys Ala Ala Asn Val
    435                 440                 445

Arg Val Val Cys Glu Asp Phe Leu Gln Asp Val Ser Ala Ser Thr Lys
450                 455                 460

Ser Leu Gln Glu Leu Leu Ser Ala His Ser Leu Ser Ser Trp Gly Ala
465                 470                 475                 480

Glu Val Lys Ala Glu Pro Gly Glu Val Val Ala Pro Lys Gly Lys Ser
                485                 490                 495

Ala Ala Pro Ser Lys Lys Ser Lys Gly Ala Val Lys Glu Glu Gly Val
            500                 505                 510

Asn Lys Ser Glu Lys Arg Met Lys Leu Thr Leu Lys Gly Gly Ala Ala
        515                 520                 525

Val Asp Pro Asp Ser Gly Leu Glu His Ser Ala His Val Leu Glu Lys
    530                 535                 540

Gly Gly Lys Val Phe Ser Ala Thr Leu Gly Leu Val Asp Ile Val Lys
545                 550                 555                 560

Gly Thr Asn Ser Tyr Tyr Lys Leu Gln Leu Leu Glu Asp Asp Lys Glu
                565                 570                 575

Ser Arg Tyr Trp Ile Phe Arg Ser Trp Gly Arg Val Gly Thr Val Ile
            580                 585                 590

Gly Ser Asn Lys Leu Glu Gln Met Pro Ser Lys Glu Asp Ala Val Glu
        595                 600                 605

His Phe Met Lys Leu Tyr Glu Glu Lys Thr Gly Asn Ala Trp His Ser
    610                 615                 620

Lys Asn Phe Thr Lys Tyr Pro Lys Lys Phe Tyr Pro Leu Glu Ile Asp
625                 630                 635                 640

Tyr Gly Gln Asp Glu Glu Ala Val Lys Lys Leu Thr Val Lys Pro Gly
                645                 650                 655

Thr Lys Ser Lys Leu Pro Lys Pro Val Gln Glu Leu Val Gly Met Ile
            660                 665                 670

Phe Asp Val Glu Ser Met Lys Lys Ala Leu Val Glu Tyr Glu Ile Asp
        675                 680                 685

Leu Gln Lys Met Pro Leu Gly Lys Leu Ser Arg Arg Gln Ile Gln Ala
    690                 695                 700

Ala Tyr Ser Ile Leu Ser Glu Val Gln Gln Ala Val Ser Gln Gly Ser
705                 710                 715                 720

Ser Glu Ser Gln Ile Leu Asp Leu Ser Asn Arg Phe Tyr Thr Leu Ile
                725                 730                 735

Pro His Asp Phe Gly Met Lys Lys Pro Pro Leu Leu Asn Asn Ala Asp
            740                 745                 750

Ser Val Gln Ala Lys Val Glu Met Leu Asp Asn Leu Leu Asp Ile Glu
        755                 760                 765

Val Ala Tyr Ser Leu Leu Arg Gly Gly Ser Asp Asp Ser Ser Lys Asp
    770                 775                 780

Pro Ile Asp Val Asn Tyr Glu Lys Leu Lys Thr Asp Ile Lys Val Val
785                 790                 795                 800

Asp Arg Asp Ser Glu Glu Ala Glu Val Ile Arg Lys Tyr Val Lys Asn
```

```
                        805                 810                 815
Thr His Ala Thr Thr His Asn Ala Tyr Asp Leu Glu Val Ile Asp Ile
        820                 825                 830
Phe Lys Ile Glu Arg Glu Gly Glu Ser Gln Arg Tyr Lys Pro Phe Arg
            835                 840                 845
Gln Leu His Asn Arg Arg Leu Leu Trp His Gly Ser Arg Thr Thr Asn
    850                 855                 860
Phe Ala Gly Ile Leu Ser Gln Gly Leu Arg Ile Ala Pro Pro Glu Ala
865                 870                 875                 880
Pro Val Thr Gly Tyr Met Phe Gly Lys Gly Ile Tyr Phe Ala Asp Met
                885                 890                 895
Val Ser Lys Ser Ala Asn Tyr Cys His Thr Ser Gln Gly Asp Pro Ile
            900                 905                 910
Gly Leu Ile Leu Leu Gly Glu Val Ala Leu Gly Asn Met Tyr Glu Leu
        915                 920                 925
Lys His Ala Ser His Ile Ser Lys Leu Pro Lys Gly Lys His Ser Val
    930                 935                 940
Lys Gly Leu Gly Lys Thr Thr Pro Asp Pro Ser Ala Ser Ile Thr Leu
945                 950                 955                 960
Glu Gly Val Glu Val Pro Leu Gly Thr Gly Ile Pro Ser Gly Val Asn
                965                 970                 975
Asp Thr Cys Leu Leu Tyr Asn Glu Tyr Ile Val Tyr Asp Ile Ala Gln
            980                 985                 990
Val Asn Leu Lys Tyr Leu Leu Lys  Leu Lys Phe Asn Phe  Lys Thr Ser
        995                 1000                1005
Leu Trp
    1010

<210> SEQ ID NO 7
<211> LENGTH: 9
<212> TYPE: PRT
<213> ORGANISM: Homo sapiens

<400> SEQUENCE: 7

Arg Ile Ala Pro Pro Glu Ala Pro Val
1               5

<210> SEQ ID NO 8
<211> LENGTH: 1910
<212> TYPE: DNA
<213> ORGANISM: Homo sapiens
<220> FEATURE:
<221> NAME/KEY: CDS
<222> LOCATION: (173)..(1777)

<400> SEQUENCE: 8
ctagaattca gcggccgctg aattctaggc ggcgcggcgg cgacggagca ccggcggcgg     60
cagggcgaga gcattaaatg aaagcaaaag agttaataat ggcaacacgg ctccagaaga   120
ctcttcccct gccaagaaaa ctcgtagatg ccagagacag gagtcgaaaa ag atg cct   178
                                                          Met Pro
                                                            1 gtg gct gga gga aaa gct aat aag gac agg aca gaa gac aag caa gat   226
Val Ala Gly Gly Lys Ala Asn Lys Asp Arg Thr Glu Asp Lys Gln Asp
      5                  10                  15 ggt atg cca gga agg tca tgg gcc agc aaa agg gtc tct gaa tct gtg   274
Gly Met Pro Gly Arg Ser Trp Ala Ser Lys Arg Val Ser Glu Ser Val
 20                  25                  30
```

-continued

| | | |
|---|---|---|
| aag gcc ttg ctg tta aag ggc aaa gct cct gtg gac cca gag tgt aca<br>Lys Ala Leu Leu Leu Lys Gly Lys Ala Pro Val Asp Pro Glu Cys Thr<br>35                  40                      45                     50 | 322 |
| gcc aag gtg ggg aag gct cat gtg tat tgt gaa gga aat gat gtc tat<br>Ala Lys Val Gly Lys Ala His Val Tyr Cys Glu Gly Asn Asp Val Tyr<br>55                  60                  65 | 370 |
| gat gtc atg cta aat cag acc aat ctc cag ttc aac aac aac aag tac<br>Asp Val Met Leu Asn Gln Thr Asn Leu Gln Phe Asn Asn Asn Lys Tyr<br>70                  75                  80 | 418 |
| tat ctg att cag cta tta gaa gat gat gcc cag agg aac ttc agt gtt<br>Tyr Leu Ile Gln Leu Leu Glu Asp Asp Ala Gln Arg Asn Phe Ser Val<br>85                  90                  95 | 466 |
| tgg atg aga tgg ggc cga gtt ggg aaa atg gga cag cac agc ctg gtg<br>Trp Met Arg Trp Gly Arg Val Gly Lys Met Gly Gln His Ser Leu Val<br>100               105               110 | 514 |
| gct tgt tca ggc aat ctc aac aag gcc aag gaa atc ttt cag aag aaa<br>Ala Cys Ser Gly Asn Leu Asn Lys Ala Lys Glu Ile Phe Gln Lys Lys<br>115               120               125               130 | 562 |
| ttc ctt gac aaa acg aaa aac aat tgg gaa gat cga gaa aag ttt gag<br>Phe Leu Asp Lys Thr Lys Asn Asn Trp Glu Asp Arg Glu Lys Phe Glu<br>135               140               145 | 610 |
| aag gtg cct gga aaa tat gat atg cta cag atg gac tat gcc acc aat<br>Lys Val Pro Gly Lys Tyr Asp Met Leu Gln Met Asp Tyr Ala Thr Asn<br>150               155               160 | 658 |
| act cag gat gaa gag gaa aca aaa aaa gag gaa tct ctt aaa tct ccc<br>Thr Gln Asp Glu Glu Glu Thr Lys Lys Glu Glu Ser Leu Lys Ser Pro<br>165               170               175 | 706 |
| ttg aag cca gag tca cag cta gat ctt cgg gta cag gag tta ata aag<br>Leu Lys Pro Glu Ser Gln Leu Asp Leu Arg Val Gln Glu Leu Ile Lys<br>180               185               190 | 754 |
| ttg atc tgt aat gtt cag gcc atg gaa gaa atg atg atg gaa atg aag<br>Leu Ile Cys Asn Val Gln Ala Met Glu Glu Met Met Met Glu Met Lys<br>195               200               205               210 | 802 |
| tat aat acc aag aaa gcc cca ctt ggg aag ctg aca gtg gca caa atc<br>Tyr Asn Thr Lys Lys Ala Pro Leu Gly Lys Leu Thr Val Ala Gln Ile<br>215               220               225 | 850 |
| aag gca ggt tac cag tct ctt aag aag att gag gat tgt att cgg gct<br>Lys Ala Gly Tyr Gln Ser Leu Lys Lys Ile Glu Asp Cys Ile Arg Ala<br>230               235               240 | 898 |
| ggc cag cat gga cga gct ctc atg gaa gca tgc aat gaa ttc tac acc<br>Gly Gln His Gly Arg Ala Leu Met Glu Ala Cys Asn Glu Phe Tyr Thr<br>245               250               255 | 946 |
| agg att ccg cat gac ttt gga ctc cgt act cct cca cta atc cgg aca<br>Arg Ile Pro His Asp Phe Gly Leu Arg Thr Pro Pro Leu Ile Arg Thr<br>260               265               270 | 994 |
| cag aag gaa ctg tca gaa aaa ata caa tta cta gag gct ttg gga gac<br>Gln Lys Glu Leu Ser Glu Lys Ile Gln Leu Leu Glu Ala Leu Gly Asp<br>275               280               285               290 | 1042 |
| att gaa att gct att aag ctg gtg aaa aca gag cta caa agc cca gaa<br>Ile Glu Ile Ala Ile Lys Leu Val Lys Thr Glu Leu Gln Ser Pro Glu<br>295               300               305 | 1090 |
| cac cca ttg gac caa cac tat aga aac cta cat tgt gcc ttg cgc ccc<br>His Pro Leu Asp Gln His Tyr Arg Asn Leu His Cys Ala Leu Arg Pro<br>310               315               320 | 1138 |
| ctt gac cat gaa agt tac gag ttc aaa gtg att tcc cag tac cta caa<br>Leu Asp His Glu Ser Tyr Glu Phe Lys Val Ile Ser Gln Tyr Leu Gln<br>325               330               335 | 1186 |
| tct acc cat gct ccc aca cac agc gac tat acc atg acc ttg ctg gat<br>Ser Thr His Ala Pro Thr His Ser Asp Tyr Thr Met Thr Leu Leu Asp<br>340               345               350 | 1234 |

```
ttg ttt gaa gtg gag aag gat ggt gag aaa gaa gcc ttc aga gag gac    1282
Leu Phe Glu Val Glu Lys Asp Gly Glu Lys Glu Ala Phe Arg Glu Asp
355                 360                 365                 370 ctt cat aac agg atg ctt cta tgg cat ggt tcc agg atg agt aac tgg    1330
Leu His Asn Arg Met Leu Leu Trp His Gly Ser Arg Met Ser Asn Trp
            375                 380                 385 gtg gga atc ttg agc cat ggg ctt cga att gcc cac cct gaa gct ccc    1378
Val Gly Ile Leu Ser His Gly Leu Arg Ile Ala His Pro Glu Ala Pro
        390                 395                 400 atc aca ggt tac atg ttt ggg aaa gga atc tac ttt gct gac atg tct    1426
Ile Thr Gly Tyr Met Phe Gly Lys Gly Ile Tyr Phe Ala Asp Met Ser
    405                 410                 415 tcc aag agt gcc aat tac tgc ttt gcc tct cgc cta aag aat aca gga    1474
Ser Lys Ser Ala Asn Tyr Cys Phe Ala Ser Arg Leu Lys Asn Thr Gly
420                 425                 430 ctg ctc ctc tta tca gag gta gct cta ggt cag tgt aat gaa cta cta    1522
Leu Leu Leu Leu Ser Glu Val Ala Leu Gly Gln Cys Asn Glu Leu Leu
435                 440                 445                 450 gag gcc aat cct aag gcc gaa gga ttg ctt caa ggt aaa cat agc acc    1570
Glu Ala Asn Pro Lys Ala Glu Gly Leu Leu Gln Gly Lys His Ser Thr
            455                 460                 465 aag ggg ctg ggc aag atg gct ccc agt tct gcc cac ttc gtc acc ctg    1618
Lys Gly Leu Gly Lys Met Ala Pro Ser Ser Ala His Phe Val Thr Leu
        470                 475                 480 aat ggg agt aca gtg cca tta gga cca gca agt gac aca gga att ctg    1666
Asn Gly Ser Thr Val Pro Leu Gly Pro Ala Ser Asp Thr Gly Ile Leu
    485                 490                 495 aat cca gat ggt tat acc ctc aac tac aat gaa tat att gta tat aac    1714
Asn Pro Asp Gly Tyr Thr Leu Asn Tyr Asn Glu Tyr Ile Val Tyr Asn
500                 505                 510 ccc aac cag gtc cgt atg cgg tac ctt tta aag gtt cag ttt aat ttc    1762
Pro Asn Gln Val Arg Met Arg Tyr Leu Leu Lys Val Gln Phe Asn Phe
515                 520                 525                 530 ctt cag ctg tgg tga atgttgatct aaataaacc agagatctga tcttcaagca    1817
Leu Gln Leu Trp agaaaataag cagtgttgta cttgtgaatt ttgtgatatt ttatgtaata aaaactgtac    1877
aggtctaaaa aaaaaaaaaa aaaaaaaaaa aaa                               1910

<210> SEQ ID NO 9
<211> LENGTH: 534
<212> TYPE: PRT
<213> ORGANISM: Homo sapiens

<400> SEQUENCE: 9

Met Pro Val Ala Gly Gly Lys Ala Asn Lys Asp Arg Thr Glu Asp Lys
1               5                   10                  15

Gln Asp Gly Met Pro Gly Arg Ser Trp Ala Ser Lys Arg Val Ser Glu
            20                  25                  30

Ser Val Lys Ala Leu Leu Lys Gly Lys Ala Pro Val Asp Pro Glu
        35                  40                  45

Cys Thr Ala Lys Val Gly Lys Ala His Val Tyr Cys Glu Gly Asn Asp
    50                  55                  60

Val Tyr Asp Val Met Leu Asn Gln Thr Asn Leu Gln Phe Asn Asn Asn
65                  70                  75                  80

Lys Tyr Tyr Leu Ile Gln Leu Leu Glu Asp Asp Ala Gln Arg Asn Phe
                85                  90                  95

Ser Val Trp Met Arg Trp Gly Arg Val Gly Lys Met Gly Gln His Ser
```

-continued

```
                100                 105                 110
Leu Val Ala Cys Ser Gly Asn Leu Asn Lys Ala Lys Glu Ile Phe Gln
            115                 120                 125
Lys Lys Phe Leu Asp Lys Thr Lys Asn Asn Trp Glu Asp Arg Glu Lys
        130                 135                 140
Phe Glu Lys Val Pro Gly Lys Tyr Asp Met Leu Gln Met Asp Tyr Ala
145                 150                 155                 160
Thr Asn Thr Gln Asp Glu Glu Thr Lys Lys Glu Glu Ser Leu Lys
                165                 170                 175
Ser Pro Leu Lys Pro Glu Ser Gln Leu Asp Leu Arg Val Gln Glu Leu
            180                 185                 190
Ile Lys Leu Ile Cys Asn Val Gln Ala Met Glu Glu Met Met Met Glu
        195                 200                 205
Met Lys Tyr Asn Thr Lys Lys Ala Pro Leu Gly Lys Leu Thr Val Ala
    210                 215                 220
Gln Ile Lys Ala Gly Tyr Gln Ser Leu Lys Lys Ile Glu Asp Cys Ile
225                 230                 235                 240
Arg Ala Gly Gln His Gly Arg Ala Leu Met Glu Ala Cys Asn Glu Phe
                245                 250                 255
Tyr Thr Arg Ile Pro His Asp Phe Gly Leu Arg Thr Pro Pro Leu Ile
            260                 265                 270
Arg Thr Gln Lys Glu Leu Ser Glu Lys Ile Gln Leu Leu Glu Ala Leu
        275                 280                 285
Gly Asp Ile Glu Ile Ala Ile Lys Leu Val Lys Thr Glu Leu Gln Ser
    290                 295                 300
Pro Glu His Pro Leu Asp Gln His Tyr Arg Asn Leu His Cys Ala Leu
305                 310                 315                 320
Arg Pro Leu Asp His Glu Ser Tyr Glu Phe Lys Val Ile Ser Gln Tyr
                325                 330                 335
Leu Gln Ser Thr His Ala Pro Thr His Ser Asp Tyr Thr Met Thr Leu
            340                 345                 350
Leu Asp Leu Phe Glu Val Glu Lys Asp Gly Glu Lys Glu Ala Phe Arg
        355                 360                 365
Glu Asp Leu His Asn Arg Met Leu Leu Trp His Gly Ser Arg Met Ser
    370                 375                 380
Asn Trp Val Gly Ile Leu Ser His Gly Leu Arg Ile Ala His Pro Glu
385                 390                 395                 400
Ala Pro Ile Thr Gly Tyr Met Phe Gly Lys Gly Ile Tyr Phe Ala Asp
                405                 410                 415
Met Ser Ser Lys Ser Ala Asn Tyr Cys Phe Ala Ser Arg Leu Lys Asn
            420                 425                 430
Thr Gly Leu Leu Leu Leu Ser Glu Val Ala Leu Gly Gln Cys Asn Glu
        435                 440                 445
Leu Leu Glu Ala Asn Pro Lys Ala Glu Gly Leu Leu Gln Gly Lys His
    450                 455                 460
Ser Thr Lys Gly Leu Gly Lys Met Ala Pro Ser Ser Ala His Phe Val
465                 470                 475                 480
Thr Leu Asn Gly Ser Thr Val Pro Leu Gly Pro Ala Ser Asp Thr Gly
                485                 490                 495
Ile Leu Asn Pro Asp Gly Tyr Thr Leu Asn Tyr Asn Glu Tyr Ile Val
            500                 505                 510
Tyr Asn Pro Asn Gln Val Arg Met Arg Tyr Leu Leu Lys Val Gln Phe
        515                 520                 525
```

```
Asn Phe Leu Gln Leu Trp
    530

<210> SEQ ID NO 10
<211> LENGTH: 1707
<212> TYPE: DNA
<213> ORGANISM: Mus musculus
<220> FEATURE:
<221> NAME/KEY: CDS
<222> LOCATION: (16)..(1695)

<400> SEQUENCE: 10
ctcgagtcaa gagcg atg gcg ccg cgg cgg cag aga tca ggc tct gga agg        51
              Met Ala Pro Arg Arg Gln Arg Ser Gly Ser Gly Arg
                1               5                  10 cga gtg cta aat gaa gcc aag aaa gtt gat aat ggc aac aaa gca aca          99
Arg Val Leu Asn Glu Ala Lys Lys Val Asp Asn Gly Asn Lys Ala Thr
         15                  20                  25 gaa gac gac tct cct cct ggc aag aag atg cgc acg tgc cag aga aaa        147
Glu Asp Asp Ser Pro Pro Gly Lys Lys Met Arg Thr Cys Gln Arg Lys
     30                  35                  40 ggg cct atg gct gga ggg aag gac gca gac agg aca aaa gac aat cga        195
Gly Pro Met Ala Gly Gly Lys Asp Ala Asp Arg Thr Lys Asp Asn Arg
 45                  50                  55                  60 gac tct gtg aag acc ttg ctg tta aag ggc aaa gcc cct gtg gac cca        243
Asp Ser Val Lys Thr Leu Leu Leu Lys Gly Lys Ala Pro Val Asp Pro
                 65                  70                  75 gag tgt gca gcc aag ctg gga aag gct cat gtg tat tgt gaa gga gat        291
Glu Cys Ala Ala Lys Leu Gly Lys Ala His Val Tyr Cys Glu Gly Asp
             80                  85                  90 gat gtc tat gat gtc atg cta aat caa acc aat ctc cag ttc aac aac        339
Asp Val Tyr Asp Val Met Leu Asn Gln Thr Asn Leu Gln Phe Asn Asn
         95                 100                 105 aac aag tac tac ctt att cag ctg tta gaa gat gat gcc cag agg aac        387
Asn Lys Tyr Tyr Leu Ile Gln Leu Leu Glu Asp Asp Ala Gln Arg Asn
    110                 115                 120 ttc agt gtt tgg atg agg tgg ggc cga gtt gga aag acg ggc cag cac        435
Phe Ser Val Trp Met Arg Trp Gly Arg Val Gly Lys Thr Gly Gln His
125                 130                 135                 140 agc ttg gtg act tgt tct ggt gac ctc aac aaa gca aaa gaa ata ttt        483
Ser Leu Val Thr Cys Ser Gly Asp Leu Asn Lys Ala Lys Glu Ile Phe
                145                 150                 155 cag aaa aaa ttc ctt gac aaa act aaa aac aat tgg gag gac cgt gag        531
Gln Lys Lys Phe Leu Asp Lys Thr Lys Asn Asn Trp Glu Asp Arg Glu
            160                 165                 170 aac ttt gaa aaa gta cct gga aaa tac gac atg tta cag atg gac tat        579
Asn Phe Glu Lys Val Pro Gly Lys Tyr Asp Met Leu Gln Met Asp Tyr
        175                 180                 185 gct gcc agc acg cag gat gaa agt aaa aca aaa gaa gag gaa act ttg        627
Ala Ala Ser Thr Gln Asp Glu Ser Lys Thr Lys Glu Glu Glu Thr Leu
    190                 195                 200 aag cct gag tct cag ctg gat ctt cga gtc cag gag ctg cta aag ttg        675
Lys Pro Glu Ser Gln Leu Asp Leu Arg Val Gln Glu Leu Leu Lys Leu
205                 210                 215                 220 atc tgt aac gtg cag acc atg gaa gaa atg atg att gag atg aag tat        723
Ile Cys Asn Val Gln Thr Met Glu Glu Met Met Ile Glu Met Lys Tyr
                225                 230                 235 gac acc aag aga gcc ccg ctt gga aag ctg aca gtg gcg caa atc aag        771
Asp Thr Lys Arg Ala Pro Leu Gly Lys Leu Thr Val Ala Gln Ile Lys
            240                 245                 250
```

```
gcc ggt tac cag tct ctc aag aag att gag gac tgc atc cgc gct ggc     819
Ala Gly Tyr Gln Ser Leu Lys Lys Ile Glu Asp Cys Ile Arg Ala Gly
        255                 260                 265 cag cat ggg cga gcg ctt gtt gaa gcg tgc aat gaa ttc tac acc agg     867
Gln His Gly Arg Ala Leu Val Glu Ala Cys Asn Glu Phe Tyr Thr Arg
    270                 275                 280 atc cct cat gac ttt gga ctc tcc atc cct cca gta atc cgg aca gag     915
Ile Pro His Asp Phe Gly Leu Ser Ile Pro Pro Val Ile Arg Thr Glu
285                 290                 295                 300 aag gaa ctg tca gac aaa gta aaa ctg cta gag gca ttg gga gac att     963
Lys Glu Leu Ser Asp Lys Val Lys Leu Leu Glu Ala Leu Gly Asp Ile
            305                 310                 315 gaa att gcc ctt aaa ctg gtg aag tca gag cgc caa ggc cta gaa cac    1011
Glu Ile Ala Leu Lys Leu Val Lys Ser Glu Arg Gln Gly Leu Glu His
        320                 325                 330 cca ctg gac caa cac tat aga aac cta cac tgt gct ttg cgt cct ctg    1059
Pro Leu Asp Gln His Tyr Arg Asn Leu His Cys Ala Leu Arg Pro Leu
    335                 340                 345 gac cat gaa agt aat gag ttt aag gtg att tct cag tac cta cag tct    1107
Asp His Glu Ser Asn Glu Phe Lys Val Ile Ser Gln Tyr Leu Gln Ser
350                 355                 360 acg cat gct cct aca cac aag gac tat act atg acc ttg ctg gat gtt    1155
Thr His Ala Pro Thr His Lys Asp Tyr Thr Met Thr Leu Leu Asp Val
365                 370                 375                 380 ttc gaa gta gag aag gaa ggg gag aaa gag gcc ttc agg gag gac ctt    1203
Phe Glu Val Glu Lys Glu Gly Glu Lys Glu Ala Phe Arg Glu Asp Leu
            385                 390                 395 cct aac agg atg ctg ctc tgg cat gga tcc agg ctg agt aac tgg gtg    1251
Pro Asn Arg Met Leu Leu Trp His Gly Ser Arg Leu Ser Asn Trp Val
        400                 405                 410 ggg atc ctg agc cac ggg ctt aga gtt gcc cca cct gag gct ccc atc    1299
Gly Ile Leu Ser His Gly Leu Arg Val Ala Pro Pro Glu Ala Pro Ile
    415                 420                 425 aca ggt tat atg ttt gga aaa gga atc tac ttt gct gac atg tcc tcc    1347
Thr Gly Tyr Met Phe Gly Lys Gly Ile Tyr Phe Ala Asp Met Ser Ser
430                 435                 440 aag agt gcc aat tac tgc ttt gcc tct cgc cta aag aat aca gga ttg    1395
Lys Ser Ala Asn Tyr Cys Phe Ala Ser Arg Leu Lys Asn Thr Gly Leu
445                 450                 455                 460 ctt ctt ctg tca gag gta gct cta ggt cag tgt aat gaa cta ctg gag    1443
Leu Leu Leu Ser Glu Val Ala Leu Gly Gln Cys Asn Glu Leu Leu Glu
            465                 470                 475 gcc aat cct aaa gca caa gga ttg ctt cgg ggc aag cat agc acc aag    1491
Ala Asn Pro Lys Ala Gln Gly Leu Leu Arg Gly Lys His Ser Thr Lys
        480                 485                 490 ggg atg gga aag atg gct ccc agc cct gcc cac ttc atc acc ctg aat    1539
Gly Met Gly Lys Met Ala Pro Ser Pro Ala His Phe Ile Thr Leu Asn
    495                 500                 505 ggg agt aca gtg ccc tta gga cca gca agt gac aca gga att ctc aat    1587
Gly Ser Thr Val Pro Leu Gly Pro Ala Ser Asp Thr Gly Ile Leu Asn
510                 515                 520 cca gag ggg tac acc ctc aac tac aat gag ttt att gtt tat agc ccc    1635
Pro Glu Gly Tyr Thr Leu Asn Tyr Asn Glu Phe Ile Val Tyr Ser Pro
525                 530                 535                 540 aac cag gtc cgt atg cga tac ctt cta aag att caa ttt aac ttc ctg    1683
Asn Gln Val Arg Met Arg Tyr Leu Leu Lys Ile Gln Phe Asn Phe Leu
            545                 550                 555 cag cta tgg tga atgttgctcg ag                                      1707
Gln Leu Trp
```

<210> SEQ ID NO 11
<211> LENGTH: 559
<212> TYPE: PRT
<213> ORGANISM: Mus musculus

<400> SEQUENCE: 11

Met Ala Pro Arg Arg Gln Arg Ser Gly Ser Gly Arg Arg Val Leu Asn
1               5                   10                  15

Glu Ala Lys Lys Val Asp Asn Gly Asn Lys Ala Thr Glu Asp Asp Ser
            20                  25                  30

Pro Pro Gly Lys Lys Met Arg Thr Cys Gln Arg Lys Gly Pro Met Ala
        35                  40                  45

Gly Gly Lys Asp Ala Asp Arg Thr Lys Asp Asn Arg Asp Ser Val Lys
    50                  55                  60

Thr Leu Leu Lys Gly Lys Ala Pro Val Asp Pro Glu Cys Ala Ala
65                  70                  75                  80

Lys Leu Gly Lys Ala His Val Tyr Cys Glu Gly Asp Asp Val Tyr Asp
                85                  90                  95

Val Met Leu Asn Gln Thr Asn Leu Gln Phe Asn Asn Asn Lys Tyr Tyr
            100                 105                 110

Leu Ile Gln Leu Leu Glu Asp Ala Gln Arg Asn Phe Ser Val Trp
            115                 120                 125

Met Arg Trp Gly Arg Val Gly Lys Thr Gly Gln His Ser Leu Val Thr
    130                 135                 140

Cys Ser Gly Asp Leu Asn Lys Ala Lys Glu Ile Phe Gln Lys Phe
145                 150                 155                 160

Leu Asp Lys Thr Lys Asn Asn Trp Glu Asp Arg Glu Asn Phe Glu Lys
                165                 170                 175

Val Pro Gly Lys Tyr Asp Met Leu Gln Met Asp Tyr Ala Ala Ser Thr
            180                 185                 190

Gln Asp Glu Ser Lys Thr Lys Glu Glu Thr Leu Lys Pro Glu Ser
            195                 200                 205

Gln Leu Asp Leu Arg Val Gln Glu Leu Leu Lys Leu Ile Cys Asn Val
    210                 215                 220

Gln Thr Met Glu Glu Met Met Ile Glu Met Lys Tyr Asp Thr Lys Arg
225                 230                 235                 240

Ala Pro Leu Gly Lys Leu Thr Val Ala Gln Ile Lys Ala Gly Tyr Gln
                245                 250                 255

Ser Leu Lys Lys Ile Glu Asp Cys Ile Arg Ala Gly Gln His Gly Arg
            260                 265                 270

Ala Leu Val Glu Ala Cys Asn Glu Phe Tyr Thr Arg Ile Pro His Asp
    275                 280                 285

Phe Gly Leu Ser Ile Pro Pro Val Ile Arg Thr Glu Lys Glu Leu Ser
290                 295                 300

Asp Lys Val Lys Leu Leu Glu Ala Leu Gly Asp Ile Glu Ile Ala Leu
305                 310                 315                 320

Lys Leu Val Lys Ser Glu Arg Gln Gly Leu Glu His Pro Leu Asp Gln
                325                 330                 335

His Tyr Arg Asn Leu His Cys Ala Leu Arg Pro Leu Asp His Glu Ser
            340                 345                 350

Asn Glu Phe Lys Val Ile Ser Gln Tyr Leu Gln Ser Thr His Ala Pro
        355                 360                 365

Thr His Lys Asp Tyr Thr Met Thr Leu Leu Asp Val Phe Glu Val Glu
    370                 375                 380

-continued

```
Lys Glu Gly Glu Lys Glu Ala Phe Arg Glu Asp Leu Pro Asn Arg Met
385                 390                 395                 400

Leu Leu Trp His Gly Ser Arg Leu Ser Asn Trp Val Gly Ile Leu Ser
            405                 410                 415

His Gly Leu Arg Val Ala Pro Pro Glu Ala Pro Ile Thr Gly Tyr Met
        420                 425                 430

Phe Gly Lys Gly Ile Tyr Phe Ala Asp Met Ser Ser Lys Ser Ala Asn
            435                 440                 445

Tyr Cys Phe Ala Ser Arg Leu Lys Asn Thr Gly Leu Leu Leu Leu Ser
450                 455                 460

Glu Val Ala Leu Gly Gln Cys Asn Glu Leu Leu Glu Ala Asn Pro Lys
465                 470                 475                 480

Ala Gln Gly Leu Leu Arg Gly Lys His Ser Thr Lys Gly Met Gly Lys
                485                 490                 495

Met Ala Pro Ser Pro Ala His Phe Ile Thr Leu Asn Gly Ser Thr Val
            500                 505                 510

Pro Leu Gly Pro Ala Ser Asp Thr Gly Ile Leu Asn Pro Glu Gly Tyr
        515                 520                 525

Thr Leu Asn Tyr Asn Glu Phe Ile Val Tyr Ser Pro Asn Gln Val Arg
530                 535                 540

Met Arg Tyr Leu Leu Lys Ile Gln Phe Asn Phe Leu Gln Leu Trp
545                 550                 555

<210> SEQ ID NO 12
<211> LENGTH: 1880
<212> TYPE: DNA
<213> ORGANISM: Homo sapiens
<220> FEATURE:
<221> NAME/KEY: CDS
<222> LOCATION: (131)..(1732)

<400> SEQUENCE: 12
attctctccc taattcacgc ctgaggctca tggagagttg ctagacctgg gactgccctg      60
ggaggcgcac acaaccaggc cgggtggcag ccaggacctc tcccatgtcc ctgcttttct     120
tgggacagcc atg gct cca aag ccg aag ccc tgg gta cag act gag ggc        169
            Met Ala Pro Lys Pro Lys Pro Trp Val Gln Thr Glu Gly
              1               5                  10 cct gag aag aag aag ggc cgg cag gca gga agg gag gag gac ccc ttc       217
Pro Glu Lys Lys Lys Gly Arg Gln Ala Gly Arg Glu Glu Asp Pro Phe
     15                  20                  25 cgc tcc acc gct gag gcc ctc aag gcc ata ccc gca gag aag cgc ata       265
Arg Ser Thr Ala Glu Ala Leu Lys Ala Ile Pro Ala Glu Lys Arg Ile
 30                  35                  40                  45 atc cgc gtg gat cca aca tgt cca ctc agc agc aac ccc ggg acc cag       313
Ile Arg Val Asp Pro Thr Cys Pro Leu Ser Ser Asn Pro Gly Thr Gln
                 50                  55                  60 gtg tat gag gac tac aac tgc acc ctg aac cag acc aac atc gag aac       361
Val Tyr Glu Asp Tyr Asn Cys Thr Leu Asn Gln Thr Asn Ile Glu Asn
             65                  70                  75 aac aac aag aag ttc tac atc atc cag ctg ctc caa gac agc aac cgc       409
Asn Asn Lys Lys Phe Tyr Ile Ile Gln Leu Leu Gln Asp Ser Asn Arg
         80                  85                  90 ttc ttc acc tgc tgg aac cgc tgg ggc cgt gtg gga gag gtc ggc cag       457
Phe Phe Thr Cys Trp Asn Arg Trp Gly Arg Val Gly Glu Val Gly Gln
     95                 100                 105 tca aag atc aac cac ttc aca agg cta gaa gat gca aag aag gac ttt       505
Ser Lys Ile Asn His Phe Thr Arg Leu Glu Asp Ala Lys Lys Asp Phe
```

-continued

| | | | | | | | | | | | | | | | | |
|---|---|---|---|---|---|---|---|---|---|---|---|---|---|---|---|---|
| | | 110 | | | | 115 | | | | 120 | | | | 125 | | |
| gag | aag | aaa | ttt | cgg | gaa | aag | acc | aag | aac | aac | tgg | gca | gag | cgg | gac | 553 |
| Glu | Lys | Lys | Phe | Arg | Glu | Lys | Thr | Lys | Asn | Asn | Trp | Ala | Glu | Arg | Asp | |
| | | | | 130 | | | | | 135 | | | | | 140 | | |
| cac | ttt | gtg | tct | cac | ccg | ggc | aag | tac | aca | ctt | atc | gaa | gta | cag | gca | 601 |
| His | Phe | Val | Ser | His | Pro | Gly | Lys | Tyr | Thr | Leu | Ile | Glu | Val | Gln | Ala | |
| | | | | 145 | | | | | 150 | | | | | 155 | | |
| gag | gat | gag | gcc | cag | gaa | gct | gtg | gtg | aag | gtg | gac | aga | gcc | cca | gtg | 649 |
| Glu | Asp | Glu | Ala | Gln | Glu | Ala | Val | Val | Lys | Val | Asp | Arg | Ala | Pro | Val | |
| | | | | 160 | | | | | 165 | | | | | 170 | | |
| agg | act | gtg | act | aag | cgg | gtg | cag | ccc | tgc | tcc | ctg | gac | cca | gcc | acg | 697 |
| Arg | Thr | Val | Thr | Lys | Arg | Val | Gln | Pro | Cys | Ser | Leu | Asp | Pro | Ala | Thr | |
| | | | | 175 | | | | | 180 | | | | | 185 | | |
| cag | aag | ctc | atc | act | aac | atc | ttc | agc | aag | gag | atg | ttc | aag | aac | acc | 745 |
| Gln | Lys | Leu | Ile | Thr | Asn | Ile | Phe | Ser | Lys | Glu | Met | Phe | Lys | Asn | Thr | |
| | | | | 190 | | | | | 195 | | | | | 200 | | 205 |
| atg | gcc | ctc | atg | gac | ctg | gat | gtg | aag | aag | atg | ccc | ctg | gga | aag | ctg | 793 |
| Met | Ala | Leu | Met | Asp | Leu | Asp | Val | Lys | Lys | Met | Pro | Leu | Gly | Lys | Leu | |
| | | | | | | | | 210 | | | | | 215 | | | 220 |
| agc | aag | caa | cag | att | gca | cgg | ggt | ttc | gag | gcc | ttg | gag | gcg | ctg | gag | 841 |
| Ser | Lys | Gln | Gln | Ile | Ala | Arg | Gly | Phe | Glu | Ala | Leu | Glu | Ala | Leu | Glu | |
| | | | | | | | | 225 | | | | | 230 | | | 235 |
| gag | gcc | ctg | aaa | ggc | ccc | acg | gat | ggt | ggc | caa | agc | ctg | gag | gag | ctg | 889 |
| Glu | Ala | Leu | Lys | Gly | Pro | Thr | Asp | Gly | Gly | Gln | Ser | Leu | Glu | Glu | Leu | |
| | | | | | | | | 240 | | | | | 245 | | | 250 |
| tcc | tca | cac | ttt | tac | acc | gtc | atc | ccg | cac | aac | ttc | ggc | cac | agc | cag | 937 |
| Ser | Ser | His | Phe | Tyr | Thr | Val | Ile | Pro | His | Asn | Phe | Gly | His | Ser | Gln | |
| | | | | | | | | 255 | | | | | 260 | | | 265 |
| ccc | ccg | ccc | atc | aat | tcc | cct | gag | ctt | ctg | cag | gcc | aag | aag | gac | atg | 985 |
| Pro | Pro | Pro | Ile | Asn | Ser | Pro | Glu | Leu | Leu | Gln | Ala | Lys | Lys | Asp | Met | |
| 270 | | | | | 275 | | | | | 280 | | | | | 285 | |
| ctg | ctg | gtg | ctg | gcg | gac | atc | gag | ctg | gcc | cag | gcc | ctg | cag | gca | gtc | 1033 |
| Leu | Leu | Val | Leu | Ala | Asp | Ile | Glu | Leu | Ala | Gln | Ala | Leu | Gln | Ala | Val | |
| | | | | 290 | | | | | 295 | | | | | 300 | | |
| tct | gag | cag | gag | aag | acg | gtg | gag | gag | gtg | cca | cac | ccc | ctg | gac | cga | 1081 |
| Ser | Glu | Gln | Glu | Lys | Thr | Val | Glu | Glu | Val | Pro | His | Pro | Leu | Asp | Arg | |
| | | | | 305 | | | | | 310 | | | | | 315 | | |
| gac | tac | cag | ctt | ctc | aag | tgc | cag | ctg | cag | ctg | cta | gac | tct | gga | gca | 1129 |
| Asp | Tyr | Gln | Leu | Leu | Lys | Cys | Gln | Leu | Gln | Leu | Leu | Asp | Ser | Gly | Ala | |
| | | | | 320 | | | | | 325 | | | | | 330 | | |
| cct | gag | tac | aag | gtg | ata | cag | acc | tac | tta | gaa | cag | act | ggc | agc | aac | 1177 |
| Pro | Glu | Tyr | Lys | Val | Ile | Gln | Thr | Tyr | Leu | Glu | Gln | Thr | Gly | Ser | Asn | |
| | 335 | | | | | 340 | | | | | 345 | | | | | |
| cac | agg | tgc | cct | aca | ctt | caa | cac | atc | tgg | aaa | gta | aac | caa | gaa | ggg | 1225 |
| His | Arg | Cys | Pro | Thr | Leu | Gln | His | Ile | Trp | Lys | Val | Asn | Gln | Glu | Gly | |
| 350 | | | | | 355 | | | | | 360 | | | | | 365 | |
| gag | gaa | gac | aga | ttc | cag | gcc | cac | tcc | aaa | ctg | ggt | aat | cgg | aag | ctg | 1273 |
| Glu | Glu | Asp | Arg | Phe | Gln | Ala | His | Ser | Lys | Leu | Gly | Asn | Arg | Lys | Leu | |
| | | | | 370 | | | | | 375 | | | | | 380 | | |
| ctg | tgg | cat | ggc | acc | aac | atg | gcc | gtg | gtg | gcc | gcc | atc | ctc | act | agt | 1321 |
| Leu | Trp | His | Gly | Thr | Asn | Met | Ala | Val | Val | Ala | Ala | Ile | Leu | Thr | Ser | |
| | | | | 385 | | | | | 390 | | | | | 395 | | |
| ggg | ctc | cgc | atc | atg | cca | cat | tct | ggt | ggg | cgt | gtt | ggc | aag | ggc | atc | 1369 |
| Gly | Leu | Arg | Ile | Met | Pro | His | Ser | Gly | Gly | Arg | Val | Gly | Lys | Gly | Ile | |
| | | | | 400 | | | | | 405 | | | | | 410 | | |
| tac | ttt | gcc | tca | gag | aac | agc | aag | tca | gct | gga | tat | gtt | att | ggc | atg | 1417 |
| Tyr | Phe | Ala | Ser | Glu | Asn | Ser | Lys | Ser | Ala | Gly | Tyr | Val | Ile | Gly | Met | |
| | | | | 415 | | | | | 420 | | | | | 425 | | |
| aag | tgt | ggg | gcc | cac | cat | gtc | ggc | tac | atg | ttc | ctg | ggt | gag | gtg | gcc | 1465 |

```
Lys Cys Gly Ala His His Val Gly Tyr Met Phe Leu Gly Glu Val Ala
430                 435                 440                 445 ctg ggc aga gag cac cat atc aac acg gac aac ccc agc ttg aag agc     1513
Leu Gly Arg Glu His His Ile Asn Thr Asp Asn Pro Ser Leu Lys Ser
                    450                 455                 460 cca cct cct ggc ttc gac agt gtc att gcc cga ggc cac acc gag cct     1561
Pro Pro Pro Gly Phe Asp Ser Val Ile Ala Arg Gly His Thr Glu Pro
                465                 470                 475 gat ccg acc cag gac act gag ttg gag ctg gat ggc cag caa gtg gtg     1609
Asp Pro Thr Gln Asp Thr Glu Leu Glu Leu Asp Gly Gln Gln Val Val
            480                 485                 490 gtg ccc cag ggc cag cct gtg ccc tgc cca gag ttc agc agc tcc aca     1657
Val Pro Gln Gly Gln Pro Val Pro Cys Pro Glu Phe Ser Ser Ser Thr
        495                 500                 505 ttc tcc cag agc gag tac ctc atc tac cag gag agc cag tgt cgc ctg     1705
Phe Ser Gln Ser Glu Tyr Leu Ile Tyr Gln Glu Ser Gln Cys Arg Leu
510                 515                 520                 525 cgc tac ctg ctg gag gtc cac ctc tga gtgcccgccc tgtccccgg            1752
Arg Tyr Leu Leu Glu Val His Leu
                530 ggtcctgcaa ggctggactg tgatcttcaa tcatcctgcc catctctggt accctatat    1812 cactcctttt tttcaagaat acaatacgtt gttgttaact ataaaaaaaa aaaaaaaaa    1872 aaaaaaaa                                                            1880

<210> SEQ ID NO 13
<211> LENGTH: 533
<212> TYPE: PRT
<213> ORGANISM: Homo sapiens

<400> SEQUENCE: 13

Met Ala Pro Lys Pro Lys Pro Trp Val Gln Thr Glu Gly Pro Glu Lys
1               5                   10                  15

Lys Lys Gly Arg Gln Ala Gly Arg Glu Glu Asp Pro Phe Arg Ser Thr
                20                  25                  30

Ala Glu Ala Leu Lys Ala Ile Pro Ala Glu Lys Arg Ile Ile Arg Val
            35                  40                  45

Asp Pro Thr Cys Pro Leu Ser Ser Asn Pro Gly Thr Gln Val Tyr Glu
        50                  55                  60

Asp Tyr Asn Cys Thr Leu Asn Gln Thr Asn Ile Glu Asn Asn Asn Lys
65                  70                  75                  80

Lys Phe Tyr Ile Ile Gln Leu Leu Gln Asp Ser Asn Arg Phe Phe Thr
                85                  90                  95

Cys Trp Asn Arg Trp Gly Arg Val Gly Glu Val Gly Gln Ser Lys Ile
                100                 105                 110

Asn His Phe Thr Arg Leu Glu Asp Ala Lys Lys Asp Phe Glu Lys Lys
            115                 120                 125

Phe Arg Glu Lys Thr Lys Asn Asn Trp Ala Glu Arg Asp His Phe Val
        130                 135                 140

Ser His Pro Gly Lys Tyr Thr Leu Ile Glu Val Gln Ala Glu Asp Glu
145                 150                 155                 160

Ala Gln Glu Ala Val Val Lys Val Asp Arg Ala Pro Val Arg Thr Val
                165                 170                 175

Thr Lys Arg Val Gln Pro Cys Ser Leu Asp Pro Ala Thr Gln Lys Leu
            180                 185                 190

Ile Thr Asn Ile Phe Ser Lys Glu Met Phe Lys Asn Thr Met Ala Leu
        195                 200                 205
```

```
Met Asp Leu Asp Val Lys Lys Met Pro Leu Gly Lys Leu Ser Lys Gln
    210                 215                 220

Gln Ile Ala Arg Gly Phe Glu Ala Leu Glu Ala Leu Glu Glu Ala Leu
225                 230                 235                 240

Lys Gly Pro Thr Asp Gly Gly Gln Ser Leu Glu Leu Ser His
                245                 250                 255

Phe Tyr Thr Val Ile Pro His Asn Phe Gly His Ser Gln Pro Pro Pro
                260                 265                 270

Ile Asn Ser Pro Glu Leu Leu Gln Ala Lys Lys Asp Met Leu Leu Val
            275                 280                 285

Leu Ala Asp Ile Glu Leu Ala Gln Ala Leu Gln Ala Val Ser Glu Gln
        290                 295                 300

Glu Lys Thr Val Glu Glu Val Pro His Pro Leu Asp Arg Asp Tyr Gln
305                 310                 315                 320

Leu Leu Lys Cys Gln Leu Gln Leu Leu Asp Ser Gly Ala Pro Glu Tyr
                325                 330                 335

Lys Val Ile Gln Thr Tyr Leu Glu Gln Thr Gly Ser Asn His Arg Cys
                340                 345                 350

Pro Thr Leu Gln His Ile Trp Lys Val Asn Gln Glu Gly Glu Glu Asp
            355                 360                 365

Arg Phe Gln Ala His Ser Lys Leu Gly Asn Arg Lys Leu Leu Trp His
370                 375                 380

Gly Thr Asn Met Ala Val Val Ala Ala Ile Leu Thr Ser Gly Leu Arg
385                 390                 395                 400

Ile Met Pro His Ser Gly Gly Arg Val Gly Lys Gly Ile Tyr Phe Ala
                405                 410                 415

Ser Glu Asn Ser Lys Ser Ala Gly Tyr Val Ile Gly Met Lys Cys Gly
            420                 425                 430

Ala His His Val Gly Tyr Met Phe Leu Gly Glu Val Ala Leu Gly Arg
        435                 440                 445

Glu His His Ile Asn Thr Asp Asn Pro Ser Leu Lys Ser Pro Pro Pro
    450                 455                 460

Gly Phe Asp Ser Val Ile Ala Arg Gly His Thr Glu Pro Asp Pro Thr
465                 470                 475                 480

Gln Asp Thr Glu Leu Glu Leu Asp Gly Gln Val Val Val Pro Gln
                485                 490                 495

Gly Gln Pro Val Pro Cys Pro Glu Phe Ser Ser Ser Thr Phe Ser Gln
                500                 505                 510

Ser Glu Tyr Leu Ile Tyr Gln Glu Ser Gln Cys Arg Leu Arg Tyr Leu
            515                 520                 525

Leu Glu Val His Leu
    530

<210> SEQ ID NO 14
<211> LENGTH: 5778
<212> TYPE: DNA
<213> ORGANISM: Homo sapiens
<220> FEATURE:
<221> NAME/KEY: CDS
<222> LOCATION: (1)..(3501)

<400> SEQUENCE: 14 atg tcg ggt cgc cgc tgc gcc ggc ggg gga gcg gcc tgc gcg agc gcc    48
Met Ser Gly Arg Arg Cys Ala Gly Gly Gly Ala Ala Cys Ala Ser Ala
1               5                   10                  15
```

-continued

| | | |
|---|---|---|
| gcg gcc gag gcc gtg gag ccg gcc gcc cga gag ctg ttc gag gcg tgc<br>Ala Ala Glu Ala Val Glu Pro Ala Ala Arg Glu Leu Phe Glu Ala Cys<br>                20                 25               30 | 96 |
| cgc aac ggg gac gtg gaa cga gtc aag agg ctg gtg acg cct gag aag<br>Arg Asn Gly Asp Val Glu Arg Val Lys Arg Leu Val Thr Pro Glu Lys<br>      35                40                45 | 144 |
| gtg aac agc cgc gac acg gcg ggc agg aaa tcc acc ccg ctg cac ttc<br>Val Asn Ser Arg Asp Thr Ala Gly Arg Lys Ser Thr Pro Leu His Phe<br>50                   55                60 | 192 |
| gcc gca ggt ttt ggg cgg aaa gac gta gtt gaa tat ttg ctt cag aat<br>Ala Ala Gly Phe Gly Arg Lys Asp Val Val Glu Tyr Leu Leu Gln Asn<br>65                 70                75                80 | 240 |
| ggt gca aat gtc caa gca cgt gat gat ggg ggc ctt att cct ctt cat<br>Gly Ala Asn Val Gln Ala Arg Asp Asp Gly Gly Leu Ile Pro Leu His<br>                85                 90                95 | 288 |
| aat gca tgc tct ttt ggt cat gct gaa gta gtc aat ctc ctt ttg cga<br>Asn Ala Cys Ser Phe Gly His Ala Glu Val Val Asn Leu Leu Leu Arg<br>                   100               105             110 | 336 |
| cat ggt gca gac ccc aat gct cga gat aat tgg aat tat act cct ctc<br>His Gly Ala Asp Pro Asn Ala Arg Asp Asn Trp Asn Tyr Thr Pro Leu<br>            115               120              125 | 384 |
| cat gaa gct gca att aaa gga aag att gat gtt tgc att gtg ctg tta<br>His Glu Ala Ala Ile Lys Gly Lys Ile Asp Val Cys Ile Val Leu Leu<br>130                 135               140 | 432 |
| cag cat gga gct gag cca acc atc cga aat aca gat gga agg aca gca<br>Gln His Gly Ala Glu Pro Thr Ile Arg Asn Thr Asp Gly Arg Thr Ala<br>145                 150               155              160 | 480 |
| ttg gat tta gca gat cca tct gcc aaa gca gtg ctt act ggt gaa tat<br>Leu Asp Leu Ala Asp Pro Ser Ala Lys Ala Val Leu Thr Gly Glu Tyr<br>                  165               170              175 | 528 |
| aag aaa gat gaa ctc tta gaa agt gcc agg agt ggc aat gaa gaa aaa<br>Lys Lys Asp Glu Leu Leu Glu Ser Ala Arg Ser Gly Asn Glu Glu Lys<br>         180                185              190 | 576 |
| atg atg gct cta ctc aca cca tta aat gtc aac tgc cac gca agt gat<br>Met Met Ala Leu Leu Thr Pro Leu Asn Val Asn Cys His Ala Ser Asp<br>             195               200             205 | 624 |
| ggc aga aag tca act cca tta cat ttg gca gca gga tat aac aga gta<br>Gly Arg Lys Ser Thr Pro Leu His Leu Ala Ala Gly Tyr Asn Arg Val<br>210               215               220 | 672 |
| aag att gta cag ctg tta ctg caa cat gga gct gat gtc cat gct aaa<br>Lys Ile Val Gln Leu Leu Leu Gln His Gly Ala Asp Val His Ala Lys<br>225               230              235              240 | 720 |
| gat aaa ggt gat ctg gta cca tta cac aat gcc tgt tct tat ggt cat<br>Asp Lys Gly Asp Leu Val Pro Leu His Asn Ala Cys Ser Tyr Gly His<br>                  245               250              255 | 768 |
| tat gaa gta act gaa ctt ttg gtc aag cat ggt gcc tgt gta aat gca<br>Tyr Glu Val Thr Glu Leu Leu Val Lys His Gly Ala Cys Val Asn Ala<br>             260               265             270 | 816 |
| atg gac ttg tgg caa ttc act cct ctt cat gag gca gct tct aag aac<br>Met Asp Leu Trp Gln Phe Thr Pro Leu His Glu Ala Ala Ser Lys Asn<br>         275               280              285 | 864 |
| agg gtt gaa gta tgt tct ctt ctc tta agt tat ggt gca gac cca aca<br>Arg Val Glu Val Cys Ser Leu Leu Leu Ser Tyr Gly Ala Asp Pro Thr<br>     290               295              300 | 912 |
| ctg ctc aat tgt cac aat aaa agt gct ata gac ttg gct ccc aca cca<br>Leu Leu Asn Cys His Asn Lys Ser Ala Ile Asp Leu Ala Pro Thr Pro<br>305               310              315              320 | 960 |
| cag tta aaa gaa aga tta gca tat gaa ttt aaa ggc cac tcg ttg ctg<br>Gln Leu Lys Glu Arg Leu Ala Tyr Glu Phe Lys Gly His Ser Leu Leu<br>             325               330             335 | 1008 |

```
                                      -continued caa gct gca cga gaa gct gat gtt act cga atc aaa aaa cat ctc tct      1056
Gln Ala Ala Arg Glu Ala Asp Val Thr Arg Ile Lys Lys His Leu Ser
            340                 345                 350 ctg gaa atg gtg aat ttc aag cat cct caa aca cat gaa aca gca ttg      1104
Leu Glu Met Val Asn Phe Lys His Pro Gln Thr His Glu Thr Ala Leu
        355                 360                 365 cat tgt gct gct gca tct cca tat ccc aaa aga aag caa ata tgt gaa      1152
His Cys Ala Ala Ala Ser Pro Tyr Pro Lys Arg Lys Gln Ile Cys Glu
    370                 375                 380 ctg ttg cta aga aaa gga gca aac atc aat gaa aag act aaa gaa ttc      1200
Leu Leu Leu Arg Lys Gly Ala Asn Ile Asn Glu Lys Thr Lys Glu Phe
385                 390                 395                 400 ttg act cct ctg cac gtg gca tct gag aaa gct cat aat gat gtt gtt      1248
Leu Thr Pro Leu His Val Ala Ser Glu Lys Ala His Asn Asp Val Val
                405                 410                 415 gaa gta gtg gtg aaa cat gaa gca aag gtt aat gct ctg gat aat ctt      1296
Glu Val Val Val Lys His Glu Ala Lys Val Asn Ala Leu Asp Asn Leu
            420                 425                 430 ggt cag act tct cta cac aga gct gca tat tgt ggt cat cta caa acc      1344
Gly Gln Thr Ser Leu His Arg Ala Ala Tyr Cys Gly His Leu Gln Thr
        435                 440                 445 tgc cgc cta ctc ctg agc tat ggg tgt gat cct aac att ata tcc ctt      1392
Cys Arg Leu Leu Leu Ser Tyr Gly Cys Asp Pro Asn Ile Ile Ser Leu
    450                 455                 460 cag ggc ttt act gct tta cag atg gga aat gaa aat gta cag caa ctc      1440
Gln Gly Phe Thr Ala Leu Gln Met Gly Asn Glu Asn Val Gln Gln Leu
465                 470                 475                 480 ctc caa gag ggt atc tca tta ggt aat tca gag gca gac aga caa ttg      1488
Leu Gln Glu Gly Ile Ser Leu Gly Asn Ser Glu Ala Asp Arg Gln Leu
                485                 490                 495 ctg gaa gct gca aag gct gga gat gtc gaa act gta aaa aaa ctg tgt      1536
Leu Glu Ala Ala Lys Ala Gly Asp Val Glu Thr Val Lys Lys Leu Cys
            500                 505                 510 act gtt cag agt gtc aac tgc aga gac att gaa ggg cgt cag tct aca      1584
Thr Val Gln Ser Val Asn Cys Arg Asp Ile Glu Gly Arg Gln Ser Thr
        515                 520                 525 cca ctt cat ttt gca gct ggg tat aac aga gtg tcc gtg gtg gaa tat      1632
Pro Leu His Phe Ala Ala Gly Tyr Asn Arg Val Ser Val Val Glu Tyr
    530                 535                 540 ctg cta cag cat gga gct gat gtg cat gct aaa gat aaa gga ggc ctt      1680
Leu Leu Gln His Gly Ala Asp Val His Ala Lys Asp Lys Gly Gly Leu
545                 550                 555                 560 gta cct ttg cac aat gca tgt tct tat gga cat tat gaa gtt gca gaa      1728
Val Pro Leu His Asn Ala Cys Ser Tyr Gly His Tyr Glu Val Ala Glu
                565                 570                 575 ctt ctt gtt aaa cat gga gca gta gtt aat gta gct gat tta tgg aaa      1776
Leu Leu Val Lys His Gly Ala Val Val Asn Val Ala Asp Leu Trp Lys
            580                 585                 590 ttt aca cct tta cat gaa gca gca gca aaa gga aaa tat gaa att tgc      1824
Phe Thr Pro Leu His Glu Ala Ala Ala Lys Gly Lys Tyr Glu Ile Cys
        595                 600                 605 aaa ctt ctg ctc cag cat ggt gca gac cct aca aaa aaa aac agg gat      1872
Lys Leu Leu Leu Gln His Gly Ala Asp Pro Thr Lys Lys Asn Arg Asp
    610                 615                 620 gga aat act cct ttg gat ctt gtt aaa gat gga gat aca gat att caa      1920
Gly Asn Thr Pro Leu Asp Leu Val Lys Asp Gly Asp Thr Asp Ile Gln
625                 630                 635                 640 gat ctg ctt agg gga gat gca gct ttg cta gat gct gcc aag aag ggt      1968
Asp Leu Leu Arg Gly Asp Ala Ala Leu Leu Asp Ala Ala Lys Lys Gly
```

```
                         645                  650                  655
tgt tta gcc aga gtg aag aag ttg tct tct cct gat aat gta aat tgc       2016
Cys Leu Ala Arg Val Lys Lys Leu Ser Ser Pro Asp Asn Val Asn Cys
            660                 665                 670 cgc gat acc caa ggc aga cat tca aca cct tta cat tta gca gct ggt       2064
Arg Asp Thr Gln Gly Arg His Ser Thr Pro Leu His Leu Ala Ala Gly
            675                 680                 685 tat aat aat tta gaa gtt gca gag tat ttg tta caa cac gga gct gat       2112
Tyr Asn Asn Leu Glu Val Ala Glu Tyr Leu Leu Gln His Gly Ala Asp
            690                 695                 700 gtg aat gcc caa gac aaa gga gga ctt att cct tta cat aat gca gca       2160
Val Asn Ala Gln Asp Lys Gly Gly Leu Ile Pro Leu His Asn Ala Ala
705                 710                 715                 720 tct tac ggg cat gta gat gta gca gct cta cta ata aag tat aat gca       2208
Ser Tyr Gly His Val Asp Val Ala Ala Leu Leu Ile Lys Tyr Asn Ala
                725                 730                 735 tgt gtc aat gcc acg gac aaa tgg gct ttc aca cct ttg cac gaa gca       2256
Cys Val Asn Ala Thr Asp Lys Trp Ala Phe Thr Pro Leu His Glu Ala
            740                 745                 750 gcc caa aag gga cga aca cag ctt tgt gct ttg tta cta gcc cat gga       2304
Ala Gln Lys Gly Arg Thr Gln Leu Cys Ala Leu Leu Leu Ala His Gly
            755                 760                 765 gct gac ccg act ctt aaa aat cag gaa gga caa aca cct tta gat tta       2352
Ala Asp Pro Thr Leu Lys Asn Gln Glu Gly Gln Thr Pro Leu Asp Leu
            770                 775                 780 gtt tca gcg gat gat gtc agc gct ctt ctg aca gca gcc atg ccc cca       2400
Val Ser Ala Asp Asp Val Ser Ala Leu Leu Thr Ala Ala Met Pro Pro
785                 790                 795                 800 tct gct ctg ccc tct tgt tac aag cct caa gtg ctc aat ggt gtg aga       2448
Ser Ala Leu Pro Ser Cys Tyr Lys Pro Gln Val Leu Asn Gly Val Arg
                805                 810                 815 agc cca gga gcc act gca gat gct ctc tct tca ggt cca tct agc cca       2496
Ser Pro Gly Ala Thr Ala Asp Ala Leu Ser Ser Gly Pro Ser Ser Pro
            820                 825                 830 tca agc ctt tct gca gcc agc agt ctt gac aac tta tct ggg agt ttt       2544
Ser Ser Leu Ser Ala Ala Ser Ser Leu Asp Asn Leu Ser Gly Ser Phe
            835                 840                 845 tca gaa ctg tct tca gta gtt agt tca gga aca gag ggt gct tcc           2592
Ser Glu Leu Ser Ser Val Val Ser Ser Gly Thr Glu Gly Ala Ser
850                 855                 860 agt ttg gag aaa aag gag gtt cca gga gta gat ttt agc ata act caa       2640
Ser Leu Glu Lys Lys Glu Val Pro Gly Val Asp Phe Ser Ile Thr Gln
865                 870                 875                 880 ttc gta agg aat ctt gga ctt gag cac cta atg gat ata ttt gag aga       2688
Phe Val Arg Asn Leu Gly Leu Glu His Leu Met Asp Ile Phe Glu Arg
                885                 890                 895 gaa cag atc act ttg gat gta tta gtt gag atg ggg cac aag gag ctg       2736
Glu Gln Ile Thr Leu Asp Val Leu Val Glu Met Gly His Lys Glu Leu
            900                 905                 910 aag gag att gga atc aat gct tat gga cat agg cac aaa cta att aaa       2784
Lys Glu Ile Gly Ile Asn Ala Tyr Gly His Arg His Lys Leu Ile Lys
            915                 920                 925 gga gtc gag aga ctt atc tcc gga caa caa ggt ctt aac cca tat tta       2832
Gly Val Glu Arg Leu Ile Ser Gly Gln Gln Gly Leu Asn Pro Tyr Leu
            930                 935                 940 act ttg aac acc tct ggt agt gga aca att ctt ata gat ctg tct cct       2880
Thr Leu Asn Thr Ser Gly Ser Gly Thr Ile Leu Ile Asp Leu Ser Pro
945                 950                 955                 960 gat gat aaa gag ttt cag tct gtg gag gaa gag atg caa agt aca gtt       2928
```

```
Asp Asp Lys Glu Phe Gln Ser Val Glu Glu Glu Met Gln Ser Thr Val
            965                 970                 975 cga gag cac aga gat gga ggt cat gca ggt gga atc ttc aac aga tac    2976
Arg Glu His Arg Asp Gly Gly His Ala Gly Gly Ile Phe Asn Arg Tyr
        980                 985                 990 aat att ctc aag att cag aag gtt tgt aac aag aaa cta tgg gaa aga    3024
Asn Ile Leu Lys Ile Gln Lys Val Cys Asn Lys Lys Leu Trp Glu Arg
        995                 1000                1005 tac act cac cgg aga aaa gaa gtt tct gaa gaa aac cac aac cat        3069
Tyr Thr His Arg Arg Lys Glu Val Ser Glu Glu Asn His Asn His
    1010                1015                1020 gcc aat gaa cga atg cta ttt cat ggg tct cct ttt gtg aat gca        3114
Ala Asn Glu Arg Met Leu Phe His Gly Ser Pro Phe Val Asn Ala
    1025                1030                1035 att atc cac aaa ggc ttt gat gaa agg cat gcg tac ata ggt ggt        3159
Ile Ile His Lys Gly Phe Asp Glu Arg His Ala Tyr Ile Gly Gly
    1040                1045                1050 atg ttt gga gct ggc att tat ttt gct gaa aac tct tcc aaa agc        3204
Met Phe Gly Ala Gly Ile Tyr Phe Ala Glu Asn Ser Ser Lys Ser
    1055                1060                1065 aat caa tat gta tat gga att gga gga ggt act ggg tgt cca gtt        3249
Asn Gln Tyr Val Tyr Gly Ile Gly Gly Gly Thr Gly Cys Pro Val
    1070                1075                1080 cac aaa gac aga tct tgt tac att tgc cac agg cag ctg ctc ttt        3294
His Lys Asp Arg Ser Cys Tyr Ile Cys His Arg Gln Leu Leu Phe
    1085                1090                1095 tgc cgg gta acc ttg gga aag tct ttc ctg cag ttc agt gca atg        3339
Cys Arg Val Thr Leu Gly Lys Ser Phe Leu Gln Phe Ser Ala Met
    1100                1105                1110 aaa atg gca cat tct cct cca ggt cat cac tca gtc act ggt agg        3384
Lys Met Ala His Ser Pro Pro Gly His His Ser Val Thr Gly Arg
    1115                1120                1125 ccc agt gta aat ggc cta gca tta gct gaa tat gtt att tac aga        3429
Pro Ser Val Asn Gly Leu Ala Leu Ala Glu Tyr Val Ile Tyr Arg
    1130                1135                1140 gga gaa cag gct tat cct gag tat tta att act tac cag att atg        3474
Gly Glu Gln Ala Tyr Pro Glu Tyr Leu Ile Thr Tyr Gln Ile Met
    1145                1150                1155 agg cct gaa ggt atg gtc gat gga taa atagttattt taagaaacta          3521
Arg Pro Glu Gly Met Val Asp Gly
    1160                1165 attccactga acctaaaatc atcaaagcag cagtggcctc tacgttttac tcctttgctg   3581
aaaaaaaatc atcttgccca caggcctgtg gcaaaggat aaaaatgtga acgaagttta    3641
acattctgac ttgataaagc tttaataatg tacagtgttt tctaaatatt tcctgttttt   3701
tcagcacttt aacagatgcc attccaggtt aaactgggtt gtctgtacta aattataaac   3761
agagttaact tgaaccttt atatgttatg cattgattct aacaaactgt aatgccctca    3821
acagaactaa ttttactaat acaatactgt gttctttaaa acacagcatt tacactgaat   3881
acaatttcat ttgtaaaact gtaaataaga gcttttgtac tagcccagta tttatttaca   3941
ttgctttgta atataaatct gttttagaac tgcagcggtt tacaaaattt tttcatatgt   4001
attgttcatc tatacttcat cttacatcgt catgattgag tgatctttac atttgattcc   4061
agaggctatg ttcagttgtt agttgggaaa gattgagtta tcagatttaa tttgccgatg   4121
ggagccttta tctgtcatta gaaatctttc tcatttaaga acttatgaat atgctgaaga   4181
tttaatttgt gataccttg tatgtatgag acacattcca aagagctcta actatgatag    4241
```

-continued

```
gtcctgatta ctaaagaagc ttctttactg gcctcaattt ctagctttca tgttggaaaa    4301
ttttctgcag tccttctgtg aaaattagag caaagtgctc ctgtttttta gagaaactaa    4361
atcttgctgt tgaacaatta ttgtgttctt tcatggaac ataagtagga tgttacattt     4421
ccagggtggg aagggtaatc ctaaatcatt tcccaatcta ttctaattac cttaaatcta    4481
aaggggaaaa aaaaaatcac aaacaggact gggtagtttt ttatcctaag tatatttttt    4541
cctgttcttt ttacttggtt ttattgctgt atttatagcc aatctataca tcatgggtaa    4601
acttaaccca gaactataaa atgtagttgt ctcagtcccc tccaggcctc ctgaatgggc    4661
aagtgcagtg aaacaggtgc ttcttgctcc tgggttttct ctccatgatg ttatgcccaa    4721
ttggaaatat gctgtcagtt tgtgcaccat atggtgacca cgcctgtgct cagtttggca    4781
gctatagaag gaaatgctgt cccataaaat gccattccta ttttctaata taaaactctt    4841
ttccaggaag catgcttaag catcttgtta cagagacata catccattat ggcttggcaa    4901
tctcttttat ttgttgactc tagctcccctt caaagtcgag gaaagatctt tactcactta    4961
atgaggacat tccccatcac tgtctgtacc agttcacctt tattttacgt tttattcagt    5021
ctgtaaatta actggcccctt tgcagtaact tgtacataaa gtgctagaaa atcatgttcc    5081
ttgtcctgag taagagttaa tcagagtaaa tgcatttctg gagttgtttc tgtgatgtaa    5141
attatgatca ttatttaaga agtcaaatcc tgatcttgaa gtgcttttta tacagctctc    5201
taataattac aaatatccga aagtcatttc ttggaacaca agtggagtat gccaaatttt    5261
atatgaattt ttcagattat ctaagcttcc aggtttata attagaagat aatgagagaa    5321
ttaatggggt ttatatttac attatctctc aactatgtag cccatattac tcaccctatg    5381
agtgaatctg gaattgcttt tcatgtgaaa tcattgtggt ctatgagttt acaatactgc    5441
aaactgtgtt attttatcta atccattgct taatgagtgt gttttccat gaatgaatat     5501
accgtggttc atatgttagc atggcagcat tttcagatag ctttttgttt gttgggaagt    5561
tggggttttg gggggagggg gagtattagt acgttgcatg aaatagctta ctttataatg    5621
atggaattgc ttttttcttt gtcttgtgat tttttttttt gaagtgaaat ttaacttttt    5681
gtgcaagtag tactattata cccatcttca gtgtcttact tgtactgtat cacattccat    5741
accctcattt aattcttaat aaaactgttc acttgtt                             5778
```

<210> SEQ ID NO 15
<211> LENGTH: 1166
<212> TYPE: PRT
<213> ORGANISM: Homo sapiens

<400> SEQUENCE: 15

```
Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
            20                  25                  30

Arg Asn Gly Asp Val Glu Arg Val Lys Arg Leu Val Thr Pro Glu Lys
        35                  40                  45

Val Asn Ser Arg Asp Thr Ala Gly Arg Lys Ser Thr Pro Leu His Phe
    50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
```

-continued

```
                100                 105                 110
His Gly Ala Asp Pro Asn Ala Arg Asp Asn Trp Asn Tyr Thr Pro Leu
            115                 120                 125
His Glu Ala Ala Ile Lys Gly Lys Ile Asp Val Cys Ile Val Leu Leu
        130                 135                 140
Gln His Gly Ala Glu Pro Thr Ile Arg Asn Thr Asp Gly Arg Thr Ala
145                 150                 155                 160
Leu Asp Leu Ala Asp Pro Ser Ala Lys Ala Val Leu Thr Gly Glu Tyr
                165                 170                 175
Lys Lys Asp Glu Leu Leu Glu Ser Ala Arg Ser Gly Asn Glu Glu Lys
            180                 185                 190
Met Met Ala Leu Leu Thr Pro Leu Asn Val Asn Cys His Ala Ser Asp
        195                 200                 205
Gly Arg Lys Ser Thr Pro Leu His Leu Ala Ala Gly Tyr Asn Arg Val
    210                 215                 220
Lys Ile Val Gln Leu Leu Leu Gln His Gly Ala Asp Val His Ala Lys
225                 230                 235                 240
Asp Lys Gly Asp Leu Val Pro Leu His Asn Ala Cys Ser Tyr Gly His
                245                 250                 255
Tyr Glu Val Thr Glu Leu Leu Val Lys His Gly Ala Cys Val Asn Ala
            260                 265                 270
Met Asp Leu Trp Gln Phe Thr Pro Leu His Glu Ala Ala Ser Lys Asn
        275                 280                 285
Arg Val Glu Val Cys Ser Leu Leu Leu Ser Tyr Gly Ala Asp Pro Thr
    290                 295                 300
Leu Leu Asn Cys His Asn Lys Ser Ala Ile Asp Leu Ala Pro Thr Pro
305                 310                 315                 320
Gln Leu Lys Glu Arg Leu Ala Tyr Glu Phe Lys Gly His Ser Leu Leu
                325                 330                 335
Gln Ala Ala Arg Glu Ala Asp Val Thr Arg Ile Lys Lys His Leu Ser
            340                 345                 350
Leu Glu Met Val Asn Phe Lys His Pro Gln Thr His Glu Thr Ala Leu
        355                 360                 365
His Cys Ala Ala Ala Ser Pro Tyr Pro Lys Arg Lys Gln Ile Cys Glu
    370                 375                 380
Leu Leu Leu Arg Lys Gly Ala Asn Ile Asn Glu Lys Thr Lys Glu Phe
385                 390                 395                 400
Leu Thr Pro Leu His Val Ala Ser Glu Lys Ala His Asn Asp Val Val
                405                 410                 415
Glu Val Val Lys His Glu Ala Lys Val Asn Ala Leu Asp Asn Leu
            420                 425                 430
Gly Gln Thr Ser Leu His Arg Ala Ala Tyr Cys Gly His Leu Gln Thr
        435                 440                 445
Cys Arg Leu Leu Leu Ser Tyr Gly Cys Asp Pro Asn Ile Ile Ser Leu
    450                 455                 460
Gln Gly Phe Thr Ala Leu Gln Met Gly Asn Glu Asn Val Gln Gln Leu
465                 470                 475                 480
Leu Gln Glu Gly Ile Ser Leu Gly Asn Ser Glu Ala Asp Arg Gln Leu
                485                 490                 495
Leu Glu Ala Ala Lys Ala Gly Asp Val Glu Thr Val Lys Lys Leu Cys
            500                 505                 510
Thr Val Gln Ser Val Asn Cys Arg Asp Ile Glu Gly Arg Gln Ser Thr
        515                 520                 525
```

-continued

```
Pro Leu His Phe Ala Ala Gly Tyr Asn Arg Val Ser Val Glu Tyr
530                 535                 540

Leu Leu Gln His Gly Ala Asp Val His Ala Lys Asp Lys Gly Gly Leu
545                 550                 555                 560

Val Pro Leu His Asn Ala Cys Ser Tyr Gly His Tyr Glu Val Ala Glu
                565                 570                 575

Leu Leu Val Lys His Gly Ala Val Val Asn Val Ala Asp Leu Trp Lys
            580                 585                 590

Phe Thr Pro Leu His Glu Ala Ala Lys Gly Lys Tyr Glu Ile Cys
        595                 600                 605

Lys Leu Leu Gln His Gly Ala Asp Pro Thr Lys Lys Asn Arg Asp
610                 615                 620

Gly Asn Thr Pro Leu Asp Leu Val Lys Asp Gly Asp Thr Asp Ile Gln
625                 630                 635                 640

Asp Leu Leu Arg Gly Asp Ala Ala Leu Leu Asp Ala Ala Lys Lys Gly
                645                 650                 655

Cys Leu Ala Arg Val Lys Lys Leu Ser Ser Pro Asp Asn Val Asn Cys
            660                 665                 670

Arg Asp Thr Gln Gly Arg His Ser Thr Pro Leu His Leu Ala Ala Gly
        675                 680                 685

Tyr Asn Asn Leu Glu Val Ala Glu Tyr Leu Leu Gln His Gly Ala Asp
690                 695                 700

Val Asn Ala Gln Asp Lys Gly Gly Leu Ile Pro Leu His Asn Ala Ala
705                 710                 715                 720

Ser Tyr Gly His Val Asp Val Ala Ala Leu Leu Ile Lys Tyr Asn Ala
                725                 730                 735

Cys Val Asn Ala Thr Asp Lys Trp Ala Phe Thr Pro Leu His Glu Ala
            740                 745                 750

Ala Gln Lys Gly Arg Thr Gln Leu Cys Ala Leu Leu Leu Ala His Gly
        755                 760                 765

Ala Asp Pro Thr Leu Lys Asn Gln Glu Gly Gln Thr Pro Leu Asp Leu
770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
            820                 825                 830

Ser Ser Leu Ser Ala Ala Ser Ser Leu Asp Asn Leu Ser Gly Ser Phe
        835                 840                 845

Ser Glu Leu Ser Ser Val Val Ser Ser Ser Gly Thr Glu Gly Ala Ser
850                 855                 860

Ser Leu Glu Lys Lys Glu Val Pro Gly Val Asp Phe Ser Ile Thr Gln
865                 870                 875                 880

Phe Val Arg Asn Leu Gly Leu Glu His Leu Met Asp Ile Phe Glu Arg
                885                 890                 895

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
        915                 920                 925

Gly Val Glu Arg Leu Ile Ser Gly Gln Gln Gly Leu Asn Pro Tyr Leu
930                 935                 940
```

```
Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Met Gln Ser Thr Val
            965                 970                 975

Arg Glu His Arg Asp Gly Gly His Ala Gly Ile Phe Asn Arg Tyr
        980                 985                 990

Asn Ile Leu Lys Ile Gln Lys Val Cys Asn Lys Lys Leu Trp Glu Arg
            995                 1000                1005

Tyr Thr His Arg Arg Lys Glu Val Ser Glu Glu Asn His Asn His
    1010                1015                1020

Ala Asn Glu Arg Met Leu Phe His Gly Ser Pro Phe Val Asn Ala
    1025                1030                1035

Ile Ile His Lys Gly Phe Asp Glu Arg His Ala Tyr Ile Gly Gly
    1040                1045                1050

Met Phe Gly Ala Gly Ile Tyr Phe Ala Glu Asn Ser Ser Lys Ser
    1055                1060                1065

Asn Gln Tyr Val Tyr Gly Ile Gly Gly Gly Thr Gly Cys Pro Val
    1070                1075                1080

His Lys Asp Arg Ser Cys Tyr Ile Cys His Arg Gln Leu Leu Phe
    1085                1090                1095

Cys Arg Val Thr Leu Gly Lys Ser Phe Leu Gln Phe Ser Ala Met
    1100                1105                1110

Lys Met Ala His Ser Pro Pro Gly His His Ser Val Thr Gly Arg
    1115                1120                1125

Pro Ser Val Asn Gly Leu Ala Leu Ala Glu Tyr Val Ile Tyr Arg
    1130                1135                1140

Gly Glu Gln Ala Tyr Pro Glu Tyr Leu Ile Thr Tyr Gln Ile Met
    1145                1150                1155

Arg Pro Glu Gly Met Val Asp Gly
    1160                1165

<210> SEQ ID NO 16
<211> LENGTH: 5490
<212> TYPE: DNA
<213> ORGANISM: Homo sapiens
<220> FEATURE:
<221> NAME/KEY: CDS
<222> LOCATION: (107)..(5281)

<400> SEQUENCE: 16
cgcccgccca gccccggggg cagggaaagc ctaaattacg gaattaccgc gagcaaggag        60
cgcggaatcg gggagcgtcc ggagctagct ggatcctcta ggcagg atg gtg atg        115
                                                 Met Val Met
                                                   1 gga atc ttt gca aat tgt atc ttc tgt ttg aaa gtg aag tac tta cct        163
Gly Ile Phe Ala Asn Cys Ile Phe Cys Leu Lys Val Lys Tyr Leu Pro
      5                  10                  15 cag cag cag aag aaa aag cta caa act gac att aag gaa aat ggc gga        211
Gln Gln Gln Lys Lys Lys Leu Gln Thr Asp Ile Lys Glu Asn Gly Gly
 20                  25                  30                  35 aag ttt tcc ttt tcg tta aat cct cag tgc aca cat ata atc tta gat        259
Lys Phe Ser Phe Ser Leu Asn Pro Gln Cys Thr His Ile Ile Leu Asp
                 40                  45                  50 aat gct gat gtt ctg agt cag tac caa ctg aat tct atc caa aag aac        307
Asn Ala Asp Val Leu Ser Gln Tyr Gln Leu Asn Ser Ile Gln Lys Asn
             55                  60                  65 cac gtt cat att gca aac cca gat ttt ata tgg aaa tct atc aga gaa        355
```

-continued

```
His Val His Ile Ala Asn Pro Asp Phe Ile Trp Lys Ser Ile Arg Glu
         70                  75                  80 aag aga ctc ttg gat gta aag aat tat gat cct tat aag ccc ctg gac    403
Lys Arg Leu Leu Asp Val Lys Asn Tyr Asp Pro Tyr Lys Pro Leu Asp
    85                  90                  95 atc aca cca cct cct gat cag aag gcg agc agt tct gaa gtg aaa aca    451
Ile Thr Pro Pro Pro Asp Gln Lys Ala Ser Ser Ser Glu Val Lys Thr
100                 105                 110                 115 gaa ggt cta tgc ccg gac agt gcc aca gag gag gaa gac act gtg gaa    499
Glu Gly Leu Cys Pro Asp Ser Ala Thr Glu Glu Glu Asp Thr Val Glu
                120                 125                 130 ctc act gag ttt ggt atg cag aat gtt gaa att cct cat ctt cct caa    547
Leu Thr Glu Phe Gly Met Gln Asn Val Glu Ile Pro His Leu Pro Gln
        135                 140                 145 gat ttt gaa gtt gca aaa tat aac acc ttg gag aaa gtg gga atg gag    595
Asp Phe Glu Val Ala Lys Tyr Asn Thr Leu Glu Lys Val Gly Met Glu
        150                 155                 160 gga ggc cag gaa gct gtg gtg gtg gag ctt cag tgt tcg cgg gac tcc    643
Gly Gly Gln Glu Ala Val Val Val Glu Leu Gln Cys Ser Arg Asp Ser
    165                 170                 175 agg gac tgt cct ttc ctg ata tcc tca cac ttc ctc ctg gat gat ggc    691
Arg Asp Cys Pro Phe Leu Ile Ser Ser His Phe Leu Leu Asp Asp Gly
180                 185                 190                 195 atg gag act aga aga cag ttt gct ata aag aaa acc tct gaa gat gca    739
Met Glu Thr Arg Arg Gln Phe Ala Ile Lys Lys Thr Ser Glu Asp Ala
                200                 205                 210 agt gaa tac ttt gaa aat tac att gaa gaa ctg aag aaa caa gga ttt    787
Ser Glu Tyr Phe Glu Asn Tyr Ile Glu Glu Leu Lys Lys Gln Gly Phe
        215                 220                 225 cta cta aga gaa cat ttc aca cct gaa gca acc caa tta gca tct gaa    835
Leu Leu Arg Glu His Phe Thr Pro Glu Ala Thr Gln Leu Ala Ser Glu
        230                 235                 240 caa ttg caa gca ttg ctt ttg gag gaa gtc atg aat tca agc act ctg    883
Gln Leu Gln Ala Leu Leu Leu Glu Glu Val Met Asn Ser Ser Thr Leu
245                 250                 255 agc caa gag gtg agc gat tta gta gag atg att tgg gca gag gcc ctg    931
Ser Gln Glu Val Ser Asp Leu Val Glu Met Ile Trp Ala Glu Ala Leu
260                 265                 270                 275 ggc cac ctg gaa cac atg ctt ctc aag cca gtg aac agg att agc ctc    979
Gly His Leu Glu His Met Leu Leu Lys Pro Val Asn Arg Ile Ser Leu
                280                 285                 290 aac gat gtg agc aag gca gag ggg att ctc ctt cta gta aag gca gca    1027
Asn Asp Val Ser Lys Ala Glu Gly Ile Leu Leu Leu Val Lys Ala Ala
        295                 300                 305 ctg aaa aat gga gaa aca gca gag caa ttg caa aag atg atg aca gag    1075
Leu Lys Asn Gly Glu Thr Ala Glu Gln Leu Gln Lys Met Met Thr Glu
        310                 315                 320 ttt tac aga ctg ata cct cac aaa ggc aca atg ccc aaa gaa gtg aac    1123
Phe Tyr Arg Leu Ile Pro His Lys Gly Thr Met Pro Lys Glu Val Asn
    325                 330                 335 ctg gga cta ttg gct aag aaa gca gac ctc tgc cag cta ata aga gac    1171
Leu Gly Leu Leu Ala Lys Lys Ala Asp Leu Cys Gln Leu Ile Arg Asp
340                 345                 350                 355 atg gtt aat gtc tgt gaa act aat ttg tcc aaa ccc aac cca cca tcc    1219
Met Val Asn Val Cys Glu Thr Asn Leu Ser Lys Pro Asn Pro Pro Ser
                360                 365                 370 ctg gcc aaa tac cga gct ttg agg tgc aaa att gag cat gtt gaa cag    1267
Leu Ala Lys Tyr Arg Ala Leu Arg Cys Lys Ile Glu His Val Glu Gln
        375                 380                 385
```

```
aat act gaa gaa ttt ctc agg gtt aga aaa gag gtt ttg cag aat cat       1315
Asn Thr Glu Glu Phe Leu Arg Val Arg Lys Glu Val Leu Gln Asn His
        390                 395                 400 cac agt aag agc cca gtg gat gtc ttg cag ata ttt aga gtt ggc aga       1363
His Ser Lys Ser Pro Val Asp Val Leu Gln Ile Phe Arg Val Gly Arg
    405                 410                 415 gtg aat gaa acc aca gag ttt ttg agc aaa ctt ggt aat gtg agg ccc       1411
Val Asn Glu Thr Thr Glu Phe Leu Ser Lys Leu Gly Asn Val Arg Pro
420                 425                 430                 435 ttg ttg cat ggt tct cct gta caa aac atc gtg gga atc ttg tgt cga       1459
Leu Leu His Gly Ser Pro Val Gln Asn Ile Val Gly Ile Leu Cys Arg
                440                 445                 450 ggg ttg ctt tta ccc aaa gta gtg gaa gat cgt ggt gtg caa aga aca       1507
Gly Leu Leu Leu Pro Lys Val Val Glu Asp Arg Gly Val Gln Arg Thr
            455                 460                 465 gac gtc gga aac ctt gga agt ggg att tat ttc agt gat tcg ctc agt       1555
Asp Val Gly Asn Leu Gly Ser Gly Ile Tyr Phe Ser Asp Ser Leu Ser
        470                 475                 480 aca agt atc aag tac tca cac ccg gga gag aca gat ggc acc aga ctc       1603
Thr Ser Ile Lys Tyr Ser His Pro Gly Glu Thr Asp Gly Thr Arg Leu
    485                 490                 495 ctg ctc att tgt gac gta gcc ctc gga aag tgt atg gac tta cat gag       1651
Leu Leu Ile Cys Asp Val Ala Leu Gly Lys Cys Met Asp Leu His Glu
500                 505                 510                 515 aag gac ttt ccc tta act gaa gca cca cca ggc tac gac agt gtg cat       1699
Lys Asp Phe Pro Leu Thr Glu Ala Pro Pro Gly Tyr Asp Ser Val His
                520                 525                 530 gga gtt tca caa aca gcc tct gtc acc aca gac ttt gag gat gat gaa       1747
Gly Val Ser Gln Thr Ala Ser Val Thr Thr Asp Phe Glu Asp Asp Glu
            535                 540                 545 ttt gtt gtc tat aaa acc aat cag gtt aaa atg aaa tat att att aaa       1795
Phe Val Val Tyr Lys Thr Asn Gln Val Lys Met Lys Tyr Ile Ile Lys
        550                 555                 560 ttt tcc atg cct gga gat cag ata aag gac ttt cat cct agt gat cat       1843
Phe Ser Met Pro Gly Asp Gln Ile Lys Asp Phe His Pro Ser Asp His
    565                 570                 575 act gaa tta gag gaa tac aga cct gag ttt tca aat ttt tca aag gtt       1891
Thr Glu Leu Glu Glu Tyr Arg Pro Glu Phe Ser Asn Phe Ser Lys Val
580                 585                 590                 595 gaa gat tac cag tta cca gat gcc aaa act tcc agc agc acc aag gcc       1939
Glu Asp Tyr Gln Leu Pro Asp Ala Lys Thr Ser Ser Ser Thr Lys Ala
                600                 605                 610 ggc ctc cag gat gcc tct ggg aac ttg gtt cct ctg gag gat gtc cac       1987
Gly Leu Gln Asp Ala Ser Gly Asn Leu Val Pro Leu Glu Asp Val His
            615                 620                 625 atc aaa ggg aga atc ata gac act gta gcc cag gtc att gtt ttt cag       2035
Ile Lys Gly Arg Ile Ile Asp Thr Val Ala Gln Val Ile Val Phe Gln
        630                 635                 640 aca tac aca aat aaa agt cac gtg ccc att gag gca aaa tat atc ttt       2083
Thr Tyr Thr Asn Lys Ser His Val Pro Ile Glu Ala Lys Tyr Ile Phe
    645                 650                 655 cct ttg gat gac aag gcc gct gtg tgt ggc ttc gaa gcc ttc atc aat       2131
Pro Leu Asp Asp Lys Ala Ala Val Cys Gly Phe Glu Ala Phe Ile Asn
660                 665                 670                 675 ggg aag cac ata gtt gga gag att aaa gag aag gaa gaa gcc cag caa       2179
Gly Lys His Ile Val Gly Glu Ile Lys Glu Lys Glu Glu Ala Gln Gln
                680                 685                 690 gag tac cta gaa gcc gtg acc cag ggc cat ggc gct tac ctg atg agt       2227
Glu Tyr Leu Glu Ala Val Thr Gln Gly His Gly Ala Tyr Leu Met Ser
            695                 700                 705
```

| | | |
|---|---|---|
| cag gat gct ccg gac gtt ttt act gta agt gtt gga aac tta ccc cct<br>Gln Asp Ala Pro Asp Val Phe Thr Val Ser Val Gly Asn Leu Pro Pro<br>710                      715                   720 | | 2275 |
| aag gct aag gtt ctt ata aaa att acc tac atc aca gaa ctc agc atc<br>Lys Ala Lys Val Leu Ile Lys Ile Thr Tyr Ile Thr Glu Leu Ser Ile<br>725                      730                   735 | | 2323 |
| ctg ggc act gtt ggt gtc ttt ttc atg ccc gcc acc gta gca ccc tgg<br>Leu Gly Thr Val Gly Val Phe Phe Met Pro Ala Thr Val Ala Pro Trp<br>740                      745                   750                   755 | | 2371 |
| caa cag gac aag gct ttg aat gaa aac ctt cag gat aca gta gag aag<br>Gln Gln Asp Lys Ala Leu Asn Glu Asn Leu Gln Asp Thr Val Glu Lys<br>                   760                   765                   770 | | 2419 |
| att tgt ata aaa gaa ata gga aca aag caa agc ttc tct ttg act atg<br>Ile Cys Ile Lys Glu Ile Gly Thr Lys Gln Ser Phe Ser Leu Thr Met<br>775                      780                   785 | | 2467 |
| tct att gag atg ccg tat gtg att gaa ttc att ttc agt gat aca cat<br>Ser Ile Glu Met Pro Tyr Val Ile Glu Phe Ile Phe Ser Asp Thr His<br>                   790                   795                   800 | | 2515 |
| gaa ctg aaa caa aag cgc aca gac tgc aaa gct gtc att agc acc atg<br>Glu Leu Lys Gln Lys Arg Thr Asp Cys Lys Ala Val Ile Ser Thr Met<br>805                      810                   815 | | 2563 |
| gaa ggc agc tcc tta gac agc agt gga ttt tct ctc cac atc ggt ttg<br>Glu Gly Ser Ser Leu Asp Ser Ser Gly Phe Ser Leu His Ile Gly Leu<br>820                      825                   830                   835 | | 2611 |
| tct gct gcc tat ctc cca aga atg tgg gtt gaa aaa cat cca gaa aaa<br>Ser Ala Ala Tyr Leu Pro Arg Met Trp Val Glu Lys His Pro Glu Lys<br>                   840                   845                   850 | | 2659 |
| gaa agc gag gct tgc atg ctt gtc ttt caa ccc gat ctc gat gtc gac<br>Glu Ser Glu Ala Cys Met Leu Val Phe Gln Pro Asp Leu Asp Val Asp<br>855                      860                   865 | | 2707 |
| ctc cct gac cta gcc agt gag agc gaa gtg att att tgt ctt gac tgc<br>Leu Pro Asp Leu Ala Ser Glu Ser Glu Val Ile Ile Cys Leu Asp Cys<br>870                      875                   880 | | 2755 |
| tcc agt tcc atg gag ggt gtg aca ttc ttg caa gcc aag caa atc acc<br>Ser Ser Ser Met Glu Gly Val Thr Phe Leu Gln Ala Lys Gln Ile Thr<br>885                      890                   895 | | 2803 |
| ttg cat gcg ctg tcc ttg gtg ggt gag aag cag aaa gta aat att atc<br>Leu His Ala Leu Ser Leu Val Gly Glu Lys Gln Lys Val Asn Ile Ile<br>900                      905                   910                   915 | | 2851 |
| cag ttc ggc aca ggt tac aag gag cta ttt tcg tat cct aag cat atc<br>Gln Phe Gly Thr Gly Tyr Lys Glu Leu Phe Ser Tyr Pro Lys His Ile<br>                   920                   925                   930 | | 2899 |
| aca agc aat acc acg gca gca gag ttc atc atg tct gcc aca cct acc<br>Thr Ser Asn Thr Thr Ala Ala Glu Phe Ile Met Ser Ala Thr Pro Thr<br>                   935                   940                   945 | | 2947 |
| atg ggg aac aca gac ttc tgg aaa aca ctc cga tat ctt agc tta ttg<br>Met Gly Asn Thr Asp Phe Trp Lys Thr Leu Arg Tyr Leu Ser Leu Leu<br>950                      955                   960 | | 2995 |
| tac cct gct cga ggg tca cgg aac atc ctc ctg gtg tct gat ggg cac<br>Tyr Pro Ala Arg Gly Ser Arg Asn Ile Leu Leu Val Ser Asp Gly His<br>965                      970                   975 | | 3043 |
| ctc cag gat gag agc ctg aca tta cag ctc gtg aag agg agc cgc ccg<br>Leu Gln Asp Glu Ser Leu Thr Leu Gln Leu Val Lys Arg Ser Arg Pro<br>980                      985                   990                   995 | | 3091 |
| cac acc agg tta ttc    gcc tgc ggt atc ggt    tct aca gca aat cgt<br>His Thr Arg Leu Phe    Ala Cys Gly Ile Gly    Ser Thr Ala Asn Arg<br>                 1000                  1005                 1010 | | 3136 |
| cac gtc tta agg att    ttg tcc cag tgt ggt    gcc gga gta ttt gaa<br>His Val Leu Arg Ile    Leu Ser Gln Cys Gly    Ala Gly Val Phe Glu | | 3181 |

```
                1015                  1020                  1025
tat ttt aat gca aaa  tcc aag cat agt tgg  aga aaa cag ata gaa       3226
Tyr Phe Asn Ala Lys  Ser Lys His Ser Trp  Arg Lys Gln Ile Glu
        1030                  1035                  1040 gac caa atg acc agg  cta tgt tct ccg agt  tgc cac tct gtc tcc       3271
Asp Gln Met Thr Arg  Leu Cys Ser Pro Ser  Cys His Ser Val Ser
        1045                  1050                  1055 gtc aaa tgg cag caa  ctc aat cca gat gcg  ccc gag gcc ctg cag       3316
Val Lys Trp Gln Gln  Leu Asn Pro Asp Ala  Pro Glu Ala Leu Gln
        1060                  1065                  1070 gcc cca gcc cag gtg  cca tcc ttg ttt cgc  aat gat cga ctc ctt       3361
Ala Pro Ala Gln Val  Pro Ser Leu Phe Arg  Asn Asp Arg Leu Leu
        1075                  1080                  1085 gtc tat gga ttc att  cct cac tgc aca caa  gca act ctg tgt gca       3406
Val Tyr Gly Phe Ile  Pro His Cys Thr Gln  Ala Thr Leu Cys Ala
        1090                  1095                  1100 cta att caa gag aaa  gaa ttt tgt aca atg  gtg tcg act act gag       3451
Leu Ile Gln Glu Lys  Glu Phe Cys Thr Met  Val Ser Thr Thr Glu
        1105                  1110                  1115 ctt cag aag aca act  gga act atg atc cac  aag ctg gca gcc cga       3496
Leu Gln Lys Thr Thr  Gly Thr Met Ile His  Lys Leu Ala Ala Arg
        1120                  1125                  1130 gct cta atc aga gat  tat gaa gat ggc att  ctt cac gaa aat gaa       3541
Ala Leu Ile Arg Asp  Tyr Glu Asp Gly Ile  Leu His Glu Asn Glu
        1135                  1140                  1145 acc agt cat gag atg  aaa aaa caa acc ttg  aaa tct ctg att att       3586
Thr Ser His Glu Met  Lys Lys Gln Thr Leu  Lys Ser Leu Ile Ile
        1150                  1155                  1160 aaa ctc agt aaa gaa  aac tct ctc ata aca  caa ttt aca agc ttt       3631
Lys Leu Ser Lys Glu  Asn Ser Leu Ile Thr  Gln Phe Thr Ser Phe
        1165                  1170                  1175 gtg gca gtt gag aaa  agg gat gag aat gag  tcg cct ttt cct gat       3676
Val Ala Val Glu Lys  Arg Asp Glu Asn Glu  Ser Pro Phe Pro Asp
        1180                  1185                  1190 att cca aaa gtt tct  gaa ctt att gcc aaa  gaa gat gta gac ttc       3721
Ile Pro Lys Val Ser  Glu Leu Ile Ala Lys  Glu Asp Val Asp Phe
        1195                  1200                  1205 ctg ccc tac atg agc  tgg cag ggg gag ccc  caa gaa gcc gtc agg       3766
Leu Pro Tyr Met Ser  Trp Gln Gly Glu Pro  Gln Glu Ala Val Arg
        1210                  1215                  1220 aac cag tct ctt tta  gca tcc tct gag tgg  cca gaa tta cgt tta       3811
Asn Gln Ser Leu Leu  Ala Ser Ser Glu Trp  Pro Glu Leu Arg Leu
        1225                  1230                  1235 tcc aaa cga aaa cat  agg aaa att cca ttt  tcc aaa aga aaa atg       3856
Ser Lys Arg Lys His  Arg Lys Ile Pro Phe  Ser Lys Arg Lys Met
        1240                  1245                  1250 gaa tta tct cag cca  gaa gtt tct gaa gat  ttt gaa gag gat ggc       3901
Glu Leu Ser Gln Pro  Glu Val Ser Glu Asp  Phe Glu Glu Asp Gly
        1255                  1260                  1265 tta ggt gta cta cca  gct ttc aca tca aat  ttg gaa cgt gga ggt       3946
Leu Gly Val Leu Pro  Ala Phe Thr Ser Asn  Leu Glu Arg Gly Gly
        1270                  1275                  1280 gtg gaa aag cta ttg  gat tta agt tgg aca  gag tca tgt aaa cca       3991
Val Glu Lys Leu Leu  Asp Leu Ser Trp Thr  Glu Ser Cys Lys Pro
        1285                  1290                  1295 aca gca act gaa cca  cta ttt aag aaa gtc  agt cca tgg gaa aca       4036
Thr Ala Thr Glu Pro  Leu Phe Lys Lys Val  Ser Pro Trp Glu Thr
        1300                  1305                  1310 tct act tct agc ttt  ttt cct att ttg gct  ccg gcc gtt ggt tcc       4081
```

|   |   |
|---|---|
| Ser Thr Ser Ser Phe Phe Pro Ile Leu Ala Pro Ala Val Gly Ser<br>            1315                   1320                 1325 |   |
| tat ctt acc ccg act acc cgc gct cac agt cct gct tcc ttg tct<br>Tyr Leu Thr Pro Thr Thr Arg Ala His Ser Pro Ala Ser Leu Ser<br>            1330                   1335                 1340 | 4126 |
| ttt gcc tca tat cgt cag gta gct agt ttc ggt tca gct gct cct<br>Phe Ala Ser Tyr Arg Gln Val Ala Ser Phe Gly Ser Ala Ala Pro<br>            1345                   1350                 1355 | 4171 |
| ccc aga cag ttt gat gca tct caa ttc agc caa ggc cct gtg cct<br>Pro Arg Gln Phe Asp Ala Ser Gln Phe Ser Gln Gly Pro Val Pro<br>            1360                   1365                 1370 | 4216 |
| ggc act tgt gct gac tgg atc cca cag tcg gcg tct tgt ccc aca<br>Gly Thr Cys Ala Asp Trp Ile Pro Gln Ser Ala Ser Cys Pro Thr<br>            1375                   1380                 1385 | 4261 |
| gga cct ccc cag aac cca cct tct gca ccc tat tgt ggc att gtt<br>Gly Pro Pro Gln Asn Pro Pro Ser Ala Pro Tyr Cys Gly Ile Val<br>            1390                   1395                 1400 | 4306 |
| ttt tca ggg agc tca tta agc tct gca cag tct gct cca ctg caa<br>Phe Ser Gly Ser Ser Leu Ser Ser Ala Gln Ser Ala Pro Leu Gln<br>            1405                   1410                 1415 | 4351 |
| cat cct gga ggc ttt act acc agg cct tct gct ggc acc ttc cct<br>His Pro Gly Gly Phe Thr Thr Arg Pro Ser Ala Gly Thr Phe Pro<br>            1420                   1425                 1430 | 4396 |
| gag ctg gat tct ccc cag ctt cat ttc tct ctt cct aca gac cct<br>Glu Leu Asp Ser Pro Gln Leu His Phe Ser Leu Pro Thr Asp Pro<br>            1435                   1440                 1445 | 4441 |
| gat ccc atc aga ggt ttt ggg tct tat cat ccc tct gct tac tct<br>Asp Pro Ile Arg Gly Phe Gly Ser Tyr His Pro Ser Ala Tyr Ser<br>            1450                   1455                 1460 | 4486 |
| cct ttt cat ttt caa cct tcc gca gcc tct ttg act gcc aac ctt<br>Pro Phe His Phe Gln Pro Ser Ala Ala Ser Leu Thr Ala Asn Leu<br>            1465                   1470                 1475 | 4531 |
| agg ctg cca atg gcc tct gct tta cct gag gct ctt tgc agt cag<br>Arg Leu Pro Met Ala Ser Ala Leu Pro Glu Ala Leu Cys Ser Gln<br>            1480                   1485                 1490 | 4576 |
| tcc cgg act acc cca gta gat ctc tgt ctt cta gaa gaa tca gta<br>Ser Arg Thr Thr Pro Val Asp Leu Cys Leu Leu Glu Glu Ser Val<br>            1495                   1500                 1505 | 4621 |
| ggc agt ctc gaa gga agt cga tgt cct gtc ttt gct ttt caa agt<br>Gly Ser Leu Glu Gly Ser Arg Cys Pro Val Phe Ala Phe Gln Ser<br>            1510                   1515                 1520 | 4666 |
| tct gac aca gaa agt gat gag cta tca gaa gta ctt caa gac agc<br>Ser Asp Thr Glu Ser Asp Glu Leu Ser Glu Val Leu Gln Asp Ser<br>            1525                   1530                 1535 | 4711 |
| tgc ttt tta caa ata aag tgt gat aca aaa gat gac agt atc ccg<br>Cys Phe Leu Gln Ile Lys Cys Asp Thr Lys Asp Asp Ser Ile Pro<br>            1540                   1545                 1550 | 4756 |
| tgc ttt ctg gaa tta aaa gaa gag gat gaa ata gtg tgc aca caa<br>Cys Phe Leu Glu Leu Lys Glu Glu Asp Glu Ile Val Cys Thr Gln<br>            1555                   1560                 1565 | 4801 |
| cac tgg cag gat gct gtg cct tgg aca gaa ctc ctc agt cta cag<br>His Trp Gln Asp Ala Val Pro Trp Thr Glu Leu Leu Ser Leu Gln<br>            1570                   1575                 1580 | 4846 |
| aca gag gat ggc ttc tgg aaa ctt aca cca gaa ctg gga ctt ata<br>Thr Glu Asp Gly Phe Trp Lys Leu Thr Pro Glu Leu Gly Leu Ile<br>            1585                   1590                 1595 | 4891 |
| tta aat ctt aat aca aat ggt ttg cac agc ttt ctt aaa caa aaa<br>Leu Asn Leu Asn Thr Asn Gly Leu His Ser Phe Leu Lys Gln Lys<br>            1600                   1605                 1610 | 4936 |

-continued

```
ggc att caa tct cta  ggt gta aaa gga aga  gaa tgt ctc ctg gac       4981
Gly Ile Gln Ser Leu  Gly Val Lys Gly Arg  Glu Cys Leu Leu Asp
            1615                 1620                 1625 cta att gcc aca atg  ctg gta cta cag ttt  att cgc acc agg ttg       5026
Leu Ile Ala Thr Met  Leu Val Leu Gln Phe  Ile Arg Thr Arg Leu
            1630                 1635                 1640 gaa aaa gag gga ata  gtg ttc aaa tca ctg  atg aaa atg gat gac       5071
Glu Lys Glu Gly Ile  Val Phe Lys Ser Leu  Met Lys Met Asp Asp
            1645                 1650                 1655 cct tct att tcc agg  aat att ccc tgg gct  ttt gag gca ata aag       5116
Pro Ser Ile Ser Arg  Asn Ile Pro Trp Ala  Phe Glu Ala Ile Lys
            1660                 1665                 1670 caa gca agt gaa tgg  gta aga aga act gaa  gga cag tac cca tct       5161
Gln Ala Ser Glu Trp  Val Arg Arg Thr Glu  Gly Gln Tyr Pro Ser
            1675                 1680                 1685 atc tgc cca cgg ctt  gaa ctg ggg aac gac  tgg gac tct gcc acc       5206
Ile Cys Pro Arg Leu  Glu Leu Gly Asn Asp  Trp Asp Ser Ala Thr
            1690                 1695                 1700 aag cag ttg ctg gga  ctc cag ccc ata agc  act gtg tcc cct ctt       5251
Lys Gln Leu Leu Gly  Leu Gln Pro Ile Ser  Thr Val Ser Pro Leu
            1705                 1710                 1715 cat aga gtc ctc cat  tac agt caa ggc taa gtcaaatgaa actgaatttt      5301
His Arg Val Leu His  Tyr Ser Gln Gly
            1720 aaactttttg catgcttcta tgtagaaaat aatcaaatga taatagataa ttataatgaa   5361 acttcattaa ggtttcattc agtgtagcaa ttactgtctt taaaaattaa gtggaagaag   5421 aattacttta atcaactaac aagcaataat aaaatgaaac ttaaaataaa aaaaaaaaa    5481 aaaaaaaaa                                                          5490
```

<210> SEQ ID NO 17
<211> LENGTH: 1724
<212> TYPE: PRT
<213> ORGANISM: Homo sapiens

<400> SEQUENCE: 17

```
Met Val Met Gly Ile Phe Ala Asn Cys Ile Phe Cys Leu Lys Val Lys
1               5                   10                  15

Tyr Leu Pro Gln Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
            100                 105                 110

Val Lys Thr Glu Gly Leu Cys Pro Asp Ser Ala Thr Glu Glu Asp
        115                 120                 125

Thr Val Glu Leu Thr Glu Phe Gly Met Gln Asn Val Glu Ile Pro His
    130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Val Glu Leu Gln Cys Ser
```

```
                          165                 170                 175
Arg Asp Ser Arg Asp Cys Pro Phe Leu Ile Ser Ser His Phe Leu Leu
                180                 185                 190

Asp Asp Gly Met Glu Thr Arg Arg Gln Phe Ala Ile Lys Lys Thr Ser
            195                 200                 205

Glu Asp Ala Ser Glu Tyr Phe Glu Asn Tyr Ile Glu Glu Leu Lys Lys
        210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
        290                 295                 300

Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
        355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
        515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590
```

```
Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
        610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
                660                 665                 670

Phe Ile Asn Gly Lys His Ile Val Gly Glu Ile Lys Glu Lys Glu Glu
            675                 680                 685

Ala Gln Gln Glu Tyr Leu Glu Ala Val Thr Gln Gly His Gly Ala Tyr
        690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
                740                 745                 750

Ala Pro Trp Gln Gln Asp Lys Ala Leu Asn Glu Asn Leu Gln Asp Thr
            755                 760                 765

Val Glu Lys Ile Cys Ile Lys Glu Ile Gly Thr Lys Gln Ser Phe Ser
770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
                820                 825                 830

Ile Gly Leu Ser Ala Ala Tyr Leu Pro Arg Met Trp Val Glu Lys His
            835                 840                 845

Pro Glu Lys Glu Ser Glu Ala Cys Met Leu Val Phe Gln Pro Asp Leu
850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
            915                 920                 925

Lys His Ile Thr Ser Asn Thr Thr Ala Ala Glu Phe Ile Met Ser Ala
            930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe Ala Cys Gly Ile Gly Ser Thr Ala
            995                 1000                1005
```

```
Asn Arg His Val Leu Arg Ile Leu Ser Gln Cys Gly Ala Gly Val
    1010                1015                1020

Phe Glu Tyr Phe Asn Ala Lys Ser Lys His Ser Trp Arg Lys Gln
    1025                1030                1035

Ile Glu Asp Gln Met Thr Arg Leu Cys Ser Pro Ser Cys His Ser
    1040                1045                1050

Val Ser Val Lys Trp Gln Gln Leu Asn Pro Asp Ala Pro Glu Ala
    1055                1060                1065

Leu Gln Ala Pro Ala Gln Val Pro Ser Leu Phe Arg Asn Asp Arg
    1070                1075                1080

Leu Leu Val Tyr Gly Phe Ile Pro His Cys Thr Gln Ala Thr Leu
    1085                1090                1095

Cys Ala Leu Ile Gln Glu Lys Glu Phe Cys Thr Met Val Ser Thr
    1100                1105                1110

Thr Glu Leu Gln Lys Thr Thr Gly Thr Met Ile His Lys Leu Ala
    1115                1120                1125

Ala Arg Ala Leu Ile Arg Asp Tyr Glu Asp Gly Ile Leu His Glu
    1130                1135                1140

Asn Glu Thr Ser His Glu Met Lys Lys Gln Thr Leu Lys Ser Leu
    1145                1150                1155

Ile Ile Lys Leu Ser Lys Glu Asn Ser Leu Ile Thr Gln Phe Thr
    1160                1165                1170

Ser Phe Val Ala Val Glu Lys Arg Asp Glu Asn Glu Ser Pro Phe
    1175                1180                1185

Pro Asp Ile Pro Lys Val Ser Glu Leu Ile Ala Lys Glu Asp Val
    1190                1195                1200

Asp Phe Leu Pro Tyr Met Ser Trp Gln Gly Glu Pro Gln Glu Ala
    1205                1210                1215

Val Arg Asn Gln Ser Leu Leu Ala Ser Ser Glu Trp Pro Glu Leu
    1220                1225                1230

Arg Leu Ser Lys Arg Lys His Arg Lys Ile Pro Phe Ser Lys Arg
    1235                1240                1245

Lys Met Glu Leu Ser Gln Pro Glu Val Ser Glu Asp Phe Glu Glu
    1250                1255                1260

Asp Gly Leu Gly Val Leu Pro Ala Phe Thr Ser Asn Leu Glu Arg
    1265                1270                1275

Gly Gly Val Glu Lys Leu Leu Asp Leu Ser Trp Thr Glu Ser Cys
    1280                1285                1290

Lys Pro Thr Ala Thr Glu Pro Leu Phe Lys Lys Val Ser Pro Trp
    1295                1300                1305

Glu Thr Ser Thr Ser Ser Phe Phe Pro Ile Leu Ala Pro Ala Val
    1310                1315                1320

Gly Ser Tyr Leu Thr Pro Thr Thr Arg Ala His Ser Pro Ala Ser
    1325                1330                1335

Leu Ser Phe Ala Ser Tyr Arg Gln Val Ala Ser Phe Gly Ser Ala
    1340                1345                1350

Ala Pro Pro Arg Gln Phe Asp Ala Ser Gln Phe Ser Gln Gly Pro
    1355                1360                1365

Val Pro Gly Thr Cys Ala Asp Trp Ile Pro Gln Ser Ala Ser Cys
    1370                1375                1380

Pro Thr Gly Pro Pro Gln Asn Pro Pro Ser Ala Pro Tyr Cys Gly
    1385                1390                1395

Ile Val Phe Ser Gly Ser Ser Leu Ser Ser Ala Gln Ser Ala Pro
```

```
            1400                1405                1410
Leu Gln His Pro Gly Gly Phe Thr Thr Arg Pro Ser Ala Gly Thr
    1415                1420                1425

Phe Pro Glu Leu Asp Ser Pro Gln Leu His Phe Ser Leu Pro Thr
    1430                1435                1440

Asp Pro Asp Pro Ile Arg Gly Phe Gly Ser Tyr His Pro Ser Ala
    1445                1450                1455

Tyr Ser Pro Phe His Phe Gln Pro Ser Ala Ala Ser Leu Thr Ala
    1460                1465                1470

Asn Leu Arg Leu Pro Met Ala Ser Ala Leu Pro Glu Ala Leu Cys
    1475                1480                1485

Ser Gln Ser Arg Thr Thr Pro Val Asp Leu Cys Leu Leu Glu Glu
    1490                1495                1500

Ser Val Gly Ser Leu Glu Gly Ser Arg Cys Pro Val Phe Ala Phe
    1505                1510                1515

Gln Ser Ser Asp Thr Glu Ser Asp Glu Leu Ser Glu Val Leu Gln
    1520                1525                1530

Asp Ser Cys Phe Leu Gln Ile Lys Cys Asp Thr Lys Asp Asp Ser
    1535                1540                1545

Ile Pro Cys Phe Leu Glu Leu Lys Glu Glu Asp Glu Ile Val Cys
    1550                1555                1560

Thr Gln His Trp Gln Asp Ala Val Pro Trp Thr Glu Leu Leu Ser
    1565                1570                1575

Leu Gln Thr Glu Asp Gly Phe Trp Lys Leu Thr Pro Glu Leu Gly
    1580                1585                1590

Leu Ile Leu Asn Leu Asn Thr Asn Gly Leu His Ser Phe Leu Lys
    1595                1600                1605

Gln Lys Gly Ile Gln Ser Leu Gly Val Lys Gly Arg Glu Cys Leu
    1610                1615                1620

Leu Asp Leu Ile Ala Thr Met Leu Val Leu Gln Phe Ile Arg Thr
    1625                1630                1635

Arg Leu Glu Lys Glu Gly Ile Val Phe Lys Ser Leu Met Lys Met
    1640                1645                1650

Asp Asp Pro Ser Ile Ser Arg Asn Ile Pro Trp Ala Phe Glu Ala
    1655                1660                1665

Ile Lys Gln Ala Ser Glu Trp Val Arg Arg Thr Glu Gly Gln Tyr
    1670                1675                1680

Pro Ser Ile Cys Pro Arg Leu Glu Leu Gly Asn Asp Trp Asp Ser
    1685                1690                1695

Ala Thr Lys Gln Leu Leu Gly Leu Gln Pro Ile Ser Thr Val Ser
    1700                1705                1710

Pro Leu His Arg Val Leu His Tyr Ser Gln Gly
    1715                1720

<210> SEQ ID NO 18
<211> LENGTH: 1014
<212> TYPE: PRT
<213> ORGANISM: Homo sapiens

<400> SEQUENCE: 18

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30
```

```
Leu Arg Met Ala Ile Met Val Gln Ser Pro Met Phe Asp Gly Lys Val
        35                  40                  45
Pro His Trp Tyr His Phe Ser Cys Phe Trp Lys Val Gly His Ser Ile
    50                  55                  60
Arg His Pro Asp Val Glu Val Asp Gly Phe Ser Glu Leu Arg Trp Asp
65                  70                  75                  80
Asp Gln Gln Lys Val Lys Lys Thr Ala Glu Ala Gly Gly Val Thr Gly
                85                  90                  95
Lys Gly Gln Asp Gly Ile Gly Ser Lys Ala Glu Lys Thr Leu Gly Asp
            100                 105                 110
Phe Ala Ala Glu Tyr Ala Lys Ser Asn Arg Ser Thr Cys Lys Gly Cys
            115                 120                 125
Met Glu Lys Ile Glu Lys Gly Gln Val Arg Leu Ser Lys Lys Met Val
        130                 135                 140
Asp Pro Glu Lys Pro Gln Leu Gly Met Ile Asp Arg Trp Tyr His Pro
145                 150                 155                 160
Gly Cys Phe Val Lys Asn Arg Glu Glu Leu Gly Phe Arg Pro Glu Tyr
                165                 170                 175
Ser Ala Ser Gln Leu Lys Gly Phe Ser Leu Leu Ala Thr Glu Asp Lys
            180                 185                 190
Glu Ala Leu Lys Lys Gln Leu Pro Gly Val Lys Ser Glu Gly Lys Arg
        195                 200                 205
Lys Gly Asp Glu Val Asp Gly Val Asp Glu Val Ala Lys Lys Lys Ser
    210                 215                 220
Lys Lys Glu Lys Asp Lys Asp Ser Lys Leu Glu Lys Ala Leu Lys Ala
225                 230                 235                 240
Gln Asn Asp Leu Ile Trp Asn Ile Lys Asp Glu Leu Lys Lys Val Cys
                245                 250                 255
Ser Thr Asn Asp Leu Lys Glu Leu Leu Ile Phe Asn Lys Gln Gln Val
            260                 265                 270
Pro Ser Gly Glu Ser Ala Ile Leu Asp Arg Val Ala Asp Gly Met Val
        275                 280                 285
Phe Gly Ala Leu Leu Pro Cys Glu Glu Cys Ser Gly Gln Leu Val Phe
    290                 295                 300
Lys Ser Asp Ala Tyr Tyr Cys Thr Gly Asp Val Thr Ala Trp Thr Lys
305                 310                 315                 320
Cys Met Val Lys Thr Gln Thr Pro Asn Arg Lys Glu Trp Val Thr Pro
                325                 330                 335
Lys Glu Phe Arg Glu Ile Ser Tyr Leu Lys Lys Leu Lys Val Lys Lys
            340                 345                 350
Gln Asp Arg Ile Phe Pro Pro Glu Thr Ser Ala Ser Val Ala Ala Thr
        355                 360                 365
Pro Pro Pro Ser Thr Ala Ser Ala Pro Ala Ala Val Asn Ser Ser Ala
    370                 375                 380
Ser Ala Asp Lys Pro Leu Ser Asn Met Lys Ile Leu Thr Leu Gly Lys
385                 390                 395                 400
Leu Ser Arg Asn Lys Asp Glu Val Lys Ala Met Ile Glu Lys Leu Gly
                405                 410                 415
Gly Lys Leu Thr Gly Thr Ala Asn Lys Ala Ser Leu Cys Ile Ser Thr
            420                 425                 430
Lys Lys Glu Val Glu Lys Met Asn Lys Lys Met Glu Glu Val Lys Glu
        435                 440                 445
Ala Asn Ile Arg Val Val Ser Glu Asp Phe Leu Gln Asp Val Ser Ala
```

```
            450                 455                 460
Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Gly Ile Asn Lys Ser Glu Lys Arg Met Lys Leu Thr Leu Lys
            515                 520                 525

Gly Gly Ala Ala Val Asp Pro Asp Ser Gly Leu Glu His Ser Ala His
530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu Gln Phe Met Lys Leu Tyr Glu Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
    850                 855                 860

Arg Thr Thr Asn Phe Ala Gly Ile Leu Ser Gln Gly Leu Arg Ile Ala
865                 870                 875                 880
```

```
Pro Pro Glu Ala Pro Val Thr Gly Tyr Met Phe Gly Lys Gly Ile Tyr
            885                 890                 895
Phe Ala Asp Met Val Ser Lys Ser Ala Asn Tyr Tyr His Thr Ser Gln
            900                 905                 910
Gly Asp Pro Ile Gly Leu Ile Leu Leu Gly Glu Val Ala Leu Gly Asn
            915                 920                 925
Met Tyr Glu Leu Lys His Ala Ser His Ile Ser Arg Leu Pro Lys Gly
            930                 935                 940
Lys His Ser Val Lys Gly Leu Gly Lys Thr Thr Pro Asp Pro Ser Ala
945                 950                 955                 960
Asn Ile Ser Leu Asp Gly Val Asp Val Pro Leu Gly Thr Gly Ile Ser
            965                 970                 975
Ser Gly Val Ile Asp Thr Ser Leu Leu Tyr Asn Glu Tyr Ile Val Tyr
            980                 985                 990
Asp Ile Ala Gln Val Asn Leu Lys Tyr Leu Leu Lys Leu Lys Phe Asn
            995                 1000                1005
Phe Lys  Thr Ser Leu Trp
    1010
```

<210> SEQ ID NO 19
<211> LENGTH: 3
<212> TYPE: PRT
<213> ORGANISM: Homo sapiens

<400> SEQUENCE: 19

Tyr Asp Phe
1

<210> SEQ ID NO 20
<211> LENGTH: 7
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid except Pro
<220> FEATURE:
<221> NAME/KEY: MOD_RES
<222> LOCATION: (5)..(6)
<223> OTHER INFORMATION: Any amino acid except Pro

<400> SEQUENCE: 20

Trp Xaa Xaa Pro Xaa Xaa Tyr
1               5

<210> SEQ ID NO 21
<211> LENGTH: 62
<212> TYPE: PRT
<213> ORGANISM: Gallus gallus

<400> SEQUENCE: 21

```
Met Asp Glu Thr Gly Lys Glu Leu Val Leu Ala Leu Tyr Asp Tyr Gln
1               5                   10                  15
Glu Lys Ser Pro Arg Glu Val Thr Met Lys Lys Gly Asp Ile Leu Thr
            20                  25                  30
Leu Leu Asn Ser Thr Asn Lys Asp Trp Trp Lys Val Glu Val Asn Asp
            35                  40                  45
Arg Gln Gly Phe Val Pro Ala Ala Tyr Val Lys Lys Leu Asp
50                  55                  60
```

```
<210> SEQ ID NO 22
<211> LENGTH: 60
<212> TYPE: PRT
<213> ORGANISM: Mus musculus

<400> SEQUENCE: 22
```

Lys Lys Tyr Ala Lys Ser Lys Tyr Asp Phe Val Ala Arg Asn Ser Ser
1               5                   10                  15

Glu Leu Ser Val Met Lys Asp Asp Val Leu Glu Ile Leu Asp Asp Arg
            20                  25                  30

Arg Gln Trp Trp Lys Val Arg Asn Ala Ser Gly Asp Ser Gly Phe Val
        35                  40                  45

Pro Asn Asn Ile Leu Asp Ile Met Arg Thr Pro Glu
    50                  55                  60

```
<210> SEQ ID NO 23
<211> LENGTH: 56
<212> TYPE: PRT
<213> ORGANISM: Homo sapiens

<400> SEQUENCE: 23
```

Met Glu Ala Ile Ala Lys Val Asp Phe Lys Ala Thr Ala Asp Asp Glu
1               5                   10                  15

Leu Ser Phe Lys Arg Gly Asp Ile Leu Lys Val Leu Asn Glu Glu Ser
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys
    50                  55

```
<210> SEQ ID NO 24
<211> LENGTH: 69
<212> TYPE: PRT
<213> ORGANISM: Homo sapiens

<400> SEQUENCE: 24
```

Gly Ser Thr Gly Val Thr Leu Phe Val Ala Leu Tyr Asp Tyr Glu Ala
1               5                   10                  15

Arg Thr Glu Asp Asp Leu Ser Phe His Lys Gly Glu Lys Phe Gln Ile
            20                  25                  30

Leu Asn Ser Ser Glu Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln Ala Glu Glu
65

```
<210> SEQ ID NO 25
<211> LENGTH: 62
<212> TYPE: PRT
<213> ORGANISM: Mus musculus

<400> SEQUENCE: 25
```

Met Asn Asp Pro Asn Leu Phe Val Ala Leu Tyr Asp Phe Val Ala Ser
1               5                   10                  15

Gly Asp Asn Thr Leu Ser Ile Thr Lys Gly Glu Lys Leu Arg Val Leu
            20                  25                  30

Gly Tyr Asn His Asn Gly Glu Trp Cys Glu Ala Gln Thr Lys Asn Gly
        35                  40                  45

```
Gln Gly Trp Val Pro Ser Asn Tyr Ile Thr Pro Val Asn Ser
    50                  55                  60

<210> SEQ ID NO 26
<211> LENGTH: 60
<212> TYPE: PRT
<213> ORGANISM: Homo sapiens

<400> SEQUENCE: 26

Thr Ala Gly Lys Ile Phe Arg Ala Met Tyr Asp Tyr Met Ala Ala Asp
1               5                   10                  15

Ala Asp Glu Val Ser Phe Lys Asp Gly Asp Ala Ile Ile Asn Val Gln
            20                  25                  30

Ala Ile Asp Glu Gly Trp Met Tyr Gly Thr Val Gln Arg Thr Gly Arg
        35                  40                  45

Thr Gly Met Leu Pro Ala Asn Tyr Val Glu Ala Ile
    50                  55                  60

<210> SEQ ID NO 27
<211> LENGTH: 71
<212> TYPE: PRT
<213> ORGANISM: Homo sapiens

<400> SEQUENCE: 27

Asn Lys Gly Val Leu Tyr Ala Leu Trp Asp Tyr Glu Pro Gln Asn Asp
1               5                   10                  15

Asp Glu Leu Pro Met Lys Glu Gly Asp Cys Met Thr Ile Ile His Arg
            20                  25                  30

Glu Asp Glu Asp Glu Ile Glu Trp Trp Trp Ala Arg Leu Asn Asp Lys
        35                  40                  45

Glu Gly Tyr Val Pro Arg Asn Leu Leu Gly Leu Tyr Pro Arg Ile Lys
    50                  55                  60

Pro Arg Gln Arg Ser Leu Ala
65                  70

<210> SEQ ID NO 28
<211> LENGTH: 65
<212> TYPE: PRT
<213> ORGANISM: Mus musculus

<400> SEQUENCE: 28

Asp Arg Val Ala Asp Gly Met Ala Phe Gly Ala Leu Leu Pro Cys Lys
1               5                   10                  15

Glu Cys Ser Gly Gln Leu Val Phe Lys Ser Asp Ala Tyr Tyr Cys Thr
            20                  25                  30

Gly Asp Val Thr Ala Trp Thr Lys Cys Met Val Lys Thr Gln Asn Pro
        35                  40                  45

Ser Arg Lys Glu Trp Val Thr Pro Lys Glu Phe Arg Glu Ile Ser Tyr
    50                  55                  60

Leu
65

<210> SEQ ID NO 29
<211> LENGTH: 65
<212> TYPE: PRT
<213> ORGANISM: Rattus rattus

<400> SEQUENCE: 29

Asp Arg Val Ala Asp Gly Met Ala Phe Gly Ala Leu Leu Pro Cys Lys
1               5                   10                  15
```

```
Glu Cys Ser Gly Gln Leu Val Phe Lys Ser Asp Ala Tyr Tyr Cys Thr
            20                  25                  30

Gly Asp Val Thr Ala Trp Thr Lys Cys Met Val Lys Thr Gln Asn Pro
            35                  40                  45

Ser Arg Lys Glu Trp Val Thr Pro Lys Glu Phe Arg Glu Ile Ser Tyr
        50                  55                  60
Leu
65

<210> SEQ ID NO 30
<211> LENGTH: 65
<212> TYPE: PRT
<213> ORGANISM: Homo sapiens

<400> SEQUENCE: 30

Asp Arg Val Ala Asp Gly Met Val Phe Gly Ala Leu Leu Pro Cys Glu
1               5                   10                  15

Glu Cys Ser Gly Gln Leu Val Phe Lys Ser Asp Ala Tyr Tyr Cys Thr
            20                  25                  30

Gly Asp Val Thr Ala Trp Thr Lys Cys Met Val Lys Thr Gln Thr Pro
            35                  40                  45

Asn Arg Lys Glu Trp Val Thr Pro Lys Glu Phe Arg Glu Ile Ser Tyr
        50                  55                  60
Leu
65

<210> SEQ ID NO 31
<211> LENGTH: 65
<212> TYPE: PRT
<213> ORGANISM: Bos taurus

<400> SEQUENCE: 31

Asp Arg Val Ala Asp Gly Met Val Phe Gly Ala Leu Leu Pro Cys Glu
1               5                   10                  15

Glu Cys Ser Gly Gln Leu Val Phe Lys Gly Asp Ala Tyr Tyr Cys Thr
            20                  25                  30

Gly Asp Val Thr Ala Trp Thr Lys Cys Met Val Lys Thr Gln Thr Pro
            35                  40                  45

Asn Arg Lys Glu Trp Val Thr Pro Lys Glu Phe Arg Glu Ile Ser Tyr
        50                  55                  60
Phe
65

<210> SEQ ID NO 32
<211> LENGTH: 65
<212> TYPE: PRT
<213> ORGANISM: Gallus gallus

<400> SEQUENCE: 32

Asp Arg Val Ala Asp Gly Met Ala Phe Gly Ala Leu Leu Pro Cys Glu
1               5                   10                  15

Glu Cys Lys Gly Gln Phe Val Phe Lys Ser Asp Ala Tyr Tyr Cys Ser
            20                  25                  30

Gly Asp Ile Thr Ala Trp Thr Lys Cys Val Ala Lys Thr Gln Thr Pro
            35                  40                  45

Asn Arg Lys Asp Trp Val Ile Pro Lys Glu Phe Arg Glu Ile Pro Tyr
        50                  55                  60
```

```
Leu
 65

<210> SEQ ID NO 33
<211> LENGTH: 64
<212> TYPE: PRT
<213> ORGANISM: Xenopus laevis

<400> SEQUENCE: 33

Arg Val Ser Asp Gly Met Ala Phe Gly Ala Leu Leu Pro Cys Glu Glu
  1               5                  10                  15

Cys Ser Gly Gln Phe Val Phe Lys Gly Asp Ala Tyr Tyr Cys Thr Gly
             20                  25                  30

Asp Leu Ser Ala Trp Thr Lys Cys Val Ala Lys Thr Gln Thr Pro Asn
         35                  40                  45

Arg Lys Asp Trp Val Thr Pro Lys Glu Phe His Glu Ile Pro Tyr Leu
     50                  55                  60

<210> SEQ ID NO 34
<211> LENGTH: 10
<212> TYPE: PRT
<213> ORGANISM: Homo sapiens

<400> SEQUENCE: 34

Arg Ile Ala Pro Pro Glu Ala Pro Asn Thr
  1               5                  10

<210> SEQ ID NO 35
<211> LENGTH: 10
<212> TYPE: PRT
<213> ORGANISM: Homo sapiens

<400> SEQUENCE: 35

Arg Ile Ala Pro Pro Glu Ala Pro Asn Thr
  1               5                  10

<210> SEQ ID NO 36
<211> LENGTH: 7
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid except Pro
<220> FEATURE:
<221> NAME/KEY: MOD_RES
<222> LOCATION: (5)..(6)
<223> OTHER INFORMATION: Any amino acid except Pro

<400> SEQUENCE: 36

Phe Xaa Xaa Pro Xaa Xaa Tyr
  1               5

<210> SEQ ID NO 37
<211> LENGTH: 1014
<212> TYPE: PRT
<213> ORGANISM: Homo sapiens

<400> SEQUENCE: 37

Met Ala Glu Ser Ser Asp Lys Leu Tyr Arg Val Glu Tyr Ala Lys Ser
  1               5                  10                  15

Gly Arg Ala Ser Cys Lys Lys Cys Ser Glu Ser Ile Pro Lys Asp Ser
             20                  25                  30

Leu Arg Met Ala Ile Met Val Gln Ser Pro Met Phe Asp Gly Lys Val
```

-continued

```
                35                  40                  45
Pro His Trp Tyr His Phe Ser Cys Phe Trp Lys Val Gly His Ser Ile
 50                  55                  60
Arg His Pro Asp Val Glu Val Asp Gly Phe Ser Glu Leu Arg Trp Asp
 65                  70                  75                  80
Asp Gln Gln Lys Val Lys Lys Thr Ala Glu Ala Gly Gly Val Thr Gly
                 85                  90                  95
Lys Gly Gln Asp Gly Ile Gly Ser Lys Ala Glu Lys Thr Leu Gly Asp
                100                 105                 110
Phe Ala Ala Glu Tyr Ala Lys Ser Asn Arg Ser Thr Cys Lys Gly Cys
                115                 120                 125
Met Glu Lys Ile Glu Lys Gly Gln Val Arg Leu Ser Lys Lys Met Val
130                 135                 140
Asp Pro Glu Lys Pro Gln Leu Gly Met Ile Asp Arg Trp Tyr His Pro
145                 150                 155                 160
Gly Cys Phe Val Lys Asn Arg Glu Glu Leu Gly Phe Arg Pro Glu Tyr
                165                 170                 175
Ser Ala Ser Gln Leu Lys Gly Phe Ser Leu Leu Ala Thr Glu Asp Lys
                180                 185                 190
Glu Ala Leu Lys Lys Gln Leu Pro Gly Val Lys Ser Glu Gly Lys Arg
                195                 200                 205
Lys Gly Asp Glu Val Asp Gly Val Asp Glu Val Ala Lys Lys Lys Ser
                210                 215                 220
Lys Lys Glu Lys Asp Lys Asp Ser Lys Leu Glu Lys Ala Leu Lys Ala
225                 230                 235                 240
Gln Asn Asp Leu Ile Trp Asn Ile Lys Asp Glu Leu Lys Lys Val Cys
                245                 250                 255
Ser Thr Asn Asp Leu Lys Glu Leu Leu Ile Phe Asn Lys Gln Gln Val
                260                 265                 270
Pro Ser Gly Glu Ser Ala Ile Leu Asp Arg Val Ala Asp Gly Met Val
                275                 280                 285
Phe Gly Ala Leu Leu Pro Cys Glu Glu Cys Ser Gly Gln Leu Val Phe
290                 295                 300
Lys Ser Asp Ala Tyr Tyr Cys Thr Glu Asp Val Thr Ala Trp Thr Lys
305                 310                 315                 320
Cys Met Val Lys Thr Gln Thr Pro Asn Arg Lys Glu Trp Val Thr Pro
                325                 330                 335
Lys Glu Phe Arg Glu Ile Ser Tyr Leu Lys Lys Leu Lys Val Lys Lys
                340                 345                 350
Gln Asp Arg Ile Phe Pro Pro Glu Thr Ser Ala Ser Val Ala Ala Thr
                355                 360                 365
Pro Pro Pro Ser Thr Ala Ser Ala Pro Ala Ala Val Asn Ser Ser Ala
370                 375                 380
Ser Ala Asp Lys Pro Leu Ser Asn Met Lys Ile Leu Thr Leu Gly Lys
385                 390                 395                 400
Leu Ser Arg Asn Lys Asp Glu Val Lys Ala Met Ile Glu Lys Leu Gly
                405                 410                 415
Gly Lys Leu Thr Gly Thr Ala Asn Lys Ala Ser Leu Cys Ile Ser Thr
                420                 425                 430
Lys Lys Glu Val Glu Lys Met Asn Lys Lys Met Glu Glu Val Lys Glu
                435                 440                 445
Ala Asn Ile Arg Val Val Ser Glu Asp Phe Leu Gln Asp Val Ser Ala
450                 455                 460
```

```
Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
        485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
            515                 520                 525

Gly Gly Ala Ala Val Asp Pro Asp Ser Gly Leu Glu His Ser Ala His
530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
            565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu Gln Phe Met Lys Leu Tyr Glu Glu Lys Thr Gly Asn
610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
            645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
        690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
            725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
            805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
        850                 855                 860

Arg Thr Thr Asn Phe Ala Gly Ile Leu Ser Gln Gly Leu Arg Ile Ala
865                 870                 875                 880
```

```
Pro Pro Glu Ala Pro Val Thr Gly Tyr Met Phe Gly Lys Gly Ile Tyr
            885                 890                 895

Phe Ala Asp Met Val Ser Lys Ser Ala Asn Tyr Tyr His Thr Ser Gln
            900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Arg Leu Pro Lys Gly
        930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Ile Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
            995                 1000                1005

Phe Lys Thr Ser Leu Trp
    1010
```

<210> SEQ ID NO 38
<211> LENGTH: 1014
<212> TYPE: PRT
<213> ORGANISM: Homo sapiens

<400> SEQUENCE: 38

```
Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240
```

```
Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Met Glu Glu Val Lys Glu
        435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu Gln Phe Met Lys Leu Tyr Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655
```

```
Val Asn Pro Gly Thr Lys Ser Lys Leu Pro Lys Pro Val Gln Asp Leu
        660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
        690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
        740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
        770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Ser Ala Tyr Asp Leu Glu
        820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
        850                 855                 860

Arg Thr Thr Asn Phe Ala Gly Ile Leu Ser Gln Gly Leu Arg Ile Ala
865                 870                 875                 880

Ala Pro Glu Ala Pro Val Thr Gly Tyr Met Phe Gly Lys Gly Ile Tyr
                885                 890                 895

Phe Ala Asp Met Val Ser Lys Ser Ala Asn Tyr Tyr His Thr Ser Gln
                900                 905                 910

Gly Asp Pro Ile Gly Leu Ile Leu Leu Gly Glu Val Ala Leu Gly Asn
        915                 920                 925

Met Tyr Glu Leu Lys His Ala Ser His Ile Ser Arg Leu Pro Lys Gly
        930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Ile Asp Thr Ser Leu Leu Tyr Asn Glu Tyr Ile Val Tyr
                980                 985                 990

Asp Ile Ala Gln Val Asn Leu Lys Tyr Leu Leu Lys Leu Lys Phe Asn
        995                 1000                1005

Phe Lys Thr Ser Leu Trp
    1010

<210> SEQ ID NO 39
<211> LENGTH: 1014
<212> TYPE: PRT
<213> ORGANISM: Homo sapiens

<400> SEQUENCE: 39

Met Ala Glu Ser Ser Asp Lys Leu Tyr Arg Val Glu Tyr Ala Lys Ser
1               5                   10                  15
```

```
Gly Arg Ala Ser Cys Lys Lys Cys Ser Glu Ser Ile Pro Lys Asp Ser
             20                  25                  30

Leu Arg Met Ala Ile Met Val Gln Ser Pro Met Phe Asp Gly Lys Val
         35                  40                  45

Pro His Trp Tyr His Phe Ser Cys Phe Trp Lys Val Gly His Ser Ile
     50                  55                  60

Arg His Pro Asp Val Glu Val Asp Gly Phe Ser Glu Leu Arg Trp Asp
 65                  70                  75                  80

Asp Gln Gln Lys Val Lys Lys Thr Ala Glu Ala Gly Gly Val Thr Gly
                 85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Val Arg Leu Ser Lys Lys Met Val
            130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
            195                 200                 205

Lys Gly Asp Glu Val Asp Gly Val Asp Glu Val Ala Lys Lys Lys Ser
            210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
            275                 280                 285

Phe Gly Ala Leu Leu Pro Cys Glu Glu Cys Ser Gly Gln Leu Val Phe
290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
            355                 360                 365

Pro Pro Pro Ser Thr Ala Ser Ala Pro Ala Ala Val Asn Ser Ser Ala
370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430
```

-continued

```
Lys Lys Glu Val Glu Lys Met Asn Lys Met Glu Val Lys Glu
        435                 440                 445

Ala Asn Ile Arg Val Val Ser Glu Asp Phe Leu Gln Asp Val Ser Ala
        450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
                500                 505                 510

Glu Glu Gly Ile Asn Lys Ser Glu Lys Arg Met Lys Leu Thr Leu Lys
            515                 520                 525

Gly Gly Ala Ala Val Asp Pro Asp Ser Gly Leu Glu His Ser Ala His
        530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
                580                 585                 590

Gly Thr Val Ile Gly Ser Asn Lys Leu Glu Gln Met Pro Ser Lys Glu
            595                 600                 605

Asp Ala Ile Glu Gln Phe Met Lys Leu Tyr Glu Glu Lys Thr Gly Asn
        610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
        690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
        770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
```

-continued

```
             850                 855                 860
Arg Thr Thr Asn Phe Ala Gly Ile Leu Ser Gln Gly Leu Arg Ile Ala
865                 870                 875                 880

Pro Ala Glu Ala Pro Val Thr Gly Tyr Met Phe Gly Lys Gly Ile Tyr
                885                 890                 895

Phe Ala Asp Met Val Ser Lys Ser Ala Asn Tyr Tyr His Thr Ser Gln
                900                 905                 910

Gly Asp Pro Ile Gly Leu Ile Leu Leu Gly Glu Val Ala Leu Gly Asn
                915                 920                 925

Met Tyr Glu Leu Lys His Ala Ser His Ile Ser Arg Leu Pro Lys Gly
            930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Ile Asp Thr Ser Leu Leu Tyr Asn Glu Tyr Ile Val Tyr
                980                 985                 990

Asp Ile Ala Gln Val Asn Leu Lys  Tyr Leu Leu Lys Leu  Lys Phe Asn
                995                 1000                1005

Phe Lys  Thr Ser Leu Trp
    1010
```

<210> SEQ ID NO 40
<211> LENGTH: 1014
<212> TYPE: PRT
<213> ORGANISM: Homo sapiens

<400> SEQUENCE: 40

```
Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205
```

```
Lys Gly Asp Glu Val Asp Gly Val Asp Glu Val Ala Lys Lys Ser
    210             215             220

Lys Lys Glu Lys Asp Lys Asp Ser Lys Leu Glu Lys Ala Leu Lys Ala
225             230             235             240

Gln Asn Asp Leu Ile Trp Asn Ile Lys Asp Glu Leu Lys Lys Val Cys
            245             250             255

Ser Thr Asn Asp Leu Lys Glu Leu Leu Ile Phe Asn Lys Gln Gln Val
        260             265             270

Pro Ser Gly Glu Ser Ala Ile Leu Asp Arg Val Ala Asp Gly Met Val
    275             280             285

Phe Gly Ala Leu Leu Pro Cys Glu Cys Ser Gly Gln Leu Val Phe
    290             295             300

Lys Ser Asp Ala Tyr Tyr Cys Thr Gly Asp Val Thr Ala Trp Thr Lys
305             310             315             320

Cys Met Val Lys Thr Gln Thr Pro Asn Arg Lys Glu Trp Val Thr Pro
            325             330             335

Lys Glu Phe Arg Glu Ile Ser Tyr Leu Lys Lys Leu Lys Val Lys Lys
        340             345             350

Gln Asp Arg Ile Phe Pro Pro Glu Thr Ser Ala Ser Val Ala Ala Thr
    355             360             365

Pro Pro Pro Ser Thr Ala Ser Ala Pro Ala Ala Val Asn Ser Ser Ala
370             375             380

Ser Ala Asp Lys Pro Leu Ser Asn Met Lys Ile Leu Thr Leu Gly Lys
385             390             395             400

Leu Ser Arg Asn Lys Asp Glu Val Lys Ala Met Ile Glu Lys Leu Gly
            405             410             415

Gly Lys Leu Thr Gly Thr Ala Asn Lys Ala Ser Leu Cys Ile Ser Thr
        420             425             430

Lys Lys Glu Val Glu Lys Met Asn Lys Lys Met Glu Glu Val Lys Glu
    435             440             445

Ala Asn Ile Arg Val Val Ser Glu Asp Phe Leu Gln Asp Val Ser Ala
450             455             460

Ser Thr Lys Ser Leu Gln Glu Leu Phe Leu Ala His Ile Leu Ser Pro
465             470             475             480

Trp Gly Ala Glu Val Lys Ala Glu Pro Val Glu Val Ala Pro Arg
            485             490             495

Gly Lys Ser Gly Ala Ala Leu Ser Lys Lys Ser Lys Gly Gln Val Lys
        500             505             510

Glu Glu Gly Ile Asn Lys Ser Glu Lys Arg Met Lys Leu Thr Leu Lys
    515             520             525

Gly Gly Ala Ala Val Asp Pro Asp Ser Gly Leu Glu His Ser Ala His
530             535             540

Val Leu Glu Lys Gly Gly Lys Val Phe Ser Ala Thr Leu Gly Leu Val
545             550             555             560

Asp Ile Val Lys Gly Thr Asn Ser Tyr Tyr Lys Leu Gln Leu Leu Glu
            565             570             575

Asp Asp Lys Glu Asn Arg Tyr Trp Ile Phe Arg Ser Trp Gly Arg Val
        580             585             590

Gly Thr Val Ile Gly Ser Asn Lys Leu Glu Gln Met Pro Ser Lys Glu
    595             600             605

Asp Ala Ile Glu Gln Phe Met Lys Leu Tyr Glu Glu Lys Thr Gly Asn
610             615             620

Ala Trp His Ser Lys Asn Phe Thr Lys Tyr Pro Lys Lys Phe Tyr Pro
```

-continued

```
            625                 630                 635                 640

Leu Glu Ile Asp Tyr Gly Gln Asp Glu Glu Ala Val Lys Lys Leu Thr
                    645                 650                 655

Val Asn Pro Gly Thr Lys Ser Lys Leu Pro Lys Pro Val Gln Asp Leu
                660                 665                 670

Ile Lys Met Ile Phe Asp Val Glu Ser Met Lys Lys Ala Met Val Glu
            675                 680                 685

Tyr Glu Ile Asp Leu Gln Lys Met Pro Leu Gly Lys Leu Ser Lys Arg
        690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
                740                 745                 750

Asn Asn Ala Asp Ser Val Gln Ala Lys Val Glu Met Leu Asp Asn Leu
                755                 760                 765

Leu Asp Ile Glu Val Ala Tyr Ser Leu Leu Arg Gly Gly Ser Asp Asp
            770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
    850                 855                 860

Arg Thr Thr Asn Phe Ala Gly Ile Leu Ser Gln Gly Leu Arg Ile Ala
865                 870                 875                 880

Pro Pro Glu Ala Ala Val Thr Gly Tyr Met Phe Gly Lys Gly Ile Tyr
                885                 890                 895

Phe Ala Asp Met Val Ser Lys Ser Ala Asn Tyr Tyr His Thr Ser Gln
                900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Arg Leu Pro Lys Gly
        930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Ile Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
        995                 1000                1005

Phe Lys Thr Ser Leu Trp
    1010
```

<210> SEQ ID NO 41
<211> LENGTH: 16
<212> TYPE: PRT
<213> ORGANISM: Homo sapiens

<400> SEQUENCE: 41

Gly Leu Arg Ile Ala Pro Pro Glu Ala Pro Val Thr Gly Tyr Met Phe
1               5                   10                  15

<210> SEQ ID NO 42
<211> LENGTH: 16
<212> TYPE: PRT
<213> ORGANISM: Mus musculus

<400> SEQUENCE: 42

Gly Leu Arg Ile Ala Pro Pro Glu Ala Pro Val Thr Gly Tyr Met Phe
1               5                   10                  15

<210> SEQ ID NO 43
<211> LENGTH: 16
<212> TYPE: PRT
<213> ORGANISM: Rattus rattus

<400> SEQUENCE: 43

Gly Leu Arg Ile Ala Pro Pro Glu Ala Pro Val Thr Gly Tyr Met Phe
1               5                   10                  15

<210> SEQ ID NO 44
<211> LENGTH: 16
<212> TYPE: PRT
<213> ORGANISM: Homo sapiens

<400> SEQUENCE: 44

Gly Leu Arg Ile Ala His Pro Glu Ala Pro Ile Thr Gly Tyr Met Phe
1               5                   10                  15

<210> SEQ ID NO 45
<211> LENGTH: 16
<212> TYPE: PRT
<213> ORGANISM: Mus musculus

<400> SEQUENCE: 45

Gly Leu Arg Val Ala Pro Pro Glu Ala Pro Ile Thr Gly Tyr Met Phe
1               5                   10                  15

<210> SEQ ID NO 46
<211> LENGTH: 12
<212> TYPE: PRT
<213> ORGANISM: Homo sapiens

<400> SEQUENCE: 46

Gly Leu Arg Ile Met Pro His Ser Gly Gly Arg Val
1               5                   10

<210> SEQ ID NO 47
<211> LENGTH: 13
<212> TYPE: PRT
<213> ORGANISM: Homo sapiens

<400> SEQUENCE: 47

Gly Phe Asp Glu Arg His Ala Tyr Ile Gly Gly Met Phe
1               5                   10

<210> SEQ ID NO 48
<211> LENGTH: 21
<212> TYPE: PRT
<213> ORGANISM: Homo sapiens

<400> SEQUENCE: 48

-continued

```
Ala Pro Pro Gly Tyr Asp Ser Val His Gly Val Ser Gln Thr Ala Ser
1               5                   10                  15

Val Thr Thr Asp Phe
            20
```

SELECTIVE PARP-1 TARGETING FOR DESIGNING CHEMO/RADIO SENSITIZING AGENTS

CLAIM OF PRIORITY

This application claims priority from U.S. provisional patent application Ser. No. 60/296,110, filed Jun. 7, 2001.

FIELD OF THE INVENTION

The invention relates generally to cancer treatment, and in particular to overcoming cellular resistance to antitumor agents.

BACKGROUND OF THE INVENTION

DNA repair is a mechanism of resistance to antitumor DNA damaging agents and to radiotherapy. Rosen EM et al., *Cancer Invest.* 17(1): 56–72 (1999). The ability of cancer cells to recognize and repair DNA damage inflicted by cancer therapy is an important mechanism of resistance to treatment. Thus, inhibition of DNA repair is a key strategy in enabling cancer therapy.

Activation of the poly(ADP-ribose) polymerase-1 (PARP-1) enzyme is an immediate cellular response to genotoxic stress and is part of a genomic surveillance mechanism that responds to DNA damage, triggering signaling events that can lead to cellular recovery. PARP-1 is specifically activated by binding to DNA strand breaks. PARP-1 has been shown to be a target for the development of radio and chemo sensitizing agents in cancer treatment as well as providing protection from stroke. Szabo C & Dawson V L, *Trends Pharmacol Sci.* 19(7): 287–98 (1998). Current inhibitors target a conserved catalytic domain of poly(ADP-Ribose) polymerase-1 (PARP-1) present in all of the PARP family members. Ruf A. et al., *Biochemistry* 37(11): 3893–900 (1998); Tentori L et al., *Pharmacol Res.* 45(2): 73–85 (2002); Jacobson M K & Jacobson E L, Trends Biochem Sci. 24(11): 415–7 (1999).

Knockout experiments have shown that the therapeutic benefits of PARP-1 inhibition are a direct result of the selective inhibition of PARP-1. Shall S & de Murcia G, *Mutat. Res.* 4601: 1–15 (2000). Although PARP-1 knockout is not lethal, it leads to genomic instability and enhances the cytotoxicity of DNA damaging agents used in cancer therapy. Several PARP-1 inhibitors are currently in preclinical development for cancer therapy. Each of these inhibitors targets the binding site of the required substrate of the enzyme, nicotinamide adenine dinucleotide (NAD). White A W et al., *J. Med. Chem.* 43: 4084–97 (2000).

Until recently, PARP-1 was the only known enzyme with ADP-ribose polymerizing activity. PARP-1 has now been found to be one of a family of enzymes with PARP activity. Jacobson M K & Jacobson E L, *Trends Biochem. Sci.* 24: 415–7 (1999). Amino acid sequence comparisons of the members of the PARP family indicate that there is similarity in their NAD binding sites (pADPRT domain, see, FIG. 1A). Thus, the current inhibitors lack selectivity, because they target an NAD binding site common to all PARP family members.

A double knockout of PARP-1 and PARP-2 results in an embryonic lethal. Schreiber V. et al., *J. Biol. Chem.* (2002). PARP-1 inhibitors have also inhibit PARP-2, thus it is likely that the current strategy of inhibitor design may lead to toxic effects. Perkins E. et al., Cancer Res. 61(10): 4175–83 (2001).

Thus, while PARP-1 remains a promising therapeutic target, the discovery of multiple PARPs raises questions of inhibitor selectivity not heretofore considered.

SUMMARY OF THE INVENTION

The invention provides the identification of a Src-homology 3 (SH3) domain (domain C; SEQ ID NO: 1) and an SH3 ligand domain (PXXP motif) (SEQ ID NO: 2) on the poly(ADP-ribose) polymerase-1 (PARP-1) protein (SEQ ID NOS: 4 and 6). The invention also provides that these domains are involved in PARP-1 activation. The mechanism of PARP-1 activation resembles that of src-tyrosine kinase activation. Accordingly, the invention provides new methods for selectively targeting the SH3 domain of PARP-1.

The overall importance of this invention is a new understanding of the structural mechanisms of enzymes involved in poly ADP-ribosylation and the utilization of this new information in the design of selective inhibitors of the PARP-1 enzyme. Thus, the invention involves a paradigm shift in the design of inhibitors for this anticancer target.

In one embodiment, the invention provides a method for identifying agents that activate PARP-1, including the steps of:
(a) contacting a test compound with PARP-1 or a functional fragment thereof, wherein the functional fragment contains the PARP-1 SH-3 domain, the PARP-1 SH3-ligand domain, or both domains;
(b) assaying whether contacting the compound results in activation of PARP-1; and
(c) identifying the test compound as a compound that activates PARP-1.

In another embodiment, the invention provides a method for identifying agents that inactivate PARP-1, including the steps of:
(a) contacting a test compound with PARP-1 or a functional fragment thereof, wherein the functional fragment contains the PARP-1 SH-3 domain, the PARP-1 SH3-ligand domain, or both domains;
(b) assaying whether contacting the compound results in inactivation or prevents activation of PARP-1; and
(c) identifying the test compound as a compound that inactivates or prevents activation of PARP-1.

In yet another embodiment, the invention provides a method for designing PARP-1 inhibitors, including the steps of
a) providing the structure of the PARP-1 SH-3 domain or the PARP-1 SH3-ligand domain in a digital format that can be used by a molecular modeling computer program;
b) obtaining the structure of a compound suspected of molecularly interacting with the PARP-1 SH-3 domain or the PARP-1 SH3-ligand domain;
c) providing the structure of the compound suspected of molecularly interacting with the PARP-1 SH-3 domain or the PARP-1 SH3-ligand domain in a digital format that can be used by the molecular modeling computer program;
d) operating the molecular modeling computer program to determine
(i) whether the PARP-1 SH-3 domain molecularly interacts with the compound suspected of molecularly interacting with the PARP-1 SH-3 domain, or
(ii) whether the PARP-1 SH3-ligand domain molecularly interacts with the compound suspected of molecularly interacting with the PARP-1 SH3-ligand domain; and (e) identifying a compound that interacts molecularly as a potential therapeutic agent.

In a specific embodiment, small peptides with the sequence RIAPEAPV (SEQ ID NO: 7) compete with the natural ligand of PARP-1 protein to affect PARP-1 activity.

BRIEF DESCRIPTION OF THE DRAWINGS

FIG. 1A shows the overall domain organization of PARP family members, PARP-1 (SEQ ID NOS: 4 and 6); PARP-2 (SEQ ID NOS: 9 and 11); PARP-3 (SEQ ID NO: 13); tankyrase (SEQ ID NO: 15) and vault-PARP (SEQ ID NO: 17). All PARPs contain a conserved poly ADP-ribosylation domain. Some also contain a DNA binding domain (A, A', A") and protein interaction domains (D, G). The conserved ADPRT-fold also found in bacterial toxins (domain F) is shown in the ribbon diagram of the structure of CF-PARP-1. As provided in this invention, PARP-1 contains a SH3 domain (C) and SH3 ligand. FIG. 1B shows the activation mechanism of PARP-1 described in this application, involving the formation of a PARP-1 homodimer through the intermolecular interaction of an SH3 and SH3 ligand domains.

FIG. 6 is a sequence alignment of a select group of SH3 domains (top 7 sequences) whose structures have been determined and deposited in the PDB database (first three letters of the sequence identification indicates the PDB code): 1AEY (SEQ ID NO: 21); 1AOJ_A (SEQ ID NO: 22); 1AZE_A (SEQ ID NO: 23); 1A0N_B (SEQ ID NO: 24); 1ABO_A (SEQ ID NO: 25); 1ARK (SEQ ID NO: 26); P53BP (SEQ ID NO: 29). The bottom 6 sequences are those from the C domain of PARP-1 from mouse (P_mussh3; SEQ ID NO: 28), rat (P_ratsh3; SEQ ID NO: 29), human (P_humsh3; SEQ ID NO: 30), bovine (P_bovsh3; SEQ ID NO: 31), chicken (P_chksh3; SEQ ID NO: 32) and Xenopus (P_xensh3; SEQ ID NO: 33).

DETAILED DESCRIPTION OF THE INVENTION

PARP-1 and the unique post-translational modification it catalyzes have previously been considered to function only in the cellular surveillance of genotoxic stress. However, the recent identification of multiple members of a PARP family might force a revision and expansion of this concept.

Figure 1:
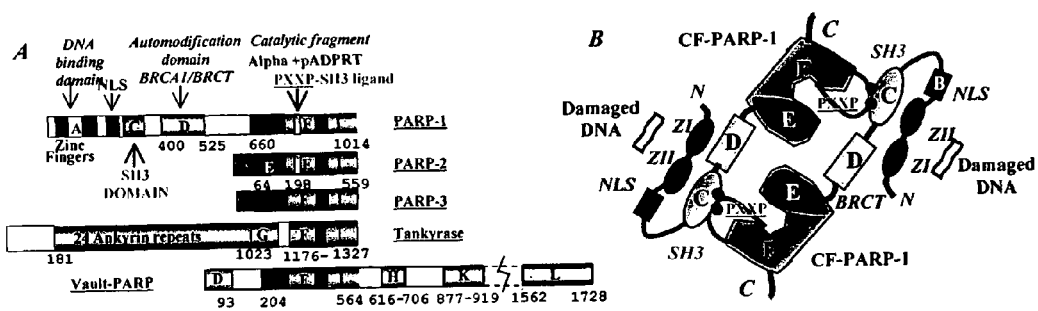
FIG. 1 is a set of graphic representations of enzymes in the PARP family.

PARP-1 is a unique 114 kDa multidomain biosensor that recognizes DNA strand breaks introduced in the genome of eukaryotic cells exposed to radiation or genotoxic agents. The recognition of DNA nicks by two zinc fingers domains of PARP-1 (domain A, FIG. 1), found at its N-terminus, triggers the activity of the catalytic of CF-PARP-1 (domain E+F, FIG. 1) by 500-fold. PARP-1 attaches ADP-ribose (ADPR) to itself (domain D, FIG. 1A) and a growing array of nuclear protein acceptors using nicotinamide adenine dinucleotide (NAD) as a substrate. PARP-1 synthesizes ADP-ribose polymers from $NAD^+$ by attaching $NAD^+$ to glutamic acid of acceptor proteins such as histones, P53 and proteins involved in the formation of DNA repair complexes, such as the Base Excision repair complex (BASC), DNA polβ and XRCC1. The NAD is covalently linked to the terminal ADP-ribose moiety of the elongating ADP-ribose polymer. Ruf A et al., *Proc. Natl. Acad. Sci. USA* 93(15): 7481–5 (1996).

The active site of all PARPs contain a conserved glutamic acid residue which enables a nucleophilic attack on the glycosidic bond to the nicotinamide portion of NAD by the 2' hydroxyl of the terminal ADPR unit of the terminal polymer. The adenine portion of NAD binds in a deep pocket of the CF-PARP-1 structure, while the nicotinamide portion of NAD binds in a shallow cavity.

The use of $NAD^+$ as a substrate by PARP-1 establishes a link between poly ADP-ribosylation and the energy status of the cell. In situations of massive DNA damage, PARP-1 is hyperactivated. $NAD^+$ depletion follows, resulting in cellular necrosis. Thus, regulation of PARP-1 activity is at a crucial intersection in the cellular fate.

The observation that there is essentially no detectable poly(ADP-ribose) in resting cells suggests that PARPs are generally inactive and, therefore, tightly regulated in vivo. Smith S, *Trends Biochem. Sci.* 26: 174–179 (2001).

Cancer cells are able to evade programmed cell death (apoptosis) by a mechanism that involves PARP-1 inactivation through cleavage by Caspase-3. Smulson M E et al., *Adv. Enzyme Regul.* 40: 183–215 (2000). Consequently, cancer cells retain the ability to signal DNA repair in response to single strand breaks. PARP-1 inhibition in cancer cells mimics its apoptotic inactivation and disables recovery of cancer cells exposed to radiologic or chemotherapeutic agents.

Current inhibitors of PARP-1 have targeted the catalytic fragment of PARP-1, which contains an NAD binding site. Bousquet J A et al., *Biochemistry* 39: 7722–35 (2000). The current inhibitors of PARP-1 are derivatives of benzamides and fused ring heterocycles that bind to the nicotinamide cavity and inhibit PARP-1 by competing with NAD substrate. U.S. Pat. Nos. 6,201,020, 6,121,278, 5,587,384, 5,215,738; 5,041,653 and 5,032,617. However, because all PARPs contain this conserved binding, the current PARP-1 inhibitors lack selectivity.

This invention addresses this selectivity issue by providing an understanding of the mechanism of PARP-1 activation, at the molecular level. As described below, the invention puts forward the involvement of an SH3 domain (domain C, FIG. 1; SEQ ID NO: 1) and an SH3-ligand domain (PXXP motif; SEQ ID NO: 2).

This invention provides a paradigm shift in the design of PARP-1 inhibitors, where the molecular target is a protein interaction interface involved in triggering PARP-1 activity once PARP-1 recognizes damaged DNA, rather than the $NAD^+$ binding site, where all current inhibitor effort has been focused. As described below, PARP-1 activation resulting from DNA strand break recognition results from the action of an SH3 protein interaction module on PARP-1 that potentiates the catalytic dimer. Accordingly, the present invention provides for the development of a new drug discovery paradigm for generation of PARP-1 inhibitors for cancer therapy, by affecting function by allosteric mechanisms. DeDecker B S, *Chem. Biol.* 7(5): R103–7 (2000).

Poly(ADP-ribose) polymerase-1 (PARP-1) is a Key Biosynthetic Target for Drug Discovery. The PARP-1 enzyme has been purified and the gene has been characterized. Cherney B W et al., *Proc. Natl. Acad. Sci. USA* 84(23): 8370–4 (1987); Kurosaki T et al., *J. Biol. Chem.* 262(33): 15990–7 (1987); Uchida K et al., *Biochem. Biophys. Res. Commun.* 148(2): 617–22 (1987); Auer B et al., *DNA* 8(8): 575–80 (1989). The availability of this information led to further developments: (1) structural and site directed mutagenesis studies enabling the definition of several functional domains including two zinc finger domains at the N-terminal (FIG. 1A) that bind to DNA strand breaks, an internal automodification domain similar to that found in the C-terminus of the breast cancer gene (BRCT domain), and a C-terminal catalytic fragment containing a conserved $NAD^+$; (2) the generation of PARP-1 "knockout" mice that, despite having a normal development and the capability of generating ADPR polymers, are very sensitive to genotoxic stress and have a shorter life span; (3) the detection of the cleavage of PARP-1 by caspases at the DED sequence motif found at the very end of the zinc finger domain (Nicholson, D W et al., *Nature* 376(6535): 37–43 (1995)); (4) the structural determination of the catalytic domain of PARP-1 (CF-PARP-1) (Ruf, A et al., *Proc. Natl. Acad. Sci. USA* 93(15): 7481–5 (1996)), which has structural homology to the ADP-ribosyl transfer (ADPRT) domain of diphtheria, cholera, pertussis and enterotoxins; and (5) the identification of PARP-1 inhibitors, targeting the shallow nicotinamide pocket, and used in cancer therapy as radio and chemosensitizing agents. White A W et al., *J. Med. Chem.* 43(22): 4084–97 (2000); Schlicker A et al., *Int. J. Radiat. Biol.* 75(1): 91–100 (1999)).

Thus, PARP-1 functions as a cellular biosensor of DNA strands breaks, triggering the poly ADP-ribosylation of chromatin and DNA repair proteins. The recognition of strand breaks results in at least a 200-fold increase in enzyme activity. The catalytic domain serves two functions: (1) automodification of PARP at conserved glutamate residues localized in the BRCT domain, through the formation of dimers. Mendoza-Alvarez H & Alvarez-Gonzalez R, *J. Biol. Chem.* 268(30): 22575–80 (1993); and (2) the ADP-ribosylation of other protein acceptors including histones and DNA-repair complexes. The ADP-ribosylation of histones by PARP is thought to be an important step in chromatin decondensation, which may be part of an overall mechanism of freeing the damaged DNA while at the same time recruiting the action of DNA repair complexes.

PARP-1 is a Member of a New Family of Poly ADP-Ribosylating Proteins. The development of PARP-1 knockout mice revealed that polymer metabolism was not disrupted in PARP-1 knockout mice. Shieh W M et al., *J. Biol. Chem.* 273(46): 30069–72 (1998). This information suggested functional redundancy in the production of poly (ADP-ribose). Two closely related PARPs (PARP-2 (SEQ ID NOS: 9 and 11) and PARP-3 (SEQ ID NO: 13)) were identified in human and *Drosophila*. Johansson M, *Genomics* 57(3): 442–5 (1999); Ame J C et al, *J. Biol. Chem.* 274(25): 17860–8 (1999); Kawamura T et al., *Biochem. Biophys. Res. Commun.* 251(1): p. 35–40 (1998).

The first new PARP member identified was tankyrase (Smith S et al., *Science* 282(5393): 1484–7 (1998)), also a multidomain protein containing the protein interaction modules ankyrin repeats and SAM domains (SEQ ID NO: 15). Tankyrase is responsible for the ADP-ribosylation of TRF1, a protein involved in the assembly and disassembly of the T-loop structure found at the ends of the chromosomes. Tankyrase serves to regulate the function of TRF1 and thus, is a potentially new target for inhibiting the action of telomerase in cancer cells.

The second new member of the PARP family identified was vault PARP (SEQ ID NO: 17). Kickhoefer V A et al., *J. Cell Biol.* 146(5): 917–28 (1999). Vault PARP is also a multidomain protein containing the BCRT protein interaction domain, present in PARP-1 and several DNA repair proteins. Vault PARP is a large protein-RNA complex found in the cytoplasm, and currently thought to mediate the transport of mRNA.

Figure 4:
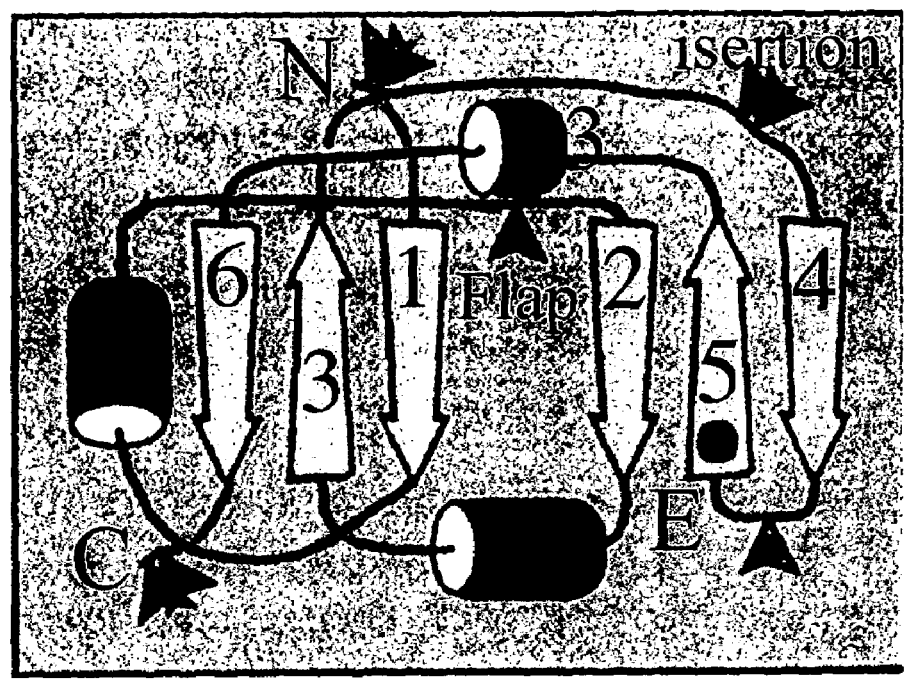
FIG. 4 shows the structure of CF-PARP-1 and its inhibitor complexes. The NAD substrate binding site (donor site) with the adenine moiety binding is in a deep pocket, while the nicotinamide portion is localized in a shallow pocket next to the terminal ADP-ribose unit of the polymer (acceptor site).

The single conserved domain found in all PARPs is a catalytic fragment of PARP-1 (CF-PARP-1). The structure of CF-PARP-1 was recently determined by Ruf et al., *Proc. Natl. Acad. Sci. USA* 93(15): 7481–5 (1996), and revealed a conserved ADP-ribosyltransferase domain (ADPRT, domain F) core structure also found in bacterial toxins. Like ADPRTs, PARP contains an $NAD^+$ recognition site. A detailed comparison of the structure of PARP with the toxins showed a conserved catalytic glutamic acid at the beginning of the fifth stand ($\beta 5$) of the ADPRT fold (see, FIG. 4).

PARP Activation Requires Self-association. The relationship between the oligomeric state of PARP-1 and its activation has been investigated by several techniques, including sedimentation equilibrium, gel permeation, electrophoretic mobility and kinetics measurements. Juarez-Salinas H et al., *Anal. Biochem.* 131(2): 410–8 (1983). PARP-1 in its activated form is a homodimer, but the structural elements required for dimerization remain unknown. The presence of the protein interaction domain, BRCT, suggests that BRCT may potentiate dimerization. BRCT domains are found in several DNA repair proteins leading to the formation of the BRCA-associated genome surveillance complex or BASC and the DNA-base excision complex (BEC). PARP-1 may have a regulatory/assembly function in the formation of these complexes through ADP-ribosylation.

The structure of *Drosophila* PARP-1 suggested that PARP-1 protein interactions occurred through a conserved leucine zipper at the N-terminus of the BRCT domain. Uchida K et al., *Proc. Natl. Acad. Sci. USA* 90(8): p. 3481–5 (1993). Evidence in support of this model include: (1) the C-terminal apoptotic cleavage product (lacking only the zinc finger domains) inhibits dimerization and consequently PARP-1 activation (Kim, J W et al., *J. Biol. Chem.* 275(11): 8121–5 (2000)); and (2) deletion mutant analyses of PARP-1 have been used to map the dimerization domain to the vicinity of the BRCT domain containing the putative leucine zipper motif. The recent structural determination of the BRCT domain of XRCC1 (Marintchev A et al., *Nat. Struct. Biol.* 6(9): 884–93 (1999)) and sequence alignment of the BRCT family, including PARP-1-BRCT (Bork P et al., *FASEB J.* 11(1): 68–76 (1997)), maps the putative leucine zipper motif to a surface-exposed N-terminal helix (α1) of this α/β structure. In the crystal structure of XRCC1, the BRCT domain helix α1 was found to be involved in homodimerization and was proposed to mediate protein interactions in vivo.

SH3 Protein Interaction Modules and Enzyme Activation. Many proteins, including the src family of tyrosine kinases, are regulated by the interaction of SH3 and SH3-ligand domains. Dalgarno D C et al. *Biopolymers* 43: 383–400 (1997).

Cells use protein interaction modules (SH2, SH3, EH, PDZ, WW, PTB) in the recruitment of active molecules into multiprotein signal complexes or in the activation of dormant enzymes. One of these interaction modules is the SH3 domain that binds to proline-rich peptide sequences with the consensus sequence, PXXP (SEQ ID NO: 2), which forms a left-handed polyproline type II helix (PPII). Kuriyan J & Cowburn D, *Annu. Rev. Biophys. Biomol. Struct.* 26: 259–88 (1997). The name SH3 stands for the conserved Src-homology domain 3 found in Src-family tyrosine kinases. Along with the SH2 domain, SH3 domains regulate the activation and the localization targeting of Src-kinases. Williams J C et al., *Trends Biochem. Sci.* 23(5): 179–84 (1998). The SH3 domain is a small (~60 residues) domain with over 250 representative sequences in the SWISSPROT database (SEQ ID NO: 1). All SH3 domains fold into a compact structure made up of two anti-parallel beta sheets of four stands connected by loops of varying sizes (RT-loop and n-src loop, see, FIG. 4). The general peptide-binding surface of the SH3 module is made up of a cluster of aromatic residues, forming three pockets. The two prolines of the core motif PXXP (the SH3-ligand; SEQ ID NO: 2) bind to two hydrophobic pockets containing conserved aromatic residues, while a third pocket is usually lined up with negative charges and usually interacts with a positively charged residue of the ligand. Kardinal C et al., *Ann. NY Acad. Sci.* 886: 289–92 (1999).

Figure 3:
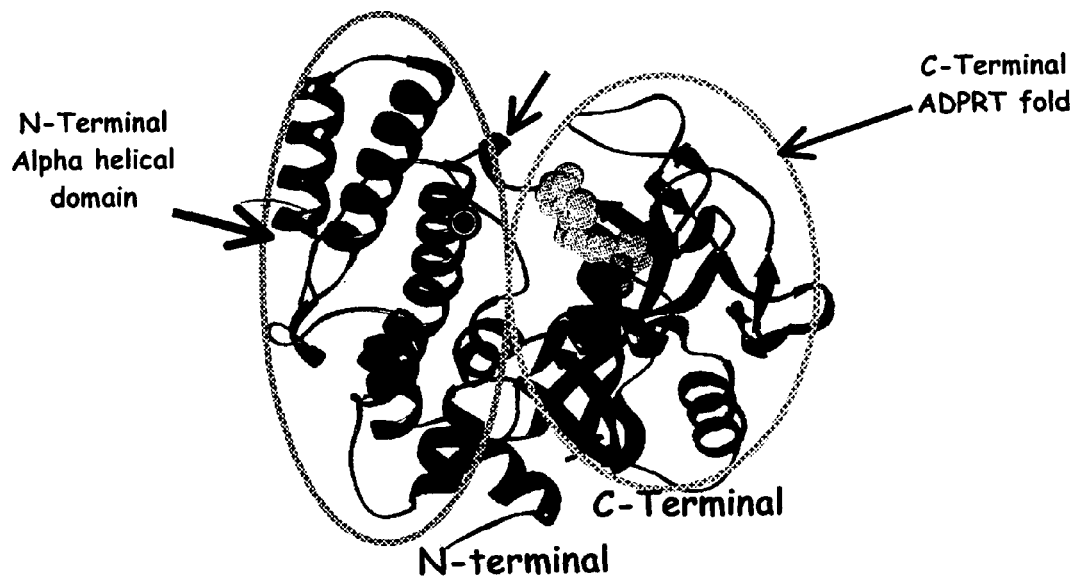
FIG. 3 is a ribbon drawing of the catalytic fragment of PARP-1 (CF-PARP-1). The N-terminal all alpha domain is on the left side of the figure and the ADP-ribosyltransferase domain or ADPRT on the right. The all alpha domain forms a pocket for the binding of the adenine portion the NAD substrate (also known as the donor site). The ADPRT fold binds the acceptor site or elongating poly(ADP-ribose) polymer. The PXXP SH3 ligand (SEQ ID NO: 2) lies in a loop at the interface between the all alpha domain and the ADPRT fold. The gain of function mutation L613F (SEQ ID NO: 18) maps to the all alpha helical domain right at the interface where the PXXP motif is localized.
Figure 5:
FIG. 5 is a diagram of the tertiary structure of a typical SH3 module, showing the surface responsible for recognition of the PXXP ligand. Two clusters of aromatic residues in the sequence form the peptide-binding surface. The conserved YDF motif (SEQ ID NO: 19) is found at the N-terminal end of the SH3 sequence at the beginning of the first loop (also known as RT-loop). The WXXPXXY motif (SEQ ID NO: 20) is found at the C-terminal end just before the very last strand. The two loops surrounding the peptide-binding surface contribute to the specificity of the interaction.

PARP-1 contains an SH3 domain and an SH3-ligand domain. During an analysis of an alignment of several PARP sequences, we found that PARP-1 contains a previously unknown SH3 domain (SEQ ID NO: 30) and a previously unknown SH3-ligand domain (SEQ ID NO: 34). FIG. 1A shows the location of the predicted SH3 and SH3-ligand domains in PARP-1 and shows that these domains are not present in the other members of the PARP family of proteins. From this analysis, the CF-fragment of PARP-1, whose structure had been determined, was found to contain a PXXP sequence localized within a surface accessible loop, which leads to the active site of PARP-1 (FIG. 3 and FIG. 5). The sequence contained a conserved arginine residue (R778, human sequence; SEQ ID NO: 4) found at the N-terminal end of the PXXP, with a three-residue spacing between R778 and the first proline P881 of the PXXP motif (see, TABLE I, below). This is one residue longer than that expected for a standard class I SH3 ligand. The proline-rich binding domain within the human PARP-1 sequence contains the sequence: RIAPPEAPNT (SEQ ID. NO: 35), conforming to the classic PXXP motif.

Figure 2:
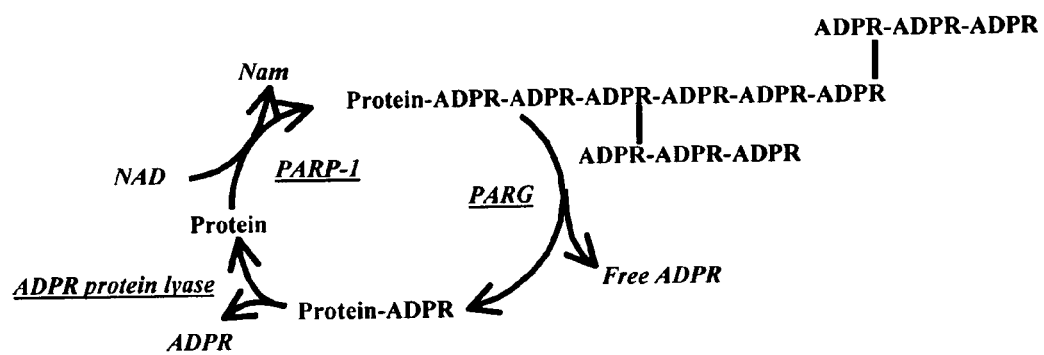
FIG. 2 is a pictorial description of the ADP-ribose polymer cycle. Polymer biosynthesis involves the action of PARP-1, which utilizes NAD. ADP-ribose polymers are short lived and degraded by poly(ADP-ribose) glycohydrolase (PARG).

TABLE I shows a selected portion of the sequence alignment of PARP family between residues 656–1014 found within a loop connecting beta strand 1 and 2 of the core ADPRT fold (FIG. 2). Only PARP-1 and PARP-2 contain the PXXP SH3 binding core motif, while PARP-3, tankyrase and vault-PARP show little sequence conservation in this loop, which is not only surface accessible, but also lies behind the active site of PARP-1, such that its extension residues form part of the PARP-1 active site.

TABLE I

| PARP Protein | Peptide Sequence Alignment | SEQ ID NO |
|---|---|---|
| PARP-1 human | GLRIAPPEAPVT-----GYMF: | SEQ ID NO: 41 |
| PARP-1 mouse | GLRIAPPEAPVT-----GYMF: | SEQ ID NO: 42 |
| PARP-1 rat | GLRIAPPEAPVT-----GYMF: | SEQ ID NO: 43 |
| PARP-2 human | GLRIAHPEAPIT-----GYMF: | SEQ ID NO: 44 |
| PARP-2 mouse | GLRVAPPEAPIT-----GYMF: | SEQ ID NO: 45 |
| PARP-3 human | GLRIMPHS---------GGRV: | SEQ ID NO: 46 |
| tankyrase | GFDERHAYI--------GGMF: | SEQ ID NO: 47 |
| vault PARP | APPGYDSVHGVSQTASVTTDF: | SEQ ID NO: 48 |

The finding of the PXXP motif prompted an immediate search for regions of the PARP-1 sequence with no known function, but with a high probability of beta sheet prediction using the algorithm of Stultz C M, White J V, & Smith T F, *Protein Sci.* 2(3): 305–14 (1993). Since the structure of CF-PARP-1 is known, the search focused on the N-terminal fragment, which contains an assigned domain of no clear function (C domain).

We performed a secondary structure prediction of PARP-1 N-terminal domain, including predictions for beta sheet, alpha helix and turns and solvent accessibility. The results support the existence of a SH3 domain within the PARP-1 C domain. Since most of the PARP-1 domains have been mapped, the secondary structure prediction focused on the region between the N-terminal zinc fingers and the BRCT domain. This region between residues 240 and 400 (human sequence) showed a 60 reside region with a mostly beta sheet prediction within the PARP-1 C domain (see, FIG. 1A).

Figure 6:
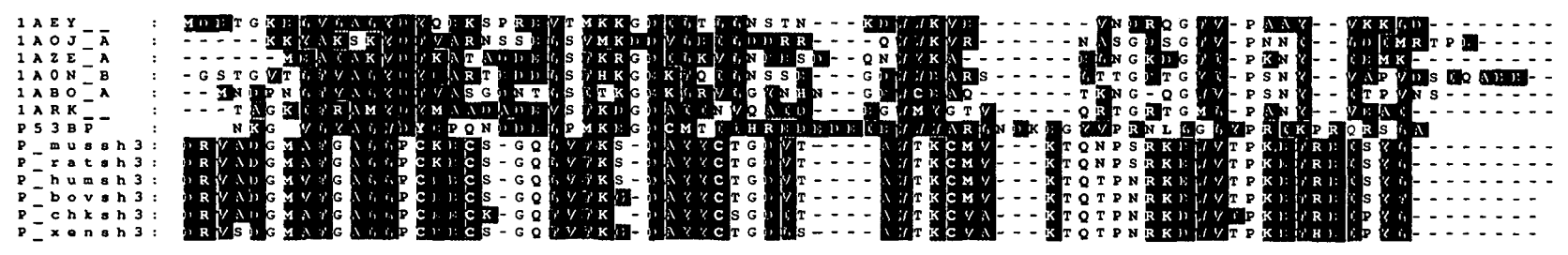

The sequence of PARP-1 between residues 280–350 was compared with sequences of other SH3 domains of known structure obtained from the Protein Data Bank (PDB) database. The Protein Data Bank is operated by Rutgers, The State University of New Jersey; the San Diego Supercomputer Center at the University of California, San Diego; and the National Institute of Standards and Technology—three members of the Research Collaboratory for Structural Bioinformatics (RCSB). FIG. 6 is a sequence alignment of a select group of SH3 domains (top 7 sequences) whose structures have been determined and deposited in the PDB database. The first three letters of the sequence identification indicates the PDB code: 1AEY (SEQ ID NO: 21); 1AOJ_A (SEQ ID NO: 22); 1AZE_A (SEQ ID NO: 23); 1A0N_B (SEQ ID NO: 24); 1ABO_A (SEQ ID NO: 25); 1ARK (SEQ ID NO: 26); P53BP (SEQ ID NO: 29). The bottom 6 sequences are those from the C domain of PARP-1 from mouse (P_mussh3; SEQ ID NO: 28), rat (P_ratsh3; SEQ ID NO: 29), human (P_humsh3; SEQ ID NO: 30), bovine (P_bovsh3; SEQ ID NO: 31), chicken (P_chksh3; SEQ ID NO: 32) and Xenopus (P_xensh3; SEQ ID NO: 33).

FIG. 6 shows the conserved sequences among the SH3 domains. The determination of which sequences are conserved, as well as guidance for the possible substitution of an equivalent amino acid for any amino acid in a peptide sequence, thereby maintaining the structure and function of the polypeptide, is well-known to those of skill in the molecular biological arts (see, Alberts B et al., *Molecular Biology of the Cell*. 3rd ed. (New York: Garland Publishing, 1994); Lewin B, *Genes VI*. (New York, Oxford University Press, 1997); Lodish H et al., *Molecular Cell Biology.* 4th ed. (New York, W. H. Freeman and Company, 1999); Strachan T & Read A P, *Human Molecular Genetics,* 2nd ed. (New York: John Wiley & Sons, 1999)). These determinations can be performed using commercially available computer programs, such as DNA Strider and Wisconsin GCG. These determinations can also be performed using more sophisticated molecular modeling software, such as Insight II, described in EXAMPLE 3.

Based on the conserved sequences of the conserved sequences of the six PARP-1 SH3 domains in FIG. 6, a consensus PARP-1 SH3 domain can be written as DRVXDGMXFGALLPCXECSGQXVFKX-DAYYCXGDXXAWTKCXXKTQXPXRKXWVX PKEFXEIXYL (SEQ ID NO: 1))

The sequence comparison of PARP-1 C domain with that of a select group of SH3 domains with known 3D-structure revealed a set of conserved aromatic residues that map to the peptide-binding surface of SH3 domains. The sequence variability is restricted to three loop regions of the SH3; two of them are the RT and n-src loop, which surround the peptide-binding surface. The sequence comparison below also reveals that PARP-1-SH3 likely belongs to a separate subgroup. The first subgroup represented by the top six sequences represents the classic SH3 domain with recognition favoring class I peptides with an arginine residue at the N-terminal end of the PXXP motif. The second subgroup is represented by P53 binding protein (P53BP), which by far has the largest insertions in the n-src loop and the loop connecting S3 to S4. The PARP-1 vertebrate sequences form the third subgroup, which in terms of size of its loop is closer to subgroup I.

As shown in FIG. 6, the hydrophobic residues that make up the SH3 core are conserved in PARP-1 SH3. Five strands (S1, S2, S3, S4, S5) form the SH3 domain. A single helical region contains a conserved proline at the beginning. PARP-1 -SH3 differs from other SH3 domain in the lack of conservation of the YDF motif (SEQ ID NO: 19) at the N-terminal end (see FIG. 5). A break in aromatic conservation is also found in P53-binding protein SH3 domain, which does not conserve the C-terminal aromatic motif FXXPXXY (SEQ ID NO: 36). This suggests that at least one set of aromatic motifs must be conserved in the SH3 module.

Moreover, a published random mutagenesis experiment had been performed in PARP-1, where Trucco et al., *Mol. Cell Biochem.* 193(1–2): 53–60 (1999) were looking for activation deficient mutants of PARP-1 that were still capable of binding to DNA and retaining basal level of activity. The Trucco experiments of revealed a point mutation within domain C, G313E mutation (SEQ ID NO: 37), which generated an "activation deficient mutant". Trucco suggested that the deficiency of the G313E mutant was a result of either an "induced strong change in the tertiary structure of the enzyme or plays an important role in self-association and/or in heterodimerization with other proteins." Viewing the Trucco interpretation in light of our SH3 and SH3-ligand domain assignments, domain C may be involved in protein interactions, which is herein proposed to be a novel SH3, SH3-ligand interaction.

Thus, the existence of a PARP-1 SH3 domain shows that PARP-1 can be activated by cytoplasmic proteins, independent of DNA damage. Based upon the deduced existence of a PARP-1-SH3 and SH3 ligand domains, a model for PARP-1 activation upon DNA recognition has been formed. The model is summarized in FIG. 1C, which shows that DNA recognition by the zinc fingers, ZI and ZII, triggers PARP-1 activation, through SH3 and SH3-ligand domains.

Since PARP-1 activity is known to require dimer formation, dimerization involves the inter-molecular interaction between the SH3 domain of one monomer and the SH3-ligand of a second PARP-1 monomer. Since activation depends on DNA binding, this may trigger dimerization, as shown in FIG. 1B. According to FIG. 1B, dimerization through PARP-1-SH3 puts the automodification/BRCT domain in close proximity to the catalytic domain. FIG. 7 shows two structural possibilities.

This approach to understanding the PARP-1 mechanism of action is a classic one, where the PARP-1 domains are separated from the full-length protein and the behavior of the separate units identified. Understanding how these domains function individually enables us to address their function in the context of the full length PARP-1 and determine potential coöperativity between domains during PARP-1 activation.

The discovery of the proline-rich sequence in PARP-1 opens a new area for the design of selective inhibitors of PARP-1 that focuses on the mechanism of PARP-1 activation and not its catalytic activity. This approach includes the generation and use of peptide inhibitors or peptide mimics of proline-rich sequence.

The importance of this finding is strengthened by the discovery of several PARP-1-like proteins containing a highly conserved catalytic domain. However, these PARP-1 inhibitors have targeted the catalytic domain and as a result, all PARP-1 inhibitors lack selectivity. By contrast, the invention provides methods of selectively targeting PARP-1 for designing therapeutic compounds that are radio- and/or chemosensitizing, for example, or for developing therapeutic agents for stroke or diabetes type 1.

Jagtap et al., *Crit. Care Med.* 30(5):1071–82 (2002) developed phenanthridinone PARP-1 inhibitors and tested them in vivo and in vivo for the ability to reduce PARP activation and to protect against various cytotoxic events. The compounds were shown to have significant cryoprotective effects in vitro and significant protective effects in shock and reperfusion in vivo. Ha et al., *Neurobiol.* 7(4):225–39 (2000), showed that PARP-1 over-activation caused by cellular insults appears to play a prominent role in stroke and other neurodegenerative processes in which PARP-1 gene deletion and PARP-1 inhibiting drugs provide protection. Mabley, et al., *Br. J. Pharmacol.* 133(6):909–19 (2001), investigated the role of PARP in mediating the induction of diabetes and β-cell death in the multiple-low-dose-streptozotocin (MLDS) model of type 1 diabetes. An inhibitor of PARP was found to protect mice from MLDS and prevent β-cell loss, in a dose dependent manner. These publications provide evidence that the activation of PARP contributes to β-cell damage and death in the MLDS model of diabetes, and indicate a use for PARP activation in cytokine-mediated depression of insulin secretion and cell viability in vitro.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLE 1

PARP-1 Bacterial Expression Vectors

A fragment containing PARP-1-SH3, residues 280–340 was PCR cloned using primers with BamHI and XhoI restriction sites. The fragment was cloned into two expression vectors, Pet28a (Novagen) and PEGX (Stratagene).

The two vectors contain a histidine tag and a GST fusion protein respectively. These two tags serve two purposes: (1) for use in a single step purification of PARP-1-SH3 followed by removal of the tag using a thrombin cleavage site (The thrombin used in the cleavage reaction can be removed by using biotinylated thrombin); and (2) the PGEX vector containing the GST fusion protein also serves the purpose of enhancing the solubility of the recombinant protein.

The fragment can be subcloned into a pTYB(NEB) vector, which attaches a chitin binding/intein self-cleaving domain. Chong S et al., Gene 192(2): 271–81 (1997). After induction with IPTG, the fusion protein is purified using a chitin-binding column. Once the fusion protein is attached to the column, DTT is added to induce the self-cleaving activity of intein. The purified native protein is eluted while the intein domain remains attached to the column.

An SDS PAGE gel has been used to separate the GST purified fusion protein and the thrombin cleaved fragment, releasing the 6 kDa SH3 fragment.

Both of these constructs can now be used to investigate their ability to bind to full-length PARP-1 using (1) a GST pulldown assay and (2) a surface plasmon resonance assay employing a BIACORE instrument. A PARP-1 activation assay in the presence of different domains can be used to identify interactions necessary for activation.

EXAMPLE 2

Structure/Function Testing

The binding of PARP-1 to DNA strand breaks results in its activation by the interaction of SH3 and SH3-ligand domains. This model provides the rationale for the development of a new drug discovery paradigm for generation of PARP-1 inhibitors for cancer therapy.

Functional Test of the Model Regarding the SH3 and SH3-ligand Domains of PARP-1. Directed mutagenesis is used to generate single amino acid changes to disrupt the peptide recognition surface of the PARP-1 SH3 domain and the SH3-ligand domain. Disruption of either domain results in a PARP-1 that is unable to be activated by DNA strand breaks.

Human PARP-1 SH3 is mutated at residues that map to a conserved, and predominately aromatic surface (L293A, P294A, C295A, W318A, W333A, P336A and F339A) involved in the recognition of the proline-rich PXXP SH3-ligand (PPII). The site-directed mutants are designed to maintain structural integrity of the SH3 domain, while disrupting its ability to interact with the SH3-ligand found in CF-PARP-1 (TABLE I).

In particular, the full length PARP-1 and its mutants are expressed in Sf9 insect cell/baculovirus system and purified using an affinity chromatography on 3-aminobenzamide Afi-Gel 10, which was also used in the crystallization of the CF-PARP-1. Decker P et al., Clin. Cancer Res. 5: 1169–72 (1999).

Site directed mutagenesis is performed using Quick-Change® method (Stratagene). All mutations are performed on a subclone of PARP-1 containing either the catalytic fragment of PARP-1 or the domain C of PARP-1 (see, FIG. 1A). Each subclone is engineered with unique restriction sites at both ends allowing us to piece together a point mutated full length PARP-1.

The PARP-1 activation assay is as described by Rolli V et al., Biochemistry 36: 12147–54 (1997). The DNA binding assay is performed as described by Gradwohl G et al, Proc. Natl. Acad. Sci. USA 87: 2990–4 (1990).

Also, the PXXP motif is disrupted with the mutations, P881A (SEQ ID NO: 38), P882A (SEQ ID NO: 39) and P885A (SEQ ID NO: 40), all of which disable the PPII structure and consequently disable PARP-1 activation. The ability of PARP-1 mutants to bind to DNA and its basal level of activity serves as a control that the mutations are not disabling as to catalytic activity or DNA binding.

The mutations in PARP-1 SH3 could conceptually generate three potential phenotypes: (1) a constitutively active PARP-1, (2) an activation knockout of PARP-1; or (3) wild type PARP-1 (unlikely). Constitutive active mutants would suggest that the C domain keeps PARP-1 in the OFF state. An activation knockout effect suggests either: (a) that domain C is vital for turning catalytic activity ON, or (b) that the mutation has disrupted PARP-1 structure. The latter possibility is investigated as shown below. The observation of a wild type phenotype for all the seven mutations is unlikely, since there is experimental data maps an activation deficient mutant of PARP-1 to the SH3 domain.

Structural Analysis by Characterization of the Solution Structure of the Wild Type and Site-Directed Mutants of the SH3 Domain by Circular Dichroism and Screening for Crystallization Conditions. Circular Dichroism (CD) measurements provide a fast, relatively simple and established method for estimating the relative content of protein secondary structure. CD measurements with the purified fragment of PARP-1 SH3 support the deduced beta sheet structure, supporting the fold model and enabling more elaborate methods such as X-ray crystallography and/or NMR. The CD experiments are also performed on site-directed mutants of PARP-1 SH3 (see, above). Since these mutations are designed to alter surface properties and not the predicted SH3, the results provide a control that the mutations have not affected the molecular structure of PARP-1 SH3.

The structure determination of PARP-1 SH3 using X-ray crystallographic techniques provides the ultimate evidence of an SH3 fold.

The predicted SH3 domain of PARP-1 and the site directed mutants of PARP-1 SH3 domain are expressed as a GST-fusion protein (PGEX vector, Pharmacia/LKB Technology) and a polyhistidine-tag (HIS-tag) vector (Pet28c, Novagen). The tags are useful for the purification of the predicted SH3 domain and can be cleaved off using a biotinylated thrombin, enabling the capture of the thrombin (Novagen). The CD spectra are measured and program CONTIN (Bousquet J A et al., Biochemistry 39, 7722–35 (2000)) used to extract secondary structure content.

The expressed PARP-1 SH3 peptides are also screened for crystallization, to determine the structure using crystallographic techniques. 3D-structures of the SH3 domains of other proteins are known, thus providing guidance for the analysis of PARP-1 SH3 structure.

Structure/Function Test of the Physical Interaction of PARP-1 SH3 and SH3-ligand Domains By Direct Binding Experiments. To show that PARP-1 contains a functional SH3 domain involved in its activation, the SH3 domain should be shown to bind directly to the SH3-ligand found in CF-PARP-1.

Binding of the GST-SH3 fusion construct with the catalytic fragment of PARP-1 (CF-PARP-1) is assayed using glutathione beads to immobilize GST-SH3. Complex detection are done using Western blots with anti-GST and commercial PARP-1 antibodies. CF-PARP-1 mutants that disrupt the putative polyproline helix II (PPH) (SH3-ligand domain) are used as a negative control.

Binding assays follow procedures used for characterization of SH3 domains. Mosser EA et al., *Biochemistry* 37: 13686–95 (1998). The GST and HIS-tags are used to immobilize the SH3 domain. Then, binding of PARP-1 SH3 to CF-PARP-1 and mutants of CF-PARP-1 with alterations in the SH3-ligand domain (PXXP motif, FIG. 3) is tested as follows: RIAAAEAP (SEQ ID NO:41), RIAPAEAA (SEQ ID NO: 42) and RIAAPEAA (SEQ ID NO: 43). Commercial antibodies against GST, HIS-tag and CF-PARP-1 are used in western blots to identify protein complexes. The ability of PARP-1 SH3 to interfere or compete with the natural SH3 ligand is tested by adding increasing amounts of PARP-1 SH3 to the activation assay of wild type PARP-1.

EXAMPLE 3

Molecular Modeling in Designing PARP-1 Inhibitors

Based upon the now determined structure of the SH3 domain and SH3-ligand domain of PARP-1, known and predicted compounds can be tested by molecular simulations for interaction with PARP-1, using InsightII (Molecular Visualization (MolViz) Facility Department of Chemistry Indiana University, Bloomington, Ind. USA) and other modeling software.

First, the structure of the PARP-1 SH-3domain or the PARP-1 SH3-ligand domain in a digital format that can be used by a molecular modeling computer program. The molecular modeling software generally provides information regarding which digital format is acceptable for that program. Next, the structure of a compound suspected of molecularly interacting with the PARP-1 SH-3domain or the PARP-1 SH3-ligand domain is obtained. The "molecularly interacting" can be covalent, ionic or other noncovalent binding. Guidance for how the compound may molecularly interact with these domains is provided above. Then, the structure of the compound suspected of molecularly interacting with the PARP-1 SH-3domain or the PARP-1 SH3-ligand domain in a digital format that can be used by the molecular modeling computer program. The molecular modeling computer program is operated to determine (1) whether the PARP-1 SH-3domain molecularly interacts with the compound suspected of molecularly interacting with the PARP-1 SH-3domain, or (2) whether the PARP-1 SH3-ligand domain molecularly interacts with the compound suspected of molecularly interacting with the PARP-1 SH3-ligand domain, using the instructions provided by the molecular modeling software and methods known to those of skill in the bioinformatics art. Based upon this operation, it is possible to identify a compound that interacts molecularly as being a potential therapeutic agent.

Guidance for a comparison of structural and dynamic properties of different simulation methods applied to SH3 can be found in scientific publications, including van Aalten V M F et al., *Biophys. J.* 70: 684–692 (1996), Hansson H et al., *Biochemistry (*2001), and Garbay C et al., *Biochem. Pharmacol.* 60(8): 1165–9 (2000), among others.

EXAMPLE 4

Structural/Functional Model of the L613F PARP-1 Mutant

To achieve selective targeting of the PARP-1 enzyme, we investigated the structure of the PARP-1 protein and the mechanism of PARP-1 activation upon DNA damage recognition.

The sequence of PARP-1 has a unique set of domains, including two zinc finger DNA binding domain and a conserved C-terminal domain similar to the breast cancer 1 gene (BRCA1), which is involved in protein-protein interaction also called BRCT. Deng C X & Brodie S G, *BioEssays* 22(8): p. 728–37 (2000); Bork P et al., *Faseb J.* 11(1): 68–76 (1997). Also, PARP-1 contains a src homology 3 like domain (SH3) and SH3 ligand domains. Macias M. J et al., *FEBS Lett.* 513(1): 30–7 (2002). Furthermore, the G313E mutation (SEQ ID NO: 37) interferes selectively with the mechanism of activation of PARP-1 and maps to the PARP-1-SH3.

Based on these lines of evidence we developed a model for PARP-1 activation upon DNA recognition. Since PARP-1 activity requires dimer formation, dimerization should involve the inter-molecular interaction between the SH3 domain of one monomer and the SH3-ligand of a second PARP-1 monomer. This model is a classical approach towards understanding PARP-1 mechanism of action, since we are first separating the domains from the full length PARP-1 and then identifying their behavior as separate units. By first understanding how these domains function individually, we can then address their function in the context of the full length PARP-1 protein and determine potential coöperativity between domains during PARP-1 activation.

Accordingly, we have now modeled a gain of function mutation L613F that maps to the catalytic fragment of PARP-1, whose structure has been determined. (SEQ ID NO: 18); Ruf A et al., *Proc. Natl. Acad. Sci. USA.* 93(15): 7481–5 (1996). This mutation generates a PARP-1 protein that has a catalytic power ($k_{cat}/K_M$) one order of magnitude higher than wild type PARP-1, in the absence of DNA. Miranda EA et al., *Biochem. Biophys. Res. Commun.* 212(2): 317–25 (1995). The mutation maps to the catalytic fragment of PARP-1. The structure of the catalytic fragment of PARP-1 contains two domains, an all alpha domain and a conserved ADP-ribosyltransferase domain (ADPRT) (FIG. 3). The two domains interact with each other through a loop that contains a PXXP motif (SEQ ID NO: 2), which should be the ligand for the PARP-1-SH3 domain (see, FIG. 1B). The mutation L613F maps the all alpha domain of CF-PARP-1 right next to the PXXP loop. We produced the structural L613F mutant model utilizing the known structure of the catalytic fragment of PARP-1. The L613F mutation involves an amino acid change to a bulkier hydrophobic residue. This added bulkiness at position 613 affects the structure of the neighboring loop that contains our PXXP proline rich loop. This structural model is consistent with our functional model that suggests that the binding of PARP-1-SH3 to the PXXP loop found in the catalytic fragment of PARP-1 which separate the two domains (all alpha and ADPRT) operates in much the same way that the L613F alteration, which provides a bulkier side chain, affects the activity of CF-PARP-1.

EXAMPLE 5

Drugs That are Selectively Designed For PARP-1

In one embodiment, small peptides with the sequence RIAPPEAPV (SEQ ID NO: 7) compete with the natural ligand of PARP-1. This sequence is unique to PARP-1 and should bind poorly to other SH3 domains, such as those that are found in cell signaling molecules such as src-kinases. We generated binding evidence utilizing the software SPOT-SH3, which has been shown to predict the ability of peptide sequences to bind to SH3 domains. Brannetti B et al., *J. Mol. Biol.* 298(2): 313–28 (2000). SPOT-SH3 has been experimentally validated. Politou, A S et al., *J. Mol. Biol.* 316(2): 305–15 (2002).

Natural ligands of other SH3 domain bind their ligand PXXP sequence with a predicted score in the range 0.7 to 0.9. By contrast, by utilizing the PARP-1 SH3 ligand sequence, we obtain only a score of 0.6. This result shows that the PARP-1 proline-rich sequence RIAPPEAPV should bind poorly to other SH3 sequences, so that peptides with sequence RIAPPEAPV (SEQ ID NO: 7) selectively bind to PARP-1 and inhibit its activity.

Guidance as to the amount of peptide with sequence RIAPPEAPV (SEQ ID NO: 7) that is sufficient to bind to the PARP-1 SH3 domain and inactivate the PARP-1 or functional fragment thereof is provided by comparison with the amount of inhibitors (derivatives of benzamides and fused ring heterocycles) used to target the conserved NAD binding site (pADPRT domain) of PARP-1, which present in all of the PARP family members. Ruf A. et al., *Biochemistry* 37(11): 3893–900 (1998); Tentori L et al., *Pharmacol Res.* 45(2): 73–85 (2002); Jacobson M K & Jacobson E L, *Trends Biochem Sci.* 24(11): 415–7 (1999). See also, U.S. Pat. Nos. 6,201,020, 6,121,278, 5,587,384, 5,215,738; 5,041,653 and 5,032,617, each incorporated herein by reference. Assays to measure an amount of a compound sufficient to affect PARP-1 activity or inhibition are commercially available (Trevigen® PARP Activity Assay Kit and Trevigen® PARP Inhibition Assay Kit; Trevigen, Inc., 8405 Helgerman Court, Gaithersburg, Md. USA 20877).

The use of peptide mimics is a strategy that has already been successfully used in the design of selective inhibitors for other SH3 domain proteins. Nguyen J T et al., *Chem. Biol.* 7(7): 463–73 (2000). Now, the use of peptide mimics is a useful strategy for increasing the binding potency of peptide ligands to PARP-1-SH3.

The foregoing description has been presented only for the purposes of illustration and is not intended to limit the invention to the precise form disclosed, but by the claims appended hereto.

What is claimed is:

1. A method for identifying agents that selectively inactivate poly(ADP-ribose) polymerase-1 (PARP-1), comprising the steps of:
   (a) contacting a test compound with a polypeptide comprising the PARP-1 src-homology domain 3 (SH-3 domain), the PARP-1 SH-3 ligand domain, or both domains;
   (b) determining whether the test compound binds to the SH-3 domain or PARP-1 SH-3 ligand domain;
   (c) assaying any test compound that binds to the SH-3 domain or PARP-1 SH-3 ligand domain to determine whether the compound inactivates or prevents the activation of PARP-1; and
   (d) identifying the test compound as a compound that selectively inactivates or prevents the activation of PARP-1.

2. The method of claim 1, wherein the polypeptide is a PARP-1 fusion protein.

3. The method of claim 1, wherein the polypeptide has been expressed in *Spodoptera frugiperda* 9 (Sf9) insect cell/baculovirus system and purified using an affinity chromatography.

4. The method of claim 1, wherein the assaying is by a method selected from the group consisting of sedimentation equilibrium, gel permeation, electrophoretic mobility and kinetics measurements.

5. A method for identifying agents that activate poly (ADP-ribose) polymerase-1 (PARP-1), comprising the steps of:
   (a) contacting a test compound with a polypeptide comprising the PARP-1 src-homology domain 3 (SH-3 domain), the PARP-1 SH-3 ligand domain, or both domains;
   (b) determining whether the test compound binds to the SH-3 domain or PARP-1 SH-3 ligand domain;
   (c) assaying any test compound that binds to the SH-3 domain or PARP-1 SH-3 ligand domain to determine whether the compound activates PARP-1; and
   (d) identifying the test compound as a compound that selectively activates PARP-1.

* * * * *